(12) United States Patent
Kovacs

(10) Patent No.: US 10,451,473 B2
(45) Date of Patent: Oct. 22, 2019

(54) PHYSIOLOGICAL ASSESSMENT SCALE

(71) Applicant: Physiowave, Inc., Santa Clara, CA (US)

(72) Inventor: Gregory T. Kovacs, Palo Alto, CA (US)

(73) Assignee: Physiowave, Inc., Menlo Park, CA (US)

( * ) Notice: Subject to any disclaimer, the term of this patent is extended or adjusted under 35 U.S.C. 154(b) by 90 days.

(21) Appl. No.: 15/468,439

(22) Filed: Mar. 24, 2017

(65) Prior Publication Data
US 2017/0261365 A1 Sep. 14, 2017

Related U.S. Application Data

(63) Continuation of application No. PCT/US2015/052168, filed on Sep. 25, 2015, which
(Continued)

(51) Int. Cl.
*G01G 19/44* (2006.01)
*G01G 19/50* (2006.01)
(Continued)

(52) U.S. Cl.
CPC .......... *G01G 19/44* (2013.01); *A61B 5/0205* (2013.01); *A61B 5/0535* (2013.01);
(Continued)

(58) Field of Classification Search
CPC ........ G01G 19/44; G01G 19/50; G01G 21/22; G01G 23/37
See application file for complete search history.

(56) References Cited

U.S. PATENT DOCUMENTS 3,702,113 A 11/1972 Blockley et al.
4,195,643 A 4/1980 Pratt, Jr.
(Continued)

FOREIGN PATENT DOCUMENTS

DE 202009012748 12/2009
DE 202009012748 U1 * 1/2010 ............. G01G 19/44
(Continued)

OTHER PUBLICATIONS

Machine translation of DE 20 2009 012 748 U1.*
(Continued)

*Primary Examiner* — Natalie Huls
(74) *Attorney, Agent, or Firm* — Crawford Maunu PLLC

(57) ABSTRACT

Physiological assessment scale systems and methods are implemented using a variety of approaches. According to one implementation, a scale measures the physiological data of a user engaging sensor circuitry on a platform region of the scale. In a physiological assessment mode, physiological data of the user is detected at respective states of physical exertion. The physiological data is then processed by user-targeted circuitry to determine physiological parameters of the user pertaining to the respective physical exertion states, such as may pertain to an increase in exertion or a reduction in exertion. These physiological parameters may, for example, be used to provide an indication of the physical health and fitness of the user. Such parameters may then be associated with the user and saved to a data-access circuit, and also forwarded to a display which communicates the physiological parameters among other information to the user through the platform region.

21 Claims, 27 Drawing Sheets

Related U.S. Application Data is a continuation of application No. 14/498,773, filed on Sep. 26, 2014, now Pat. No. 9,546,898, which is a continuation-in-part of application No. 14/338,266, filed on Jul. 22, 2014, now Pat. No. 10,130,273, which is a continuation-in-part of application No. 14/332,140, filed on Jul. 15, 2014, now Pat. No. 9,943,241.

(60) Provisional application No. 62/027,724, filed on Jul. 22, 2014, provisional application No. 62/011,466, filed on Jun. 12, 2014.

(51) Int. Cl.
*A61B 5/0205* (2006.01)
*A61B 5/053* (2006.01)
*A61B 5/00* (2006.01)
*A61B 5/0245* (2006.01)
*A61B 5/0408* (2006.01)
*A61B 5/11* (2006.01)
*A61B 5/021* (2006.01)
*A61B 5/107* (2006.01)

(52) U.S. Cl.
CPC .......... *A61B 5/7445* (2013.01); *G01G 19/50* (2013.01); *A61B 5/0077* (2013.01); *A61B 5/0245* (2013.01); *A61B 5/02125* (2013.01); *A61B 5/04085* (2013.01); *A61B 5/0537* (2013.01); *A61B 5/1074* (2013.01); *A61B 5/1102* (2013.01); *A61B 5/4812* (2013.01); *A61B 5/7203* (2013.01); *A61B 5/7225* (2013.01); *A61B 5/7405* (2013.01); *A61B 5/7455* (2013.01)

(56) References Cited

U.S. PATENT DOCUMENTS

| | | |
|---|---|---|
| 4,362,164 A | 12/1982 | Little et al. |
| 4,557,271 A | 12/1985 | Stoller et al. |
| 4,657,025 A | 4/1987 | Orlando |
| 4,679,569 A | 7/1987 | Lee |
| 4,765,321 A | 8/1988 | Mohri |
| 4,836,215 A | 6/1989 | Lee |
| 4,898,182 A | 2/1990 | Hawkins et al. |
| 4,947,857 A | 8/1990 | Albert et al. |
| 4,958,638 A | 9/1990 | Sharpe et al. |
| 5,314,389 A | 5/1994 | Dotan |
| 5,431,170 A | 7/1995 | Mathews |
| 5,620,003 A | 4/1997 | Sepponen |
| 5,678,562 A | 10/1997 | Sellers |
| 5,682,902 A | 11/1997 | Herleikson |
| 5,701,894 A | 12/1997 | Cherry et al. |
| 5,750,937 A | 5/1998 | Johnson et al. |
| 5,782,238 A | 7/1998 | Beitler |
| 5,833,623 A | 11/1998 | Mann et al. |
| 6,047,203 A | 4/2000 | Sackner et al. |
| 6,080,110 A | 6/2000 | Thorgersen |
| 6,168,563 B1 | 1/2001 | Brown |
| 6,198,394 B1 | 3/2001 | Jacobsen et al. |
| 6,205,547 B1 | 3/2001 | Davis |
| 6,228,033 B1 | 5/2001 | Koobi et al. |
| 6,292,690 B1 | 9/2001 | Petrucelli |
| 6,331,162 B1 | 12/2001 | Mitchell |
| 6,454,708 B1 | 9/2002 | Ferguson et al. |
| 6,454,719 B1 | 9/2002 | Greenhut |
| 6,516,221 B1 | 2/2003 | Hirouchi et al. |
| 6,551,252 B2 | 4/2003 | Sackner et al. |
| 6,594,759 B1 | 7/2003 | Wang |
| 6,640,134 B2 | 10/2003 | Raymond et al. |
| 6,685,634 B1 | 2/2004 | Fry |
| 6,702,754 B2 | 3/2004 | Ogura et al. |
| 6,705,990 B1 | 3/2004 | Gallant |
| 6,734,856 B2 | 5/2004 | Ishikawa et al. |
| 6,755,783 B2 | 6/2004 | Cosentino et al. |
| 6,783,498 B2 | 8/2004 | Sackner et al. |
| 6,790,178 B1 | 9/2004 | Mault et al. |
| 6,814,705 B2 | 11/2004 | Kawaguchi |
| 6,847,892 B2 | 1/2005 | Zhou et al. |
| 6,875,174 B2 | 4/2005 | Braun et al. |
| 6,898,299 B1 | 5/2005 | Brooks |
| 6,962,566 B2 | 11/2005 | Quistgaard et al. |
| 6,963,035 B2 | 11/2005 | Honda et al. |
| 7,137,955 B2 | 11/2006 | Bartels et al. |
| 7,257,438 B2 | 8/2007 | Kinast |
| 7,313,435 B2 | 12/2007 | Nakada et al. |
| 7,316,648 B2 | 1/2008 | Kelly et al. |
| 7,336,266 B2 | 2/2008 | Hayward et al. |
| 7,382,247 B2 | 6/2008 | Welch et al. |
| 7,384,410 B2 | 6/2008 | Eggers et al. |
| 7,417,536 B2 | 8/2008 | Lakshmanan et al. |
| 7,459,644 B2 | 12/2008 | Kenmochi |
| 7,502,643 B2 | 3/2009 | Farringdon et al. |
| 7,593,632 B2 | 9/2009 | Schnell |
| 7,668,588 B2 | 2/2010 | Kovacs |
| 7,787,946 B2 | 8/2010 | Stahmann et al. |
| 7,796,013 B2 | 9/2010 | Murakami et al. |
| 7,846,104 B2 | 12/2010 | MacQuarrie et al. |
| 7,899,522 B1 | 3/2011 | Koh et al. |
| 8,200,320 B2 | 6/2012 | Kovacs |
| 8,332,026 B2 | 12/2012 | Cha et al. |
| 8,369,936 B2 | 2/2013 | Farringdon et al. |
| 8,452,390 B2 | 5/2013 | Jensen |
| 8,473,041 B2 | 6/2013 | Bartnik et al. |
| 8,475,367 B1 | 7/2013 | Yuen et al. |
| 8,475,368 B2 | 7/2013 | Tran et al. |
| 8,529,409 B1 | 9/2013 | Lesea-Ames |
| 8,548,556 B2 | 10/2013 | Jensen |
| 8,639,226 B2 | 1/2014 | Hutchings et al. |
| 8,682,424 B2 | 3/2014 | Tsoglin et al. |
| 8,698,014 B1 | 4/2014 | Walstad |
| 8,858,449 B2 | 10/2014 | Inan et al. |
| 8,870,780 B2 | 10/2014 | Inan et al. |
| 9,011,346 B2 | 4/2015 | Wiard et al. |
| 9,055,871 B2 | 6/2015 | Inan et al. |
| 9,215,991 B2 | 12/2015 | Inan et al. |
| 9,241,637 B2 | 1/2016 | Wiard et al. |
| 2001/0030546 A1 | 10/2001 | Yamada et al. |
| 2001/0044588 A1 | 11/2001 | Mault |
| 2002/0002326 A1 | 1/2002 | Causey, III et al. |
| 2002/0062090 A1 | 5/2002 | Chai et al. |
| 2002/0188205 A1 | 12/2002 | Mills |
| 2003/0050537 A1 | 3/2003 | Wessel |
| 2003/0088196 A1 | 5/2003 | Steve |
| 2003/0126593 A1 | 7/2003 | Mault |
| 2003/0130567 A1 | 7/2003 | Mault et al. |
| 2003/0130595 A1 | 7/2003 | Mault |
| 2003/0149349 A1 | 8/2003 | Jensen |
| 2003/0197614 A1 | 10/2003 | Smith et al. |
| 2003/0233034 A1 | 12/2003 | Varri et al. |
| 2004/0068379 A1 | 4/2004 | Morgan et al. |
| 2004/0073127 A1 | 4/2004 | Istvan et al. |
| 2004/0097802 A1 | 5/2004 | Cohen |
| 2004/0138517 A1 | 7/2004 | Osorio et al. |
| 2004/0211599 A1 | 10/2004 | Kasinoff |
| 2004/0249258 A1 | 12/2004 | Tupin, Jr. et al. |
| 2005/0004483 A1 | 1/2005 | Lin |
| 2005/0017602 A1 | 1/2005 | Arms et al. |
| 2005/0033124 A1 | 2/2005 | Kelly et al. |
| 2005/0043645 A1 | 2/2005 | Ono et al. |
| 2005/0113703 A1 | 5/2005 | Farringdon et al. |
| 2005/0119711 A1 | 6/2005 | Cho et al. |
| 2005/0171451 A1 | 8/2005 | Yeo et al. |
| 2005/0203349 A1 | 9/2005 | Nanikashvili |
| 2005/0206518 A1 | 9/2005 | Welch et al. |
| 2005/0215868 A1 | 9/2005 | Kenjou et al. |
| 2005/0247494 A1 | 11/2005 | Montagnino |
| 2005/0283198 A1 | 12/2005 | Haubrich et al. |
| 2006/0015016 A1* | 1/2006 | Thornton ................. A61B 5/00 600/300 |
| 2006/0049955 A1 | 3/2006 | Blum et al. |
| 2006/0079942 A1 | 4/2006 | Deno et al. |

(56) References Cited

U.S. PATENT DOCUMENTS

| | | |
|---|---|---|
| 2006/0106646 A1 | 5/2006 | Squilla et al. |
| 2006/0111641 A1 | 5/2006 | Manera et al. |
| 2006/0116589 A1 | 6/2006 | Park |
| 2006/0122525 A1 | 6/2006 | Shusterman |
| 2006/0149139 A1 | 7/2006 | Bonmassar et al. |
| 2006/0154642 A1 | 7/2006 | Scannell |
| 2006/0155589 A1 | 7/2006 | Lane et al. |
| 2007/0055324 A1 | 3/2007 | Thompson et al. |
| 2007/0069887 A1 | 3/2007 | Welch et al. |
| 2007/0161913 A1 | 7/2007 | Farrell et al. |
| 2007/0167286 A1 | 7/2007 | Roes |
| 2007/0197878 A1 | 8/2007 | Shklarski |
| 2007/0208232 A1 | 9/2007 | Kovacs |
| 2007/0208233 A1 | 9/2007 | Kovacs |
| 2007/0287928 A1 | 12/2007 | Kiviniemi et al. |
| 2007/0293770 A1 | 12/2007 | Bour et al. |
| 2008/0027679 A1 | 1/2008 | Shklarski |
| 2008/0073128 A1 | 3/2008 | Umemoto |
| 2008/0154645 A1 | 6/2008 | Takehara |
| 2008/0161700 A1 | 7/2008 | Sachanandani et al. |
| 2008/0183090 A1 | 7/2008 | Farringdon |
| 2008/0194975 A1 | 8/2008 | MacQuarrie et al. |
| 2008/0208009 A1 | 8/2008 | Shklarski |
| 2008/0221404 A1 | 9/2008 | Tso |
| 2008/0246629 A1 | 10/2008 | Tsui et al. |
| 2008/0281222 A1 | 11/2008 | Fukada |
| 2008/0306393 A1 | 12/2008 | Ting et al. |
| 2009/0016582 A1 | 1/2009 | Penn et al. |
| 2009/0024044 A1 | 1/2009 | Virtanen et al. |
| 2009/0102296 A1 | 4/2009 | Greene et al. |
| 2009/0182204 A1 | 7/2009 | Semler et al. |
| 2009/0203972 A1 | 8/2009 | Heneghan et al. |
| 2009/0240194 A1 | 9/2009 | Keimel et al. |
| 2009/0284496 A1 | 11/2009 | Oki |
| 2009/0287933 A1 | 11/2009 | Beckwith et al. |
| 2009/0315733 A1 | 12/2009 | Bischoff |
| 2010/0004715 A1 | 1/2010 | Fahey |
| 2010/0016685 A1 | 1/2010 | Muehlsteff et al. |
| 2010/0094147 A1 | 4/2010 | Inan et al. |
| 2010/0174205 A1 | 7/2010 | Wegerif |
| 2010/0210921 A1 | 8/2010 | Park et al. |
| 2010/0262044 A1 | 10/2010 | Siegler |
| 2011/0040352 A1 | 2/2011 | Gerber et al. |
| 2011/0054359 A1 | 3/2011 | Sazonov et al. |
| 2011/0080181 A1 | 4/2011 | Sato et al. |
| 2011/0152695 A1 | 6/2011 | Granqvist et al. |
| 2011/0240379 A1 | 10/2011 | Forshaw et al. |
| 2011/0245710 A1 | 10/2011 | Jensen |
| 2011/0310005 A1 | 12/2011 | Chen |
| 2012/0003933 A1 | 1/2012 | Baker et al. |
| 2012/0065895 A1 | 3/2012 | Saul |
| 2012/0071792 A1 | 3/2012 | Pfeffer et al. |
| 2012/0123219 A1 | 5/2012 | Georgiev et al. |
| 2012/0165622 A1 | 6/2012 | Rodriguez et al. |
| 2012/0245476 A1 | 9/2012 | Skeri et al. |
| 2012/0266250 A1 | 10/2012 | Uhl |
| 2012/0283587 A1 | 11/2012 | Gosh et al. |
| 2012/0302843 A1 | 11/2012 | Otsubo et al. |
| 2012/0318869 A1 | 12/2012 | Edmonds |
| 2013/0006669 A1 | 1/2013 | Nakamura |
| 2013/0056285 A1 | 3/2013 | Meagher |
| 2013/0113506 A1 | 5/2013 | Poupyrev et al. |
| 2013/0226601 A1 | 8/2013 | Razmi et al. |
| 2013/0289889 A1 | 10/2013 | Yuen et al. |
| 2013/0310700 A1 | 11/2013 | Wiard et al. |
| 2014/0089836 A1 | 3/2014 | Damani et al. |
| 2014/0094707 A1 | 4/2014 | Farringdon et al. |
| 2014/0121540 A1 | 5/2014 | Raskin |
| 2014/0142396 A1 | 5/2014 | Ricks et al. |
| 2014/0142437 A1 | 5/2014 | Inan et al. |
| 2014/0172314 A1 | 6/2014 | Baarman et al. |
| 2014/0182952 A1 | 7/2014 | Yuen et al. |
| 2014/0221849 A1 | 8/2014 | Farringdon et al. |
| 2014/0221850 A1 | 8/2014 | Farringdon et al. |
| 2015/0107910 A1 | 4/2015 | Villard et al. |
| 2015/0112209 A1 | 4/2015 | Blaber et al. |
| 2015/0160068 A1 | 6/2015 | Carreel et al. |
| 2015/0168205 A1 | 6/2015 | Lee |
| 2015/0193497 A1 | 7/2015 | Tallamy et al. |
| 2015/0201844 A1 | 7/2015 | Nakagawa |
| 2015/0289802 A1 | 10/2015 | Thomas et al. |
| 2015/0331491 A1 | 11/2015 | Rumreich |
| 2015/0335291 A1 | 11/2015 | Saadi et al. |
| 2015/0338265 A1 | 11/2015 | Carreel et al. |
| 2016/0029905 A1 | 2/2016 | Kovacs |
| 2016/0116326 A1 | 4/2016 | Sharma |
| 2016/0317043 A1 | 11/2016 | Campo et al. |

FOREIGN PATENT DOCUMENTS

| | | |
|---|---|---|
| EP | 0329306 A1 | 2/1989 |
| ES | 2296474 A1 | 4/2008 |
| ES | 2328205 B1 | 8/2010 |
| ES | 2385898 A1 | 8/2012 |
| ES | 2398439 A2 | 3/2013 |
| ES | 2398542 A2 | 3/2013 |
| GB | 2225459 | 5/1990 |
| GB | 2367896 A | 4/2002 |
| JP | 2001198096 | 7/2001 |
| JP | 2001309893 | 11/2001 |
| JP | 2002119488 | 4/2002 |
| JP | 2006212155 | 8/2006 |
| JP | 2007283071 A | 11/2007 |
| JP | 2009050508 A | 3/2009 |
| KR | 0137272 B1 | 4/1998 |
| KR | 100452533 | 10/2004 |
| KR | 20050079235 A | 8/2005 |
| WO | 2005074379 A2 | 8/2005 |
| WO | 2006088280 A1 | 8/2006 |
| WO | 2007103835 | 9/2007 |
| WO | 2008102298 A1 | 8/2008 |
| WO | 2010004502 A1 | 1/2010 |
| WO | WO2010004502 | 1/2010 |
| WO | 2010045455 A1 | 4/2010 |
| WO | 2011075767 A1 | 6/2011 |
| WO | WO2012103296 | 8/2012 |
| WO | 2013017717 A2 | 2/2013 |
| WO | 2013066642 A1 | 5/2013 |
| WO | 2014151133 | 9/2014 |

OTHER PUBLICATIONS

I. Starr and F.C. Wood, "Twenty-Year Studies with the Ballistocardiograph: The Relation Between the Amplitude of the First Record of 'Healthy' Adults and Eventual Mortality and Morbidity from Heart Disease," Circulation, vol. 36, DD. 114-732 (1961).

D.C. Deuchar, S.A. Talbot, and W.R. Scarborough, "Some Observations on the Relation of the High-Frequency Bed Ballistocardiogram to that Obtained from an Aperiodic Bed," Circulation, vol. 11, pp. 228-239 (1955).

H. Mandelbaum and R.A. Mandelbaum, "Studies Utilizing the Portable Electromagnetic Ballistocardiograph: IV. The Clinical Significance of Serial Ballistocardiograms Following Acute Myocardial Infarction," Circulation, vol. 7, pp. 910-9165 (1953).

R.S. Guber, M. Rodstein and H.E. Ungerleider, "Ballistocardiograph: An Appraisal of Technic, Physiological Principles, and Clinic Value," Circulation, vol. 7, DD. 268-286 (1953).

M.B. Rappaport, H.B. Sprague, and W.B. Thompson, "Ballistocardiography: I. Physical Considerations," Circulation, vol. 7, pp. 229-246 (1953).

D. Tannenbaum, J. Schack and H. Vesell, "Relationship between Ballistocardiographic Forces and Certain Events in the Cardiac Cycle," Circulation, vol. 6, DD. 586-592 (1952).

T.E. Satterthwaite, "Cardiovascular Diseases: Recent Advances in Their Anatomy, Physiology, Pathology, Diagnosis and Treatment," Lemcke and Beuschner, New York, NY (1913).

J.W. Gordon, "On Certain Molar Movements of the Human Body Produced by the Circulation of the Blood," J. of Anat. and Phys., vol. 11, DD. 533-536 (1877).

(56) References Cited

OTHER PUBLICATIONS

Gonzalez, et al. "Detection of las frecuencias 1-9 cardiaca and respitatoria mediante una bascu the electronica" In: IFMBE Proceedings. vol. 18, pp. 448-451, 2008. Springer-Verlag Berlin Heidelberg. Abstract Only.
Gomez-Clapers J. et al. "Pulse arrival time estimation from the impedance plethysmogram obtained with a handheld device", 33rd Annual International Conference of the IEEE EMBS, Boston, USA, Mar. 8-9, 2011, pp. 516-519. Abstract only.
HeartForce Medical Inc. "definitions and Terminologies: History of Seismocardiology." www.heartforcemedical.com 4 pages.
Shin et al., "Non-constrained monitoring of systolic blood pressure on a weighing scale", Physiological Measurement, vol. 30, No. 7, pp. 679-693, 2009 Abstract Only.
Pliquett et al., "Front end with offset-free symmetrical current source optimized for time domain impedance spectroscopy", Physiological Measurement, vol. 32, No. 7, 20111 Abstract Only.
Earbud Ballistocardiogram: HeadSense Israel: http://head-sense-med.com/ http://www.medgadget.com/2013/07/headsense-intracranial-pressure-monitoring-earbuds.html.
Bifrostec & The Kaiteki Institute http://www.psfk.com/2013/11/earbud-heart-monitor.html#IzIKRT.
http://www.endgadget.com/2014/01/06/intel-smart-earbuds/.
Mitchell et al., "Arterial Stiffness and Cardiovascular Events the Framingham Heart Study" . Circulation 2010, 121: 505-11.
Blacher et al., "Impact of Aortic Stiffness on Survival in End-Stage Renal Disease" Circulation, 1999: 99.
Blacher et al., "Arterial Calcifications, Arterial Stiffness, and Cardiovascular Risk in End Stage Renal Disease" Hypertension. 38: 938-942 (2001).
Di Micco, et al., "Daily dialysis reduces pulse wave velocity in chronic hemodialysis patients". Hypertension Research. vol. 35, 2012.
Laurent S et al., "Expert consensus document on arterial stiffness: methodological issues and clinical applications", European Heart Journal (2006) 27, 2588-2605.
Boutouyrie P et al., "Assessment of arterial stiffness for clinical and epidemiological studies: methodological considerations for validation and entry into the European Renal and Cardiovascular Medicine registry", Nephrol Dial Transplant (2014) 29: 232-239.
Stewart A D. et al., "Acute Reduction of Blood Pressure by Nitroglycerin Does Not Normalize Large Artery Stiffness in Essential Hypertension", Hypertension 2006, 48: 404-410.
Stewart A D. et al., "Effects of Inhibition of Basal Nitric Oxide Synthesis on Carotid-Femoral Pulse Wave Velocity and Augmentation Index in Humans", Hypertension 2003, 42: 915-918.
Avolio A P., et al., "Effects of aging on changing arterial compliance and left ventricular load in a northern Chinese urban community", Circulation 68, No. 1, 50-58, 1983.
Wilkinson, I B. et al., "ARTERY Society guidelines for validation of non-invasive haemodynamic measurement devices: Part 1, arterial pulse wave velocity" Artery Research (2010) 4, 34-40.
Avolio A P., et al. "Improved Arterial Distensibility in Normotensive Subjuects on a Low Salt Diet", Arteriosclerosis 6: 166-169, 1986.
Balkestein E J., et al., "The effect of weight loss with or without exercise training on large artery compliance in healthy obese men", J. Hypertens 1999, 17: 1831-1835.
Laurent S, et al., "Mesure de la Rigidite Arterielle" Dec. 2013.
Wiard, Richard M., et al. "Preliminary results from standing ballistocardiography measurements in microgravity." 2013 35th Annual International Conference of the IEEE Engineering in Medicine and Biology Society (EMBC). IEEE, 2013. Abstract only.
Inan, Omer T., et al. "Noninvasive measurement of physiological signals on a modified home bathroom scale." IEEE Transactions on Biomedical Engineering 59.8 (2012): 2137-2143. Abstract only.
Giovangrandi, Laurent, et al. "Preliminary results from BCG and ECG measurements in the heart failure clinic." 2012 Annual International Conference of the IEEE Engineering in Medicine and Biology Society. IEEE, 2012. Abstract only.

Park, Dookun, Omer T. Inan, and Laurent Giovangrandi. "A combined heartbeat detector based on individual BCG and IPG heartbeat detectors." 2012 Annual International Conference of the IEEE Engineering in Medicine and Biology Society. IEEE, 2012. Abstract only.
Etemadi, Mozziyar, et al. "Rapid assessment of cardiac contractility on a home bathroom scale." IEEE transactions on Information technology in biomedicine 15.6 (2011): 864-869. Abstract only.
Giovangrandi, L., et al. "Ballistocardiography—a method worth revisiting." Conference proceedings: . . . Annual International Conference of the IEEE Engineering in Medicine and Biology Society. IEEE Engineering in Medicine and Biology Society. Annual Conference. vol. 2011. NIH Public Access, 2010.
Inan, Omer T., et al. "Multi-signal electromechanical cardiovascular monitoring on a modified home bathroom scale." 2011 Annual International Conference of the IEEE Engineering in Medicine and Biology Society. IEEE, 2011. Abstract only.
Wiard, R. M., et al. "Estimation of central aortic forces in the ballistocardiogram under rest and exercise conditions." Conference proceedings: . . . Annual International Conference of the IEEE Engineering in Medicine and Biology Society. IEEE Engineering in Medicine and Biology Society. Annual Conference. vol. 2009. NIH Public Access, 2008.
Etemadi, Mozziyar, et al. "Non-invasive assessment of cardiac contractility on a weighing scale." 2009 Annual International Conference of the IEEE Engineering in Medicine and Biology Society. IEEE, 2009. Abstract only.
Inan, Omer T., et al. "Non-invasive measurement of valsalva-induced hemodynamic changes on a bathroom scale ballistocardiograph." 2008 30th Annual International Conference of the IEEE Engineering in Medicine and Biology Society. IEEE, 2008. Abstract only.
Inan, Omer T., et al. "Unobtrusive Monitoring of Cardiovascular Health at Home Using a Modified Weighing Scale." 6th European Conference of the International Federation for Medical and Biological Engineering. Springer International Publishing, 2015. Abstract only.
McCall, Corey, et al. "Standing ballistocardiography measurements in microgravity." 2014 36th Annual International Conference of the IEEE Engineering in Medicine and Biology Society. IEEE, 2014. Abstract only.
Inan, Omer Tolga. Novel technologies for cardiovascular monitoring using ballistocardiography and electrocardiography. Dissertation Abstracts International, vol. 70. No. 10. 2009. Abstract only.
Wiard, Richard Matthew. Validation of Non-invasive Standing Arterial Stiffness Measurements Using Ballistocardriography and Photoplethysmography. 2012. Abstract only.
European Patent Office, Third Examination Report dated Nov. 26, 2014 for EPO Patent Application No. 07757854.0. which claims priority from PCT Application No. PCT/US2007/063244.
China State Intellectual Property Office, Office Action dated Oct. 13, 2010 for CN Patent Application No. 200780015788.1.
Japan Patent Office, Notice of Reasons for Rejection dispatched Mar. 6, 2012 for JPO Patent Application No. 32008-558484. which claims priority from PCT Application No. PCT/US2007/063244; Reference 1 cited in the Notice of Reaons for Rejection corresponds to U.S. Appl. No. 08/555,546, issued as U.S. Pat. No. 5701894, Cherry et al., which is cited above; Reference 2, US 20030050537, Wessel, is cited above.
European Patent Office, Extended European Search Report dated Feb. 12, 2010 for EPO Application No. 07757854.0.
International Search Report and Written Opinion of the International Searching Authority for PCT International App. No. PCT/US07/63244.
Discera, "Shrinking Wireless Architectures", available for download from www.discera.com prior to Mar. 3, 2006.
GeTeMed GmbH, "Baby Monitoring System Vitaguard VG3000", Teltow, Germany, 1997-1999, available at http://www.fuse-network.com/fuse/demonstration/331/24571.pdf.
ATMEL, "Microcontroller with 16 K Bytes In-System Programmable Flash", Atmel Atmega, document contains notation AVR 06/05.

(56) References Cited

OTHER PUBLICATIONS

Kaminska, Wireless Wearable Biomonitors for Lifetime Wellness Optimization, Proceedings of the 3rd Annual International IEEE EMBS Special Topic Conference on Microtechnologies in Medicine and Biology, Kahuku, Oahu, Hawaii, May 2005. Abstract Only.
NorthEast Monitoring Inc., "Hotter LX Pro Software—Operator's Manual", NorthEast Monitoring Inc. Two Clock Tower Suite 360 Maynard Massachusetts 01754, Apr. 2003.
Nguyen et al., "Transceiver Front-End Architectures Using Vibrating Micromechanical Signal Processors", Dig. of Papers, Topical Meeting on Silicon Monolithic Integrated Circuits in RF Systems: 23-32, Sep. 4, 2001.
ANSI/AAMI, EC11:1991/(R) 2001, Diagnostic Electrogardiographic Devices, 2000.
ANSI/MM I, EC38: 1998, Ambulatory Electrocardiographs, 1999.
Nguyen et al., "Frequency-Selective MEMS for Miniaturized Low-Power Communication Devices", IEEE Trans. Microwave Theory Tech 47(8):1486-1503, Aug. 1999.
Nguyen et al., "An Integrated CMOS Micromechanical Resonator High-Q Oscillator", IEEE Journal of Solid-State Circuits 34(4), Apr. 1999.
Nguyen et al., "Micromachined Devices for Wireless Communications," Proc. IEEE 86(8):1756-1768, Aug. 1998.
Kovacs, "Micromachined Transducers-Sourcebook", McGraw-Hill, New York, New York, 1998 944 page book.
Desel et al., "A CMOS Nine Channel ECG Measurement IC", ASIC 1996 2nd International Conference: 115-118, Oct. 1996 Abstract Only.
Fraunhofer, "Medical Technolology", http://www.iis.fraunhofer.de/en/ff/med.html Dec. 26, 2005.
Toumaz "Technology", Nov. 8, 2005.
Kaminiski, "Wearable Biomonitors With Wireless Network Communication" draft of paper published in Proceedings of the 3rd Annual International IEEE EMBS Special Topic Conference on Microtechnologies in Medicine and Biology, Kahuku, Oahu, Hawaii, May 2005.
Novosense AB, "Company", Apr. 4, 2005.
IMEC, "Sensor Electronics", available for download at http://www.imec be/wwwinter/mediacenter/en/SR2004/scientificreport/competencies/c14/sr101_cont.html, Mar. 31, 2005.
NOVOSENSE, AB, "Technology", available for download at http://www.novosense.se/technology.html Aug. 5, 2015.
Miromico AG, "Sample Projects", available for download at http://www.miromico.ch/index.php?sec-ad.sa&lang=2, page includes notice of Copyright 2005 Miromico.
Mori, Narumi, et al. "Clinical assessment of a new method for pacing pulse detection using a hybrid circuit in digital Holter monitoring." Japanese circulation journal 64.8 (2000): 583-589.
Pyron, "Pyron Introduces ECG ASIC Monitoring Subsystem", Electronic News, Nov. 29, 1999, available for download at http://www.end.com/article/CA52794.html.
Nguyen, Clark T-C., and Roger T. Howe. "An integrated CMOS micromechanical resonator high-Q oscillator." Solid-State Circuits, IEEE Journal of 34.4 (1999): 440-455.
Grossbach, Wolfgang. "Measuring the ECG Signal with a Mixed Analog-Digital Application-Specific IC." Hewlett-Packard Journal 42.4 (1991): 21-24. Abstract Only.
J. Alametsä et al. "Ballistocardiogaphic studies with acceleration and electromechanical film sensors." Medical Engineenng & Physics 31 (2009), p. 1154-1165.
J. Alametsä et al. "Arterial Elasticity Measurements with Ankle Pulse Width Velocity and Ballistocardiography." ECIFMBE 2008, IFMBE Proceedings 22, p. 1636-1641.
J. Allen. "Photoplethysmography and its application in clinical physiological measurement." Physiol. Meas. 28, 2007, p. R1-R39.
A. Avolio et al. "Role of Pulse Pressure Amplification | Arterial Hpertension: Experts' Opinion and Review of the Data." Hypertension, vol. 54, Aug. 1, 2009, p. 375-383.

J. Blacher et al. "Aortic Pulse Wave Velocity as a Marker of Cardiovascular Risk in Hypertensive Patients," Hypertension, vol. 33, 1999, p. 1111-1117.
Davis, S; B. van den Bogaard et al. "Active standing reduces wave reflection in the presence of increased peripheral resistance in young and old healthy individuals." J Hypertension (4) Apr. 29, 2011, p. 682-689 (Abstract); and B. van den Bogaard. "Chapter 12: Active standing reduces wave reflection in the presence of increased peripheral resistance in young and old healthy individuals." Dissertation, Univ. Amsterdam, 2012, p. 180-193.
G. Kim et al. "Vascular Variation of PTT and the Vascular Characteristic Index According to the Posture Change." In Proceedings of the 2007 International Conference on Convergence Information Technology (ICCIT '07). IEEE Computer Society, Nov. 2007, p. 2426-2425. Abstract Only.
E. Pinheiro et al. "Non-Intrusive Device for Real-Time Circulatory System Assessment with Advanced Signal Processing Capabilities." Measurement Science Review, vol. 10, No. 5, 2010, p. 167-175.
E. Pinheiro et al. "Pulse arrival time and ballistocardiogram application to blood pressure variability estimation." Medical Measurements and Applications, 2009. IEEE Workshop, May 29-30, 2009. Abstract only.
M. Safar "Arterial aging—hemodynamic changes and therapeutic options." Nat Rev Cardiol, vol. 7, 207, p. 442-449. Abstract / Introduction Only.
R. Wiard et al. "Estimation of Central Aortic Forces in the Ballistocardiogram under Rest and Exercise Conditions." 31st Annual International Conference of the IEEE EMBS, Sep. 2-6, 2009, p. 2831-2834.
R. Wiard et al. "Automatic detection of motion artifacts in the ballistocardiogram measured on a modified bathroom scale." Med Biol Eng Comput (2011) 49:213-220. Published online Dec. 9, 2010.
B. Williams et al. "Differential Impact of Blood Pressure-Lowering Drugs on Central Aortic Pressure and Clinical Outcomes: Principal Results of the Conduit Artery Function Evaluation (CAFE) Study," Circulation, vol. 113, Feb. 13, 2006, p. 1213-1225.
O.T. Inan, M. Etemadi, R.M. Wiard, L. Giovangrandi, and G. T. A. Kovacs, "Robust Ballistocardiogram Acquisition for Home Monitoring," Phys. Meas., vol. 30, No. 2, pp. 169-185 (2009).
Inan OT, Etemadi M, Paloma A, Giovangrandi L, Kovacs GTA (2009) Non-invasive cardiac output trending during exercise recovery on a bathroom-scale-based ballistocardiograph. Physiol Meas 30:261-274 Abstract / Introduction Only.
Inan OT, Etemadi M, Wiard RM, Kovacs GTA, Giovangrandi L (2009) Novel methods for estimating the ballistocardiogram signal using a simultaneously acquired electrocardiogram. In: 31st annual IEEE engineers in medicine and biology conference. IEEE, Minneapolis, MN Abstract / Introduction Only.
Inan OT, Kovacs GTA, Giovangrandi L (2010) Evaluating the lower-body electromyogram signal acquired from the feet as a noise reference for standing ballistocardiogram measurements. IEEE Trans Inf Technol Biomed 14:1188-1196 Abstract / Introduction Only.
DeLoach SS, Twonsend RR, "Vascular Stiffness: Its Measurement and Significance for Epidemiologic and Outcome Studies", Clin J Am Soc Nephrol, 3: 184-192, 2008. Abstract / Introduction Only.
Webster's Ninth New Collegiate Dictionary, Meriam-Webster Inc., 1990, p. 1152.
Alan Fang et al., "Using a Geophone for Vibration Cancellation in a STM," abstract, Bulletin of the American Physical Society, 2008 APS March Meeting, vol. 53, No. 2, Mar. 10, 2008.
de Viries, S. O. et al., "Prediction of the Left Ventricular Mass from the Electrogram in Systemic Hypertension," American Journal of Cardiology, May 1, 1996;777(11):974-8. (Abstract Only).
A.Akhbardeh, M. Koivuluoma, T. Koivistoinen and A. Varri, "Ballistocardiogram Diagnosis Using Neural Networks and Shift-Invariant Daubechies Wavelet Transform," Researchers at Institute of Signal Processing, Tampere University ofTechnololgy, Tampere 33101, Finland.
O. Inan, et al.,"Evaluating the Foot Electromyogram Signal as a Noise Reference for a Bathroom Scale Ballistocardiogram Recorder," Stanford University, Department of EE, Department of Bioengineering.

(56) References Cited

OTHER PUBLICATIONS

D. Inan and Kovacs, "An 11 µW, Two-Electrode Transimpedance Biosignal Amplifier with Active Current Feedback Stabilization," IEEE Transactions on Biomedical Circuits and Systems (2009).

O. Inan, M. Etemadi, B. Widrow and G. Kovacs, "Adaptive cancellation of floor vibrations in standing ballistocardiogram measurements using a seismic sensor as a noise reference," IEEE (2009).

R. F. F Yazicioglu, P. Merken, R. Puers and C. Van Hoof, "A 60 µW 60 nV/..JHz Readout Front-End for Portable Biopotential Acquisition Systems," IEEE Journ. of Solid-State Circuits, vol. 42, No. 5 (May 2007).

W. Rosamond et al., "Heart Disease and Stroke Statistics—2007 Update: A Report from the American Heart Association Statistics Committee and Stroke Statistics Subcommittee," Circ., v. 115, pp. 69-171 (2007).

R. R. Harrison, "A Versatile Integrated Circuit for the Acquisition of Biopotentials," IEEE CICC, pp. 115-122 (2007).

T. Denison, K. Consoer, W. Santa, A.-T. Avestruz, J. Cooley, and A. Kelly, "A 2µW J00 nV/rtHz, Chopper-Stabilized Instrumentation Amplifier for Chronic Measurement of Neural Field Potentials," IEEE Jour. Solid-State Circuits, v. 42, No. 12, DD. 2934-2945 (2007).

A.Akhbardeh, S. Junnila, M. Koivuluoma, T. Koivistoinen, V. Turjanmaa, T. Koobi, and A. Viirri, "Towards a heart disease diagnosing system based on force sensitive chair's measurement, biorthogonal wavelets and neural networks," ScienceDirect, Engineering Applications for Artificial Intelligence, pp. 1-10 (2006).

D. Corrado, C. Basso, A. Pavel, P. Michieli, M. Schiavon, and G. Thiene, "Trends in Sudden Cardiovascular Death in Young Competitive Athletes After Implementation of a Preparticipation Screening Program," JAMA, vol. 296, No. 13, pp. 1593-1601 (Oct. 4, 2006).

V.N. Chien and F.S. Jaw, "Miniature ultra-low-power biopotential amplifier for potable [sic} applications," Biomedical Engineenng-Applications, Basis & Communications, vol. 17, No. 2, pp. 11-49 (Apr. 2005).

C.W. Mundt, K.N. Montgomery, U.E. Udoh, V.N. Barker, G.C. Thonier, A.M. Tellier, R.D. Ricks, R.B. Darling, Y.D. Cagle, N.A. Cabrol, S.J. Ruoss, J.L. Swain, J.W. Hines, and G.T.A. Kovacs, "A Multiparameter Nearable Physiologic Monitoring System for Space and Terrestrial Applications," IEEE Trans. Inform. Tech. in Biomed., vol. 9, No. 3, pp. 382-391 (Sep. 2005).

M. Shojaei-Baghini, R.K. Lal, and D.K. Sharma, "A Low-Power and Compact Analog CMOS Processing Chip for Portable ECG Recorders," Proc. IEEE A.S.S.C.C., DD. 473-476 (2005).

J. Alametsii, A. Viirri, M. Koivuluoma, and L. Barna, "The Potential of EMFi Sensors in Heart Activity Monitoring," 2nd OpenECG Workshop "Integration of the ECG into the EHR & Interoperability of ECG Device Systems," Apr. 1-3, 2004 Berlin, Germany.

E. Company-Bosch and E. Hartmann, "ECG Front-End Design is Simplified with MicroConverter," Analog Dialogue, 37-11, pp. 1-5 (Nov. 2003).

D.M. Linton and u. Giion, "Advances in noninvasive cardiac output monitoring," Annals of cardiac Anaesthesia, vol. 5, pp. 141-148 (2002).

M. Watanabe, J. Marine, R. Sheldon, and 1\1. Josephson, "Effects of Ventricular Premature Stimulus Coupling Interval on Blood Pressure and Heart Rate Turbulence," Circ., vol. 106, pp. 325-330 (2002).

K. Lu, J. W. Clark, Jr. F. H. Ghorbel, D. L. Ware, and A. Bidani, "A human cardiopulmonary system model applied to the analysis of the Valsalva maneuver," Am. J Physiol. Heart Circ. Physiol., vol. 281, pp. H2661-H2679 (2001).

J. Rapoport, D. Teres, J. Steingrub, T. Higgins, W. McGee, and S. Lemeshow, "Patient characteristics and ICU organizational factors that influence frequency of pulmonary artery catheterization," JAMA, vol. 283, No. 19, pp. 2559-2567 (2000).

B.D. Johnson, K.C. Beck, D.N. Proctor, J. Miller, N.M. Dietz, and M.J. Joyner, "Cardiac output during exercise by the open circuit acetylene washin method: comparison with direct Fick," J. Appl Physiol, vol. 88, pp. 1650-1658 (2000).

W. Klimesch, "EEG alpha and theta oscillations reflect cognitive and memory performance: a review and analysis," Brain Research Reviews, vol. 29, DD. 169-195 (1999).

D. Corrado, C. Basso, M. Schiavon, and G. Thiene, "Screening for Hypertrophic Cardiomyopathy in Young Athletes," NEJM, vol. 339, pp. 364-369 (Aug. 6, 1998).

A.C. MettingVanRijn, A. Peper and C.A. Grimbergen, "Amplifiers for bioelectric events: a design with a minimal number of parts," Med. & Biol. Eng. & Comput., vol. 32, DD. 305-310 (1994).

R. Moore, R. Sansores, V. Guimond, and R. Abboud, "Evaluation of cardiac output by thoracic electrical bioimpedance during exercise in normal subjects," American College of Chest Physicans, vol. 102, DD. 448-455 (1992).

J. Christie, L.M. Sheldahl, F.E. Tristani, K.B. Sagar, M.J. Ptacin, and S. Wann, "Determination of stroke volume and cardiac output during exercise: comparison of two-dimensional and Doppler echocardiography, Fick oximetry, and thermodilution," Circ., vol. 76, DD. 539-547 (1987).

H. Benjelloun, R. Itti, L. Philippe, J.M. Lorgeron and M. Brochier, "Beat-to-Beat Assessment of Left Ventricular Ejection in Atrial Fibrillation," European Journal Nuclear Medicine, vol. 8, pp. 206-210 (1983).

S. Grimnes, "Impedance measurement of individual skin surface electrodes," Med. & Biol. Eng. & Comput., vol. 21, DD. 750-755 (1983).

Y. Miyamoto, M. Takahashi, T. Tamura, T. Nakamura, T. Hiura, and M. Mikami, "Continuous determination of cardiac output during exercise by the use of impedance plethysmogrphy," Med. Biol. Eng. Comp., vol. 19, DD. 638-644, (1981).

R.P. Lewis, S.E. Rittogers, W.F. Froester, and H. Boudoulas, "A critical review of the systolic time intervals," Circulation, vol. 56, DD. 146-158 (1977).

\* cited by examiner

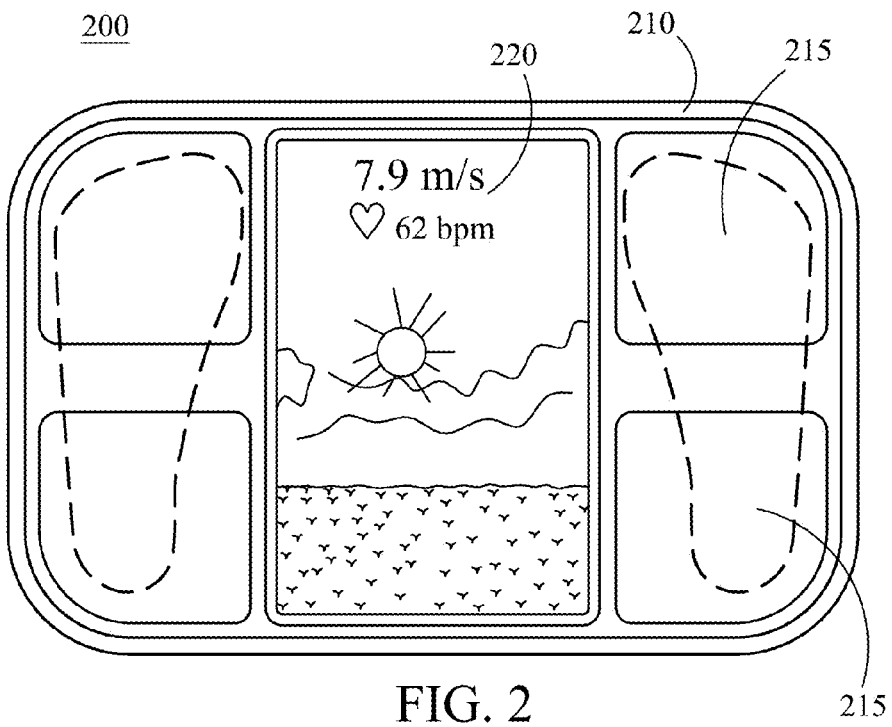
FIG. 2
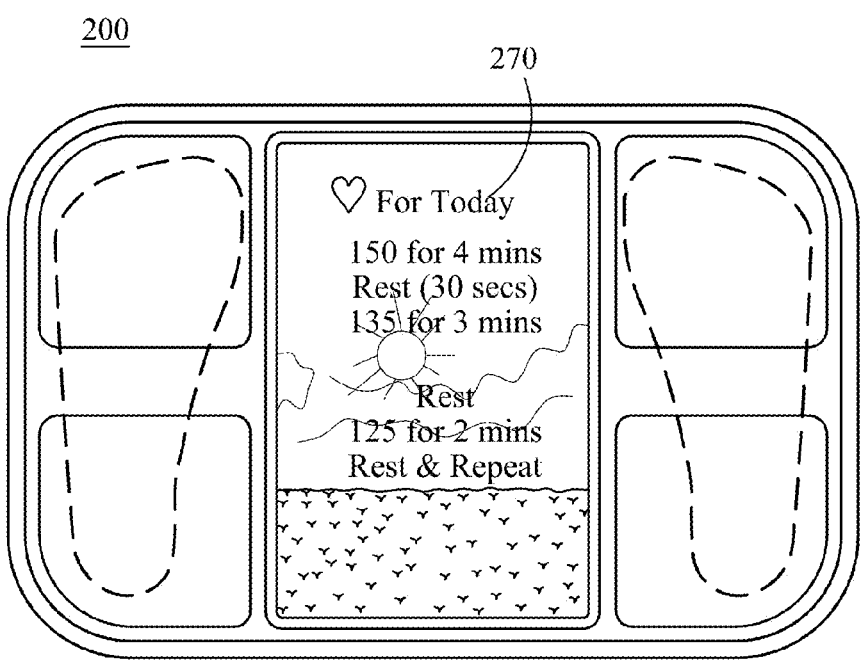
FIG. 2-i

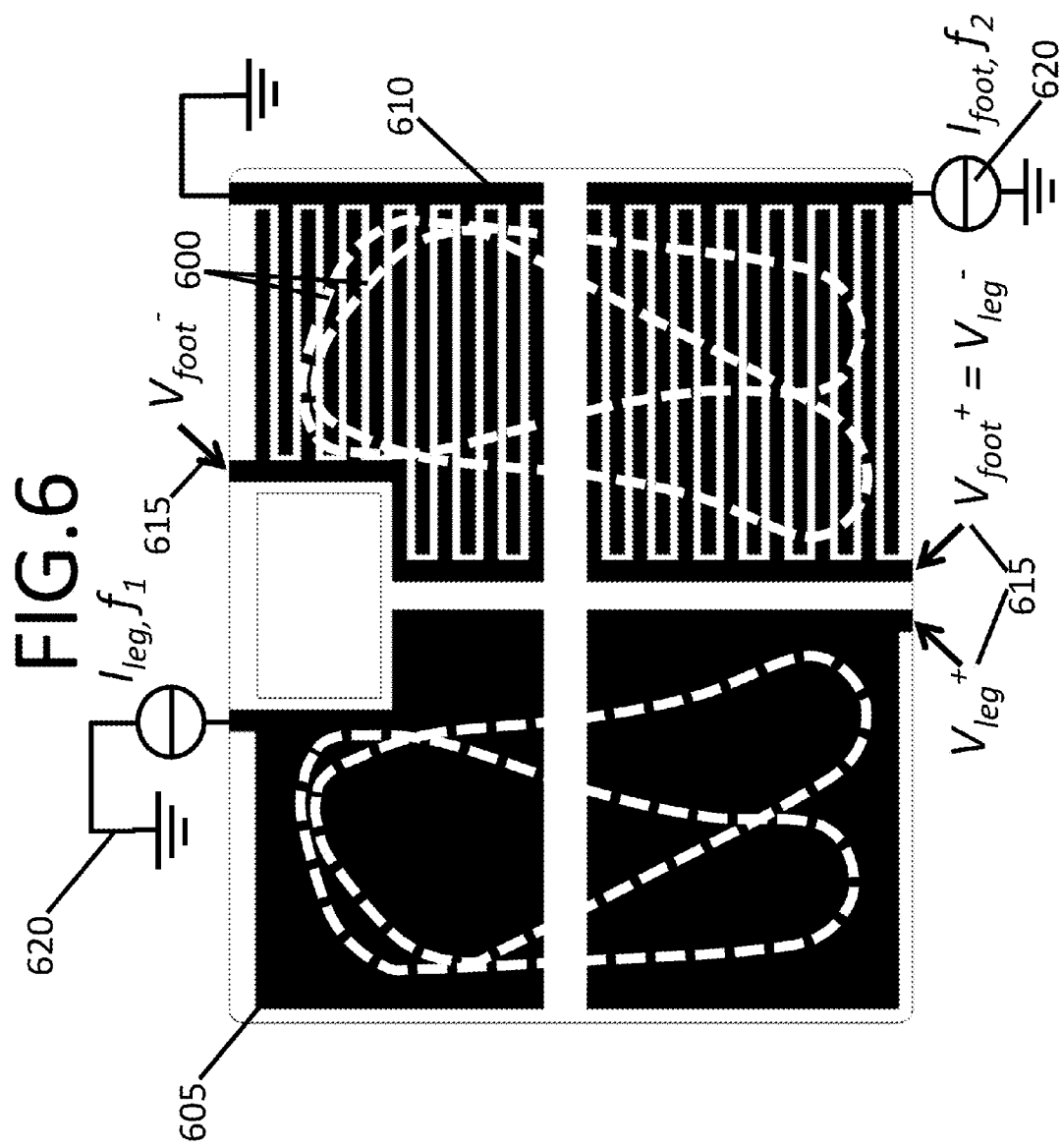

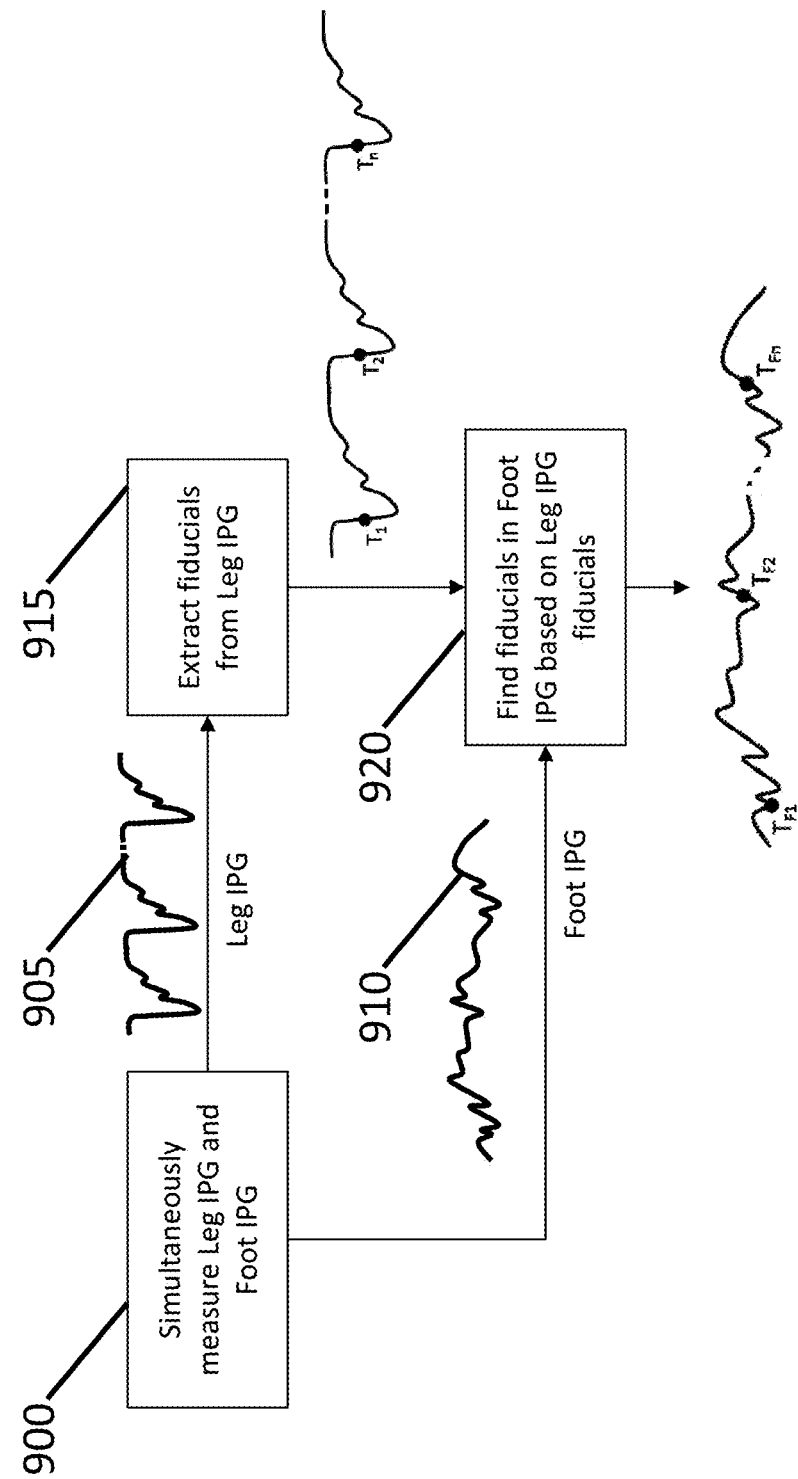

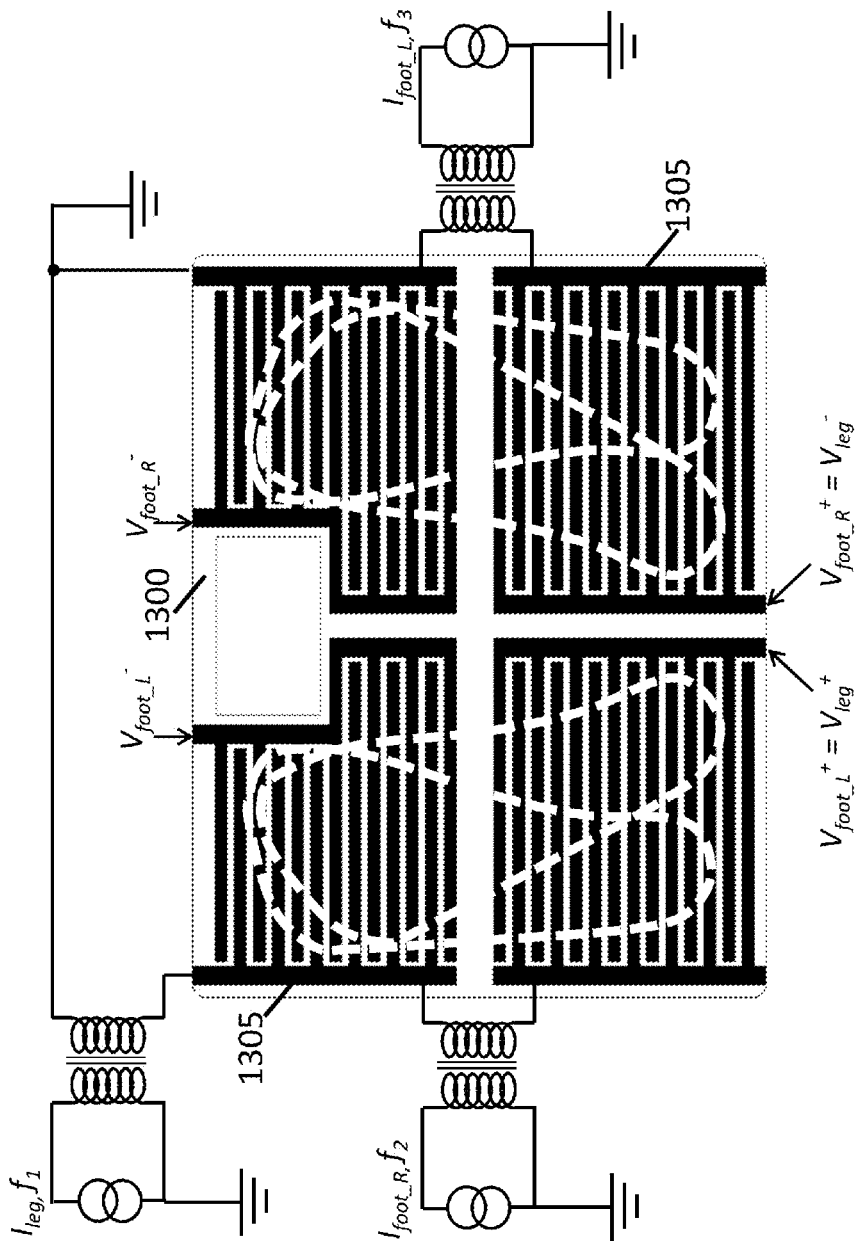

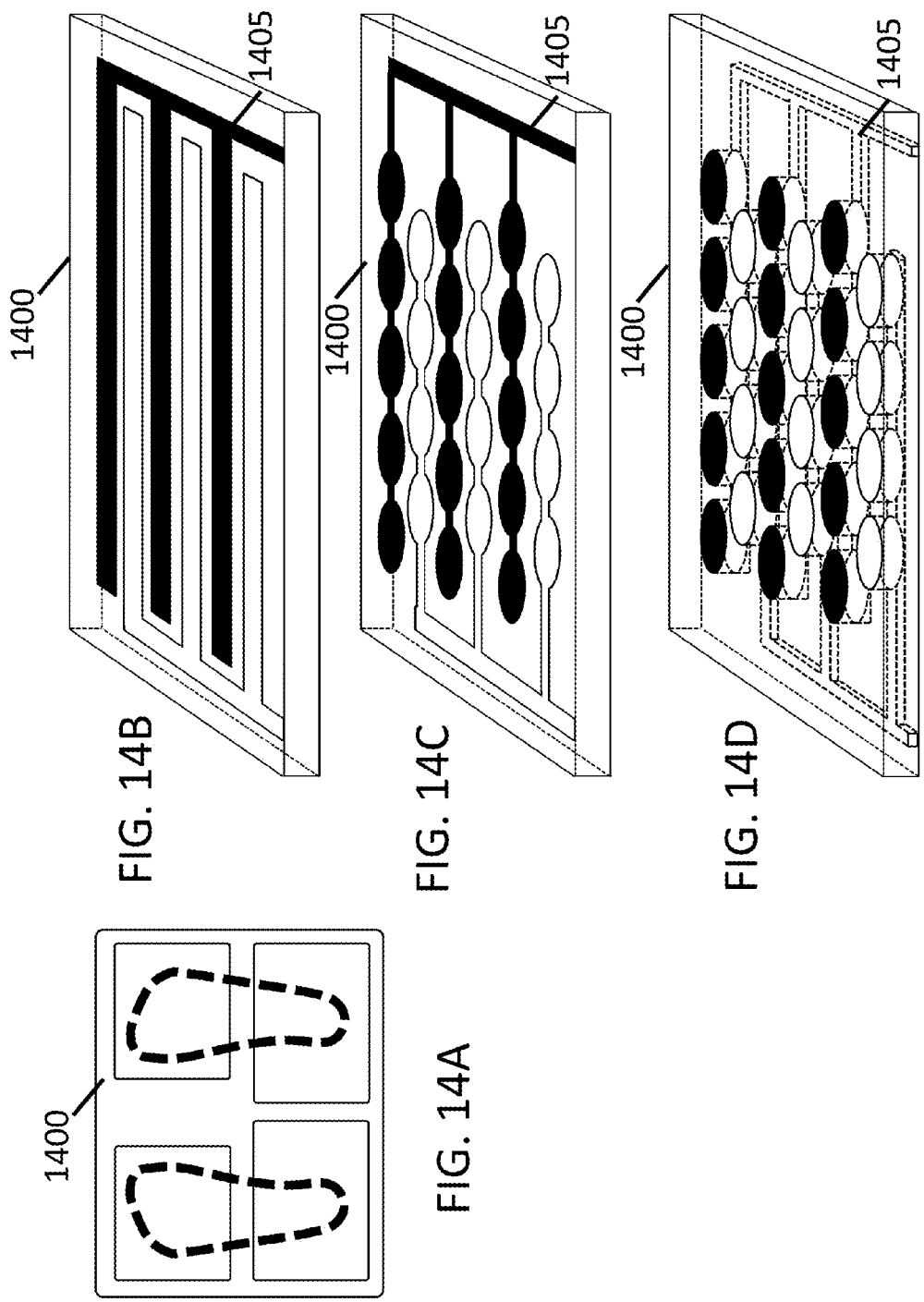

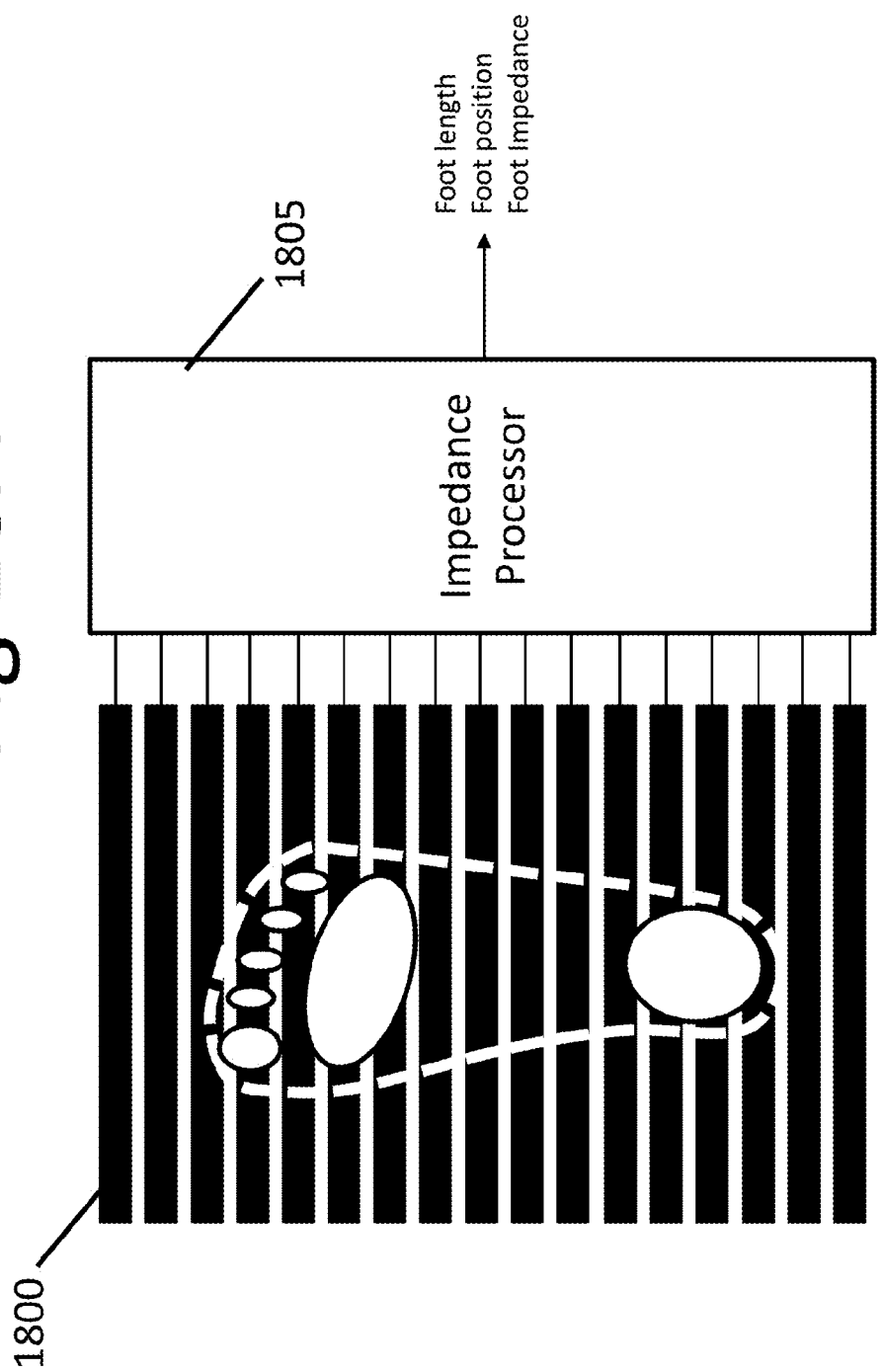

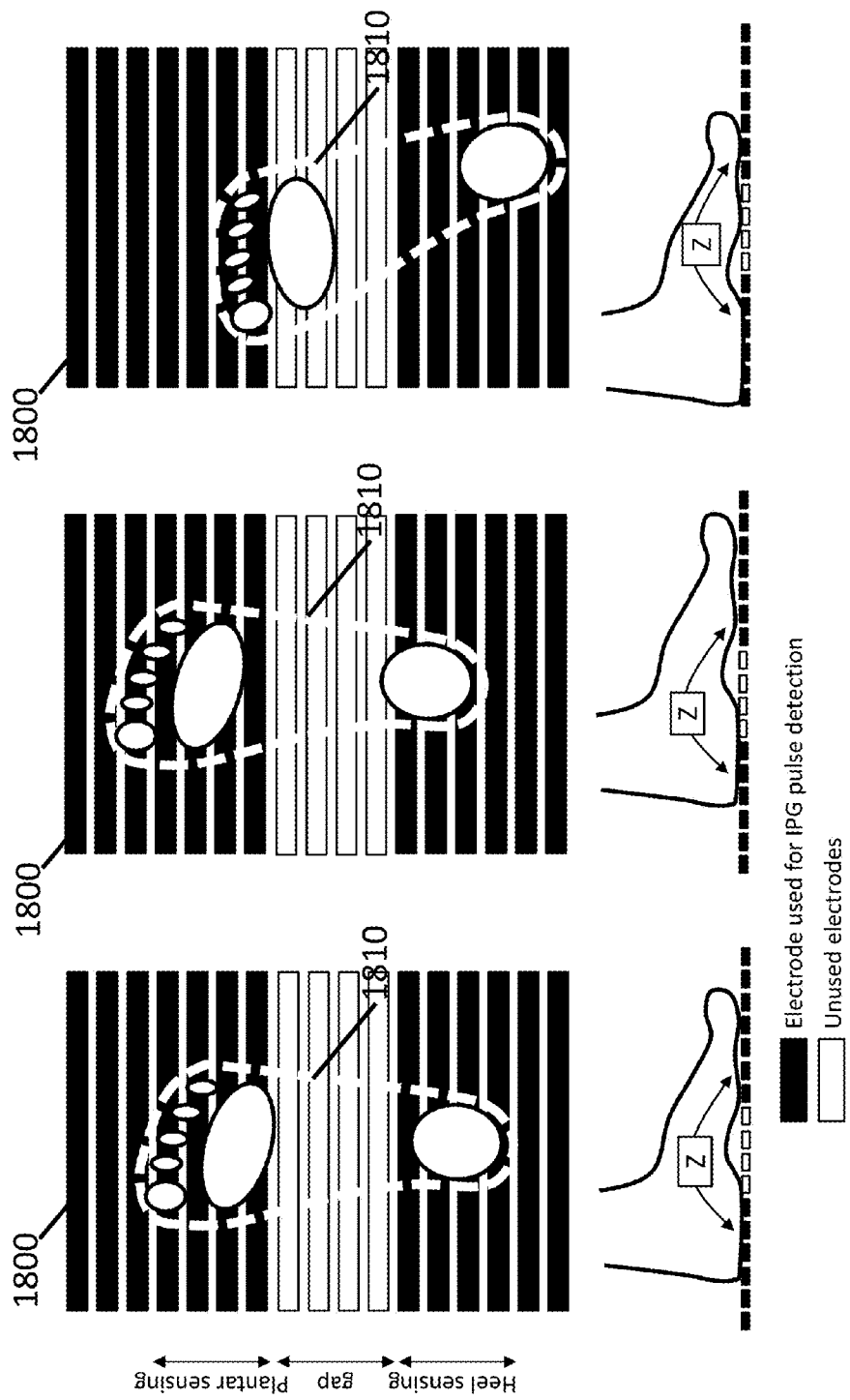

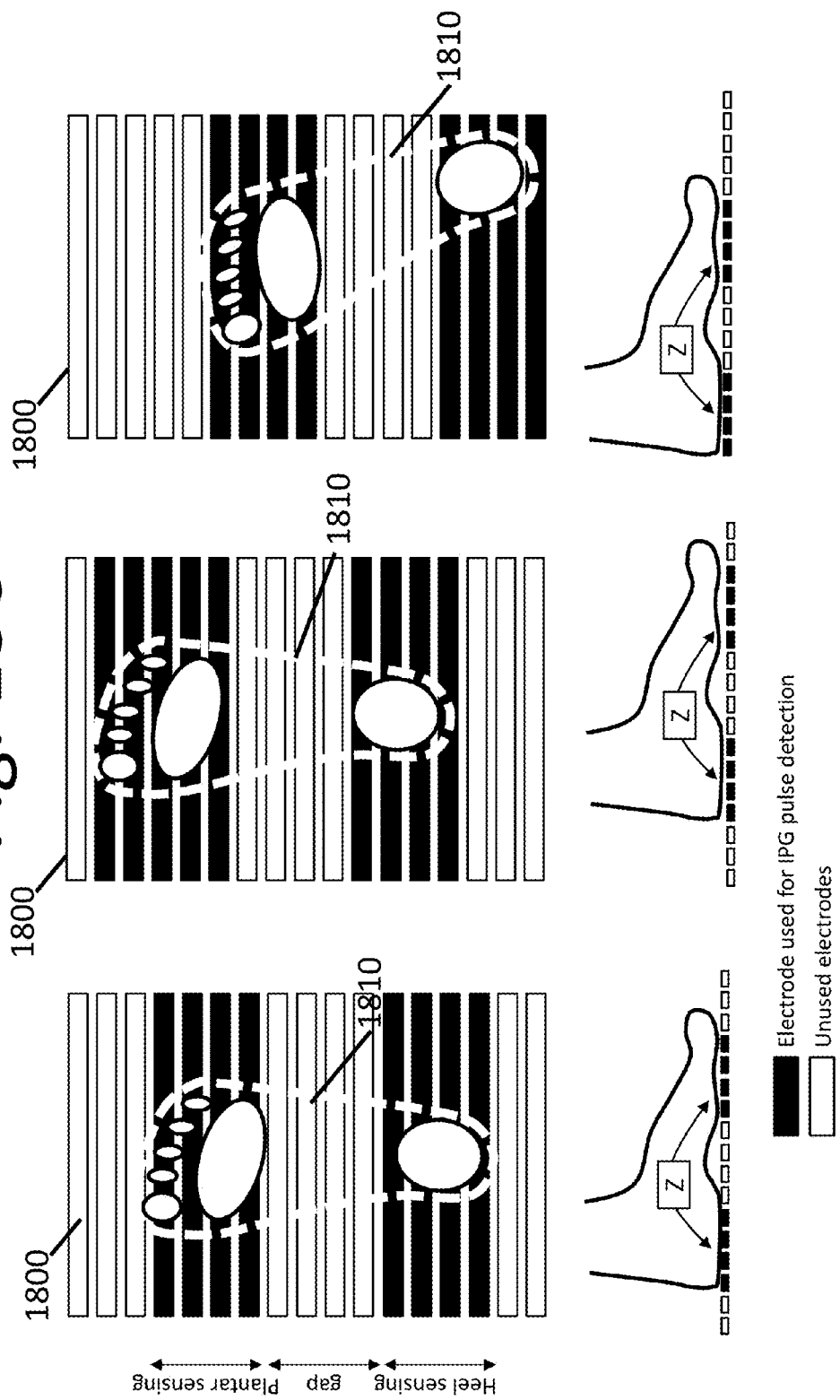

PHYSIOLOGICAL ASSESSMENT SCALE

The present invention is believed to be useful for a variety of physiological assessments, and has been found to be particularly beneficial when used in the context of fitness testing wherein the physiological assessment is fitness testing. Such embodiments may, for example, involve interacting with a user at one or more exertion conditions, and therefrom obtaining physiological characteristics of the user. These characteristics are provided or otherwise used to ascertain one or more fitness conditions associated with the user. For instance, by obtaining or using baseline type characteristics pertaining to a non-exertion or resting state (e.g., at resting heart rate), physiological characteristics that are later obtained from the user while the user's heart rate is elevated (at a state of exertion) can be used with the baseline type characteristics to generally characterize the user's fitness.

One specific aspect of the present disclosure relate to a weighing scale including a platform region for supporting a user while the user stands on the platform region, circuitry configured and arranged to be integrated with a display and a support structure, a display configured and arranged with the support structure for displaying data through the platform region, and a support structure including the platform region and sensor circuitry therein. The platform region is configured to engage the user with the sensor circuitry while the user stands on the platform region and to collect physiological data from the user via the sensor circuitry. The display and the circuitry are configured to operate in a physiological assessment mode by instructing a user to engage the sensor circuitry via the platform region for measuring parameters of the user relative to baseline user measurements, to cause change to the user's heart rate by increasing or decreasing physical exertion, and thereafter, upon recognizing that the user has returned to the support structure, to engage the sensor circuitry via the platform region and collect and collate user physiological data.

Additional aspects of the present disclosure relate to electronic body platforms and/or scales that weigh the user and/or provide impedance-based biometric measurements, as may be implemented with physiological-assessment based approaches as discussed above or otherwise herein.

Biometrics is a broad term wherein this application includes the measurements of body composition and cardiovascular information. Impedance measurements can be made through the feet to measure fat percentage, muscle mass percentage, and body water percentage. Additionally, foot-impedance-based cardiovascular measurements can be made for an electrocardiogram (ECG) and sensing the properties of blood pulsations in the arteries, also known as impedance plethysmography (IPG), where both techniques can be used to quantify heart rate and/or pulse arrival timings (PAT). Cardiovascular IPG measures the change in impedance through the corresponding arteries between the sensing electrode pair segments synchronous to each heartbeat. One or more of these aspects may be implemented to provide fitness-based characterizations.

In some embodiments of the present disclosure, a weighing scale is disclosed that includes a support structure, a display, circuitry, and a communication driver, and operates for providing physiological-based characterization via the circuitry. The support structure has a platform region with sensor circuitry and which engages a user via the sensor circuitry while the user stands on the platform region. The sensor circuitry collects physiological data from the user such as measurements of body composition and cardiovascular information which are then forwarded on to the circuitry for analysis. The display displays data through and throughout the entire platform region, including entertainment information, and physiological parameters of the user as determined by the circuitry.

The circuitry operates in a physiological-assessment mode, such as a fitness testing mode, by instructing a user to engage the sensor circuitry on the platform region of the weighing scale, during a reduced-exertion state of the user, thereby allowing the sensor circuitry to collect physiological data from the user. The circuitry also instructs the user to raise his or her exertion level by exercising, and to again engage the sensor circuitry on the platform region of the weighing scale, immediately after physical exertion. The respectively-collected sets of physiological data may be collected in any order, such as by first collecting data in a reduced-exertion or resting state and later collecting data in an exerted state, or by first collecting data in an exerted state and later collecting data at a predetermined time after collecting the data in the exerted state.

The sensor circuitry thus collects physiological data from the user indicative of a physical exertion state of the user under different conditions. The circuitry receives the physiological data from the sensor circuitry (including both the physiological data indicative of the reduced-exertion state and a higher exertion state), and determines physiological parameters of the user based on the physiological data and the associated physical state. The communication driver receives the information (including the determined physiological parameters) from the circuitry and provides the information to the display for viewing by the user through the platform region. Accordingly, the displayed physiological data can provide the user with indications as to their level of cardio-health, physical fitness, and/or indication of a physiological condition.

In some embodiments, the weighing scale also includes a data-access circuit that provides access to user-specific data. Such user-specific data may include, for example, physiological parameters of the user that are stored in response to or developed by the user-targeted circuitry.

Various example embodiments may be more completely understood in consideration of the following detailed description in connection with the accompanying drawings, in which.

Figure 4:
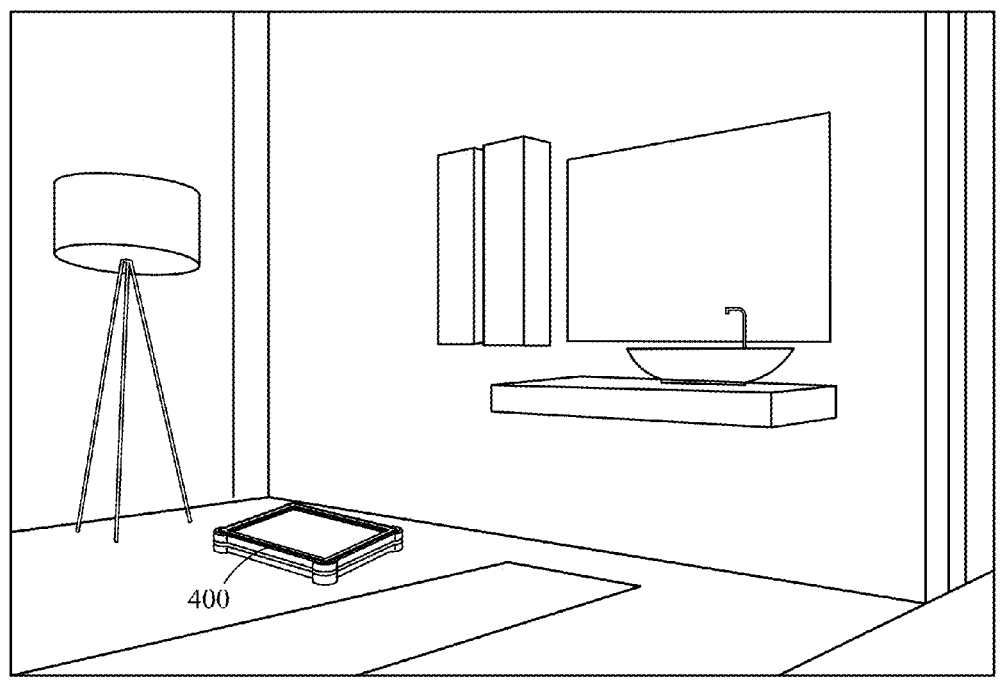
Figure 5A:
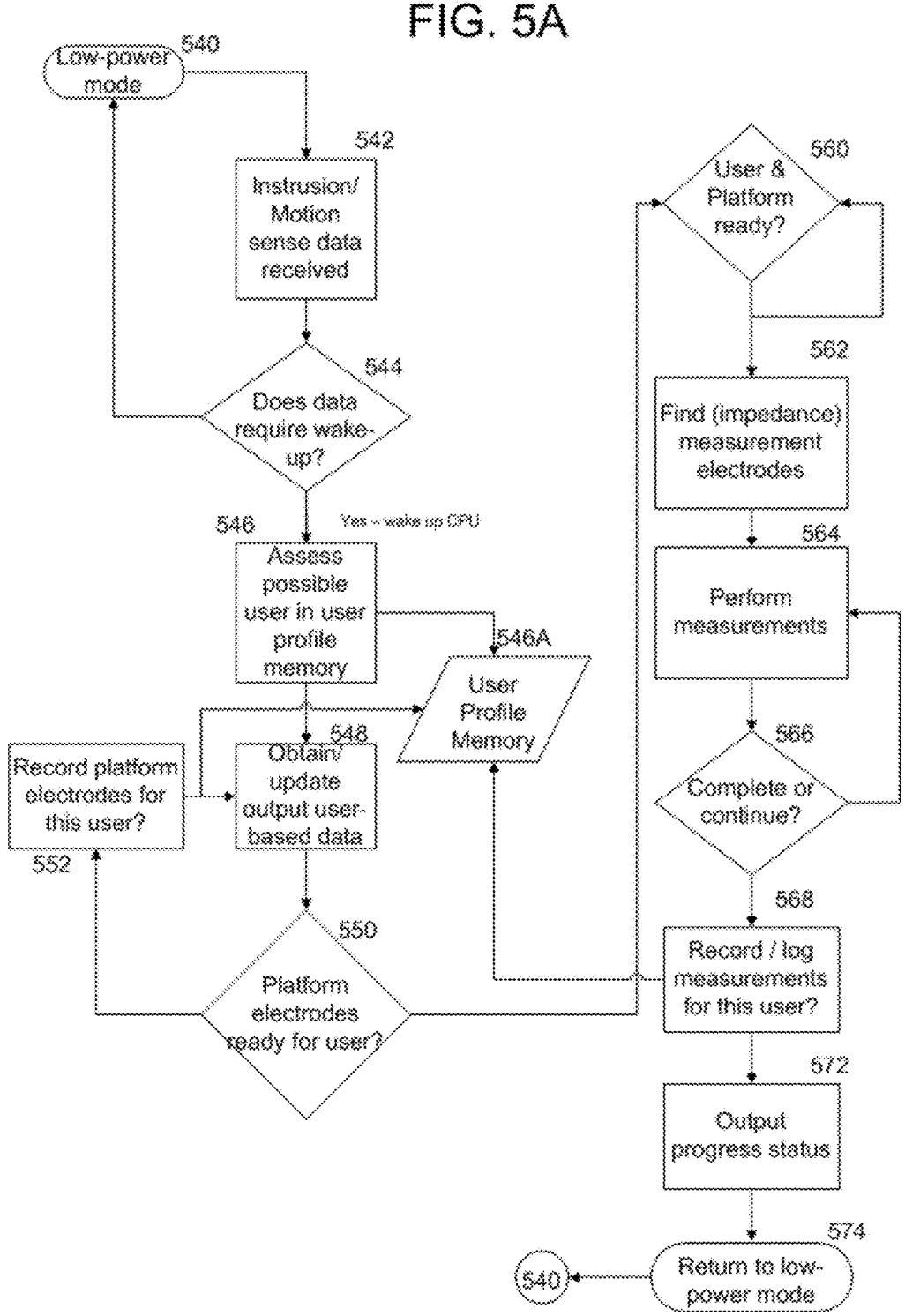
Figure 5B:
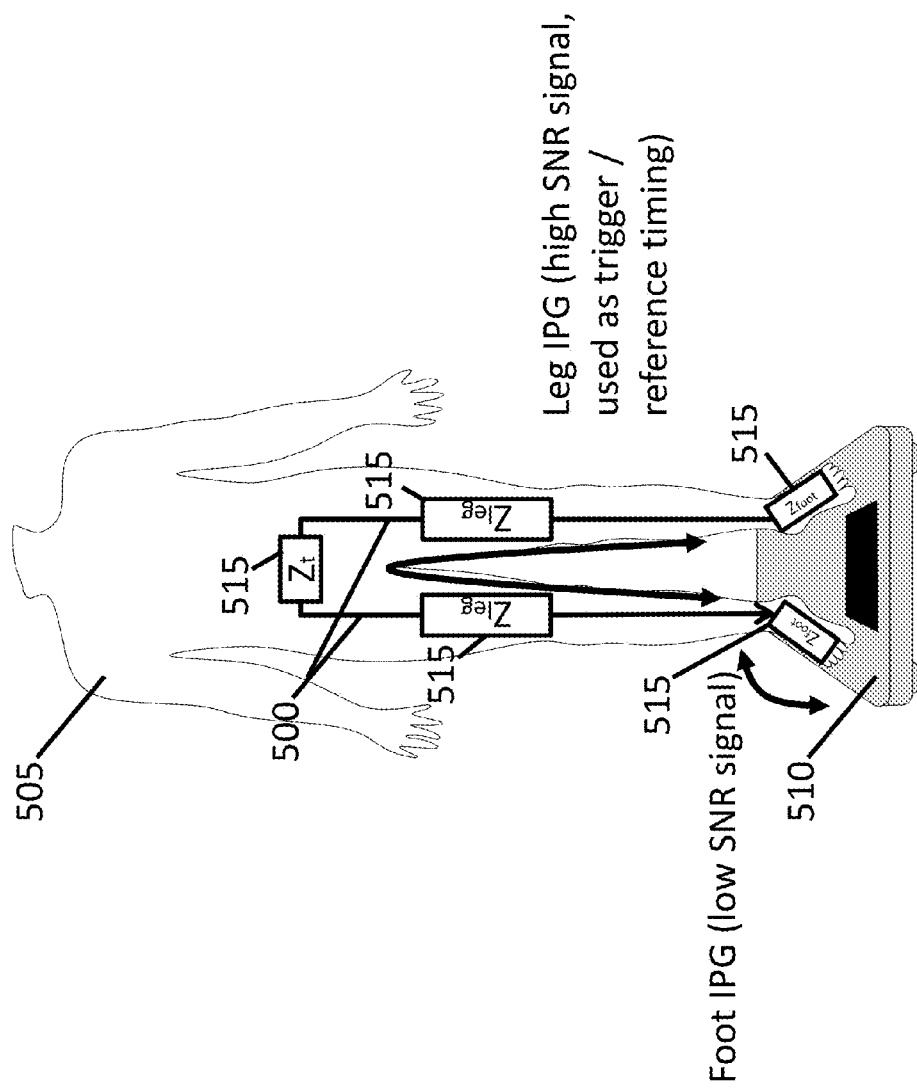
Figure 7A:
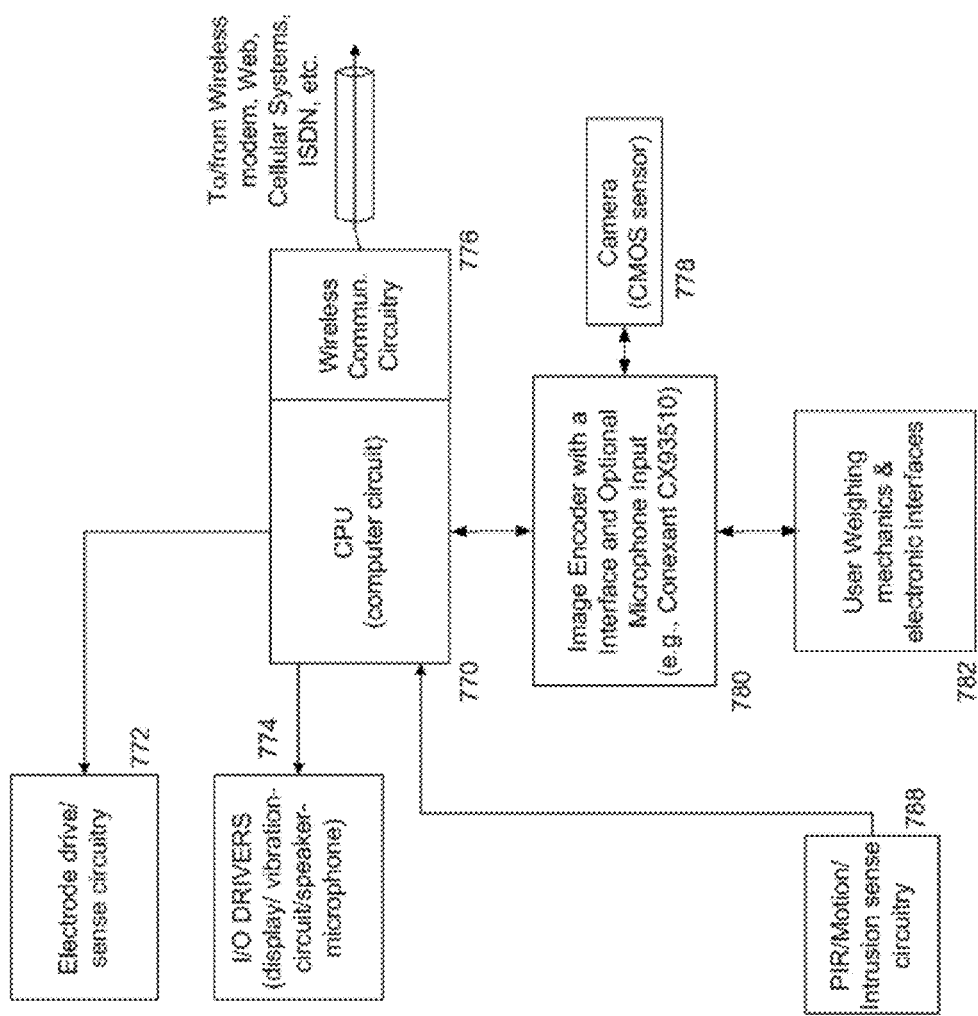
Figure 7B:
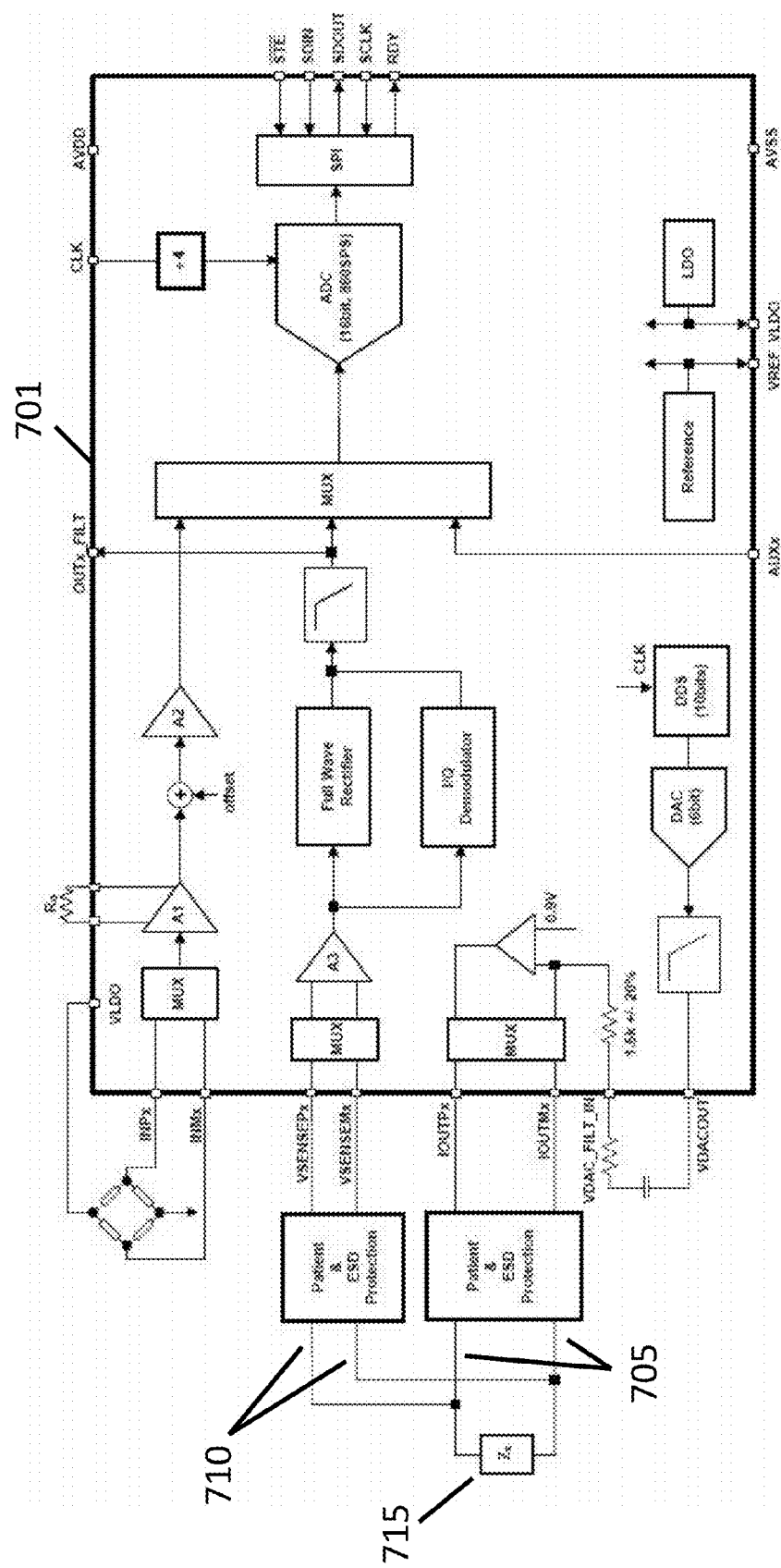
Figure 8A:
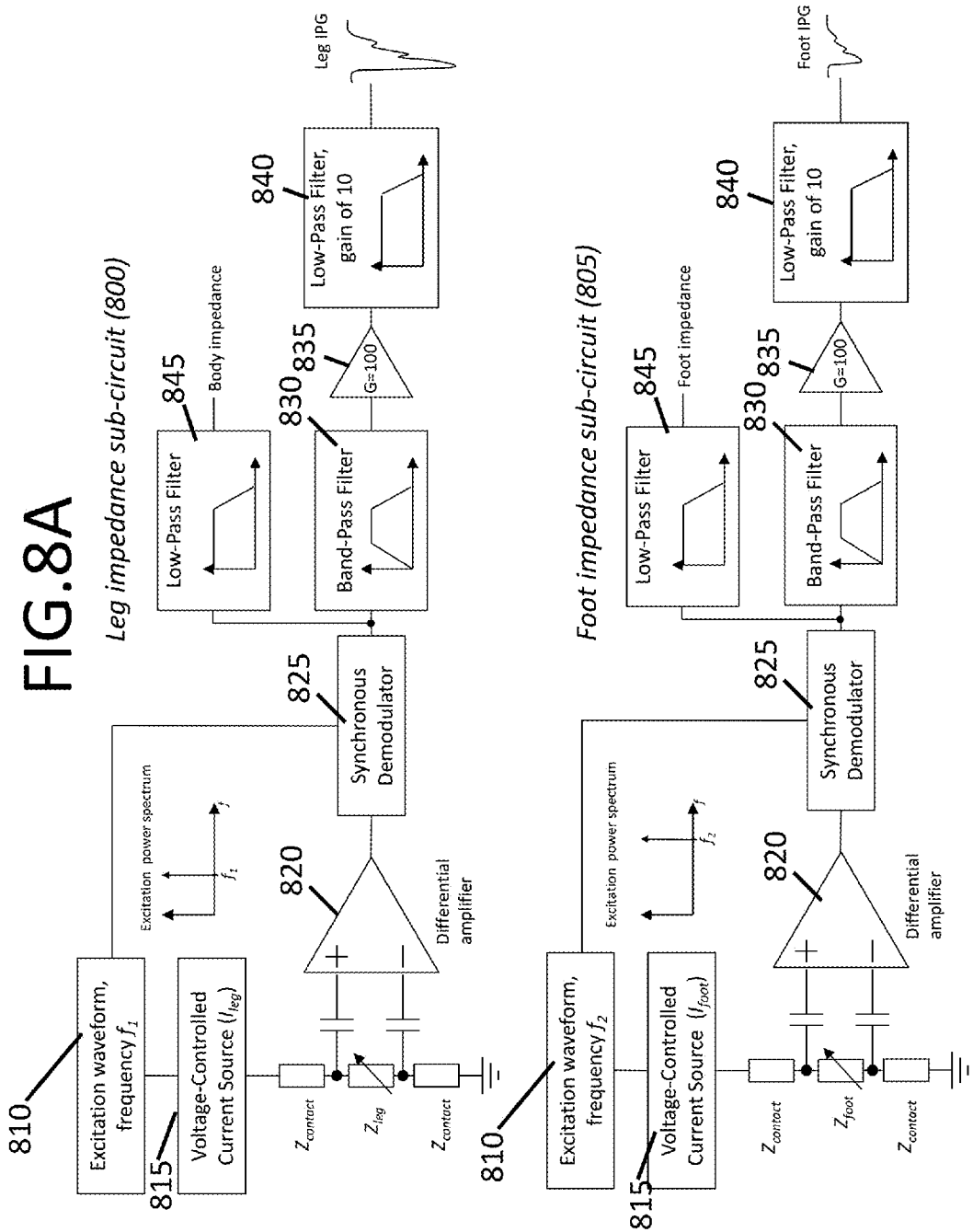
Figure 8B:
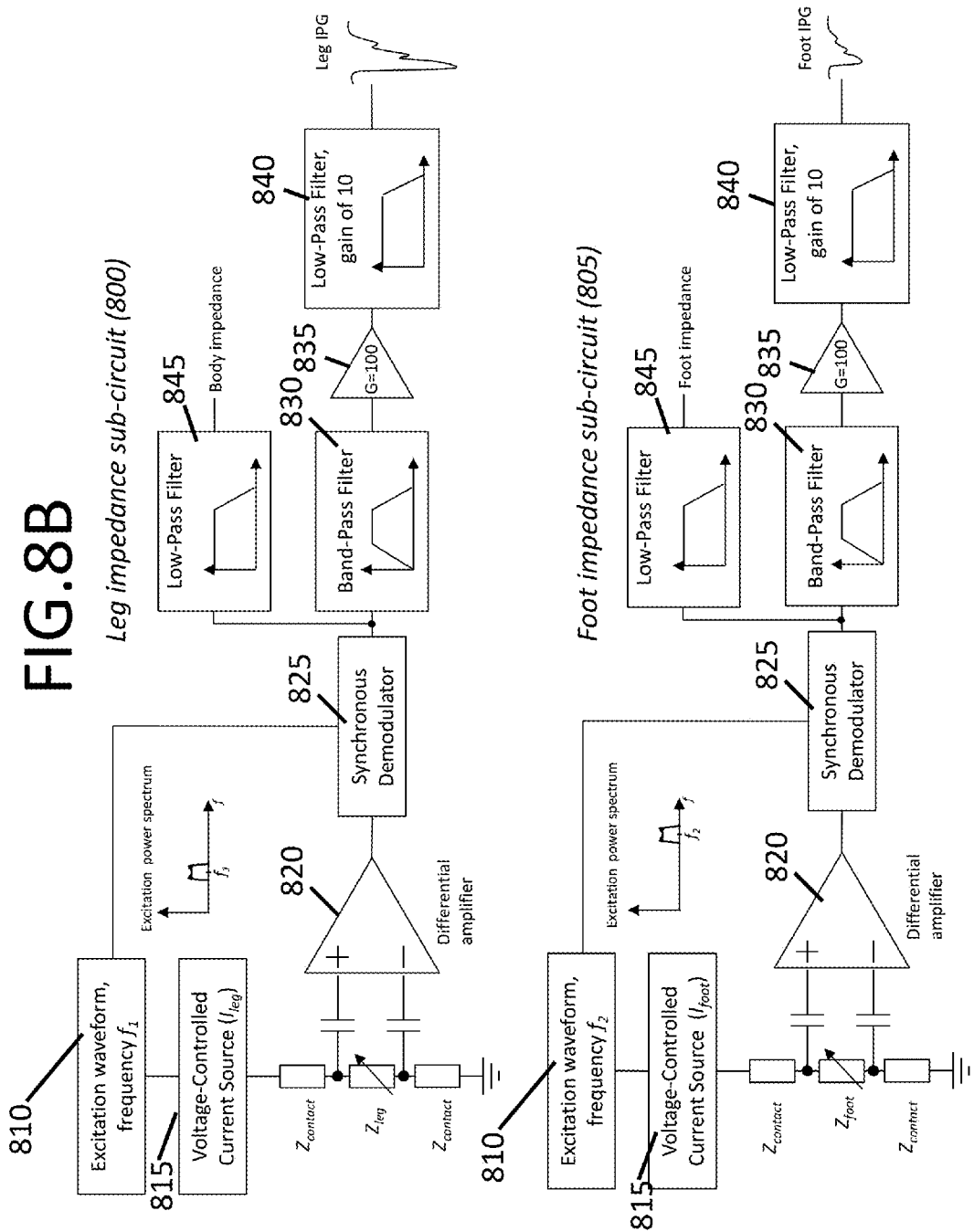

FIGS. 2 and 2-*i* show top views of a multi-function scale with large-area display, consistent with various aspects of the present disclosure;

FIGS. 3A-D show top views of a number of multi-function scale displays, consistent with various aspects of the present disclosure;

FIG. 4 shows a multi-function scale with large-area display, consistent with various aspects of the present disclosure;

FIG. 5A is a flow chart illustrating an example manner in which a user-specific physiologic meter/scale may be programmed to provide features consistent with aspects of the present disclosure;

FIG. 5B shows current paths through the body for the IPG trigger pulse and Foot IPG, consistent with various aspects of the present disclosure;

FIG. 6 shows an example of the insensitivity to foot placement on scale electrodes with multiple excitation and sensing current paths, consistent with various aspects of the present disclosure;

FIG. 7A depicts an example block diagram of circuitry for operating core circuits and modules, including, for example, those of FIGS. 8A-8B, used in various specific embodiments of the present disclosure;

FIG. 7B shows an exemplary block diagram depicting the circuitry for interpreting signals received from electrodes.

Figure 10:
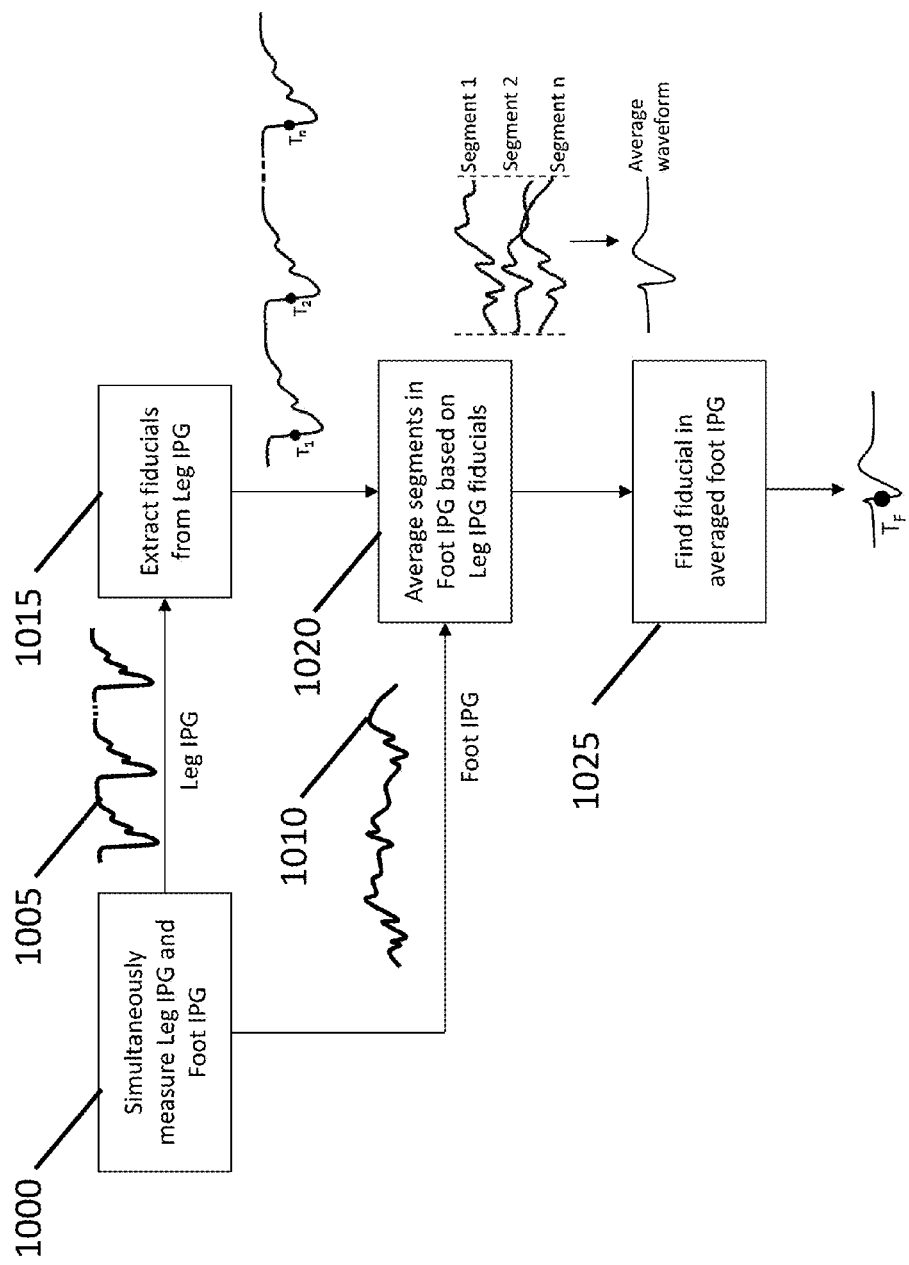
Figure 11:
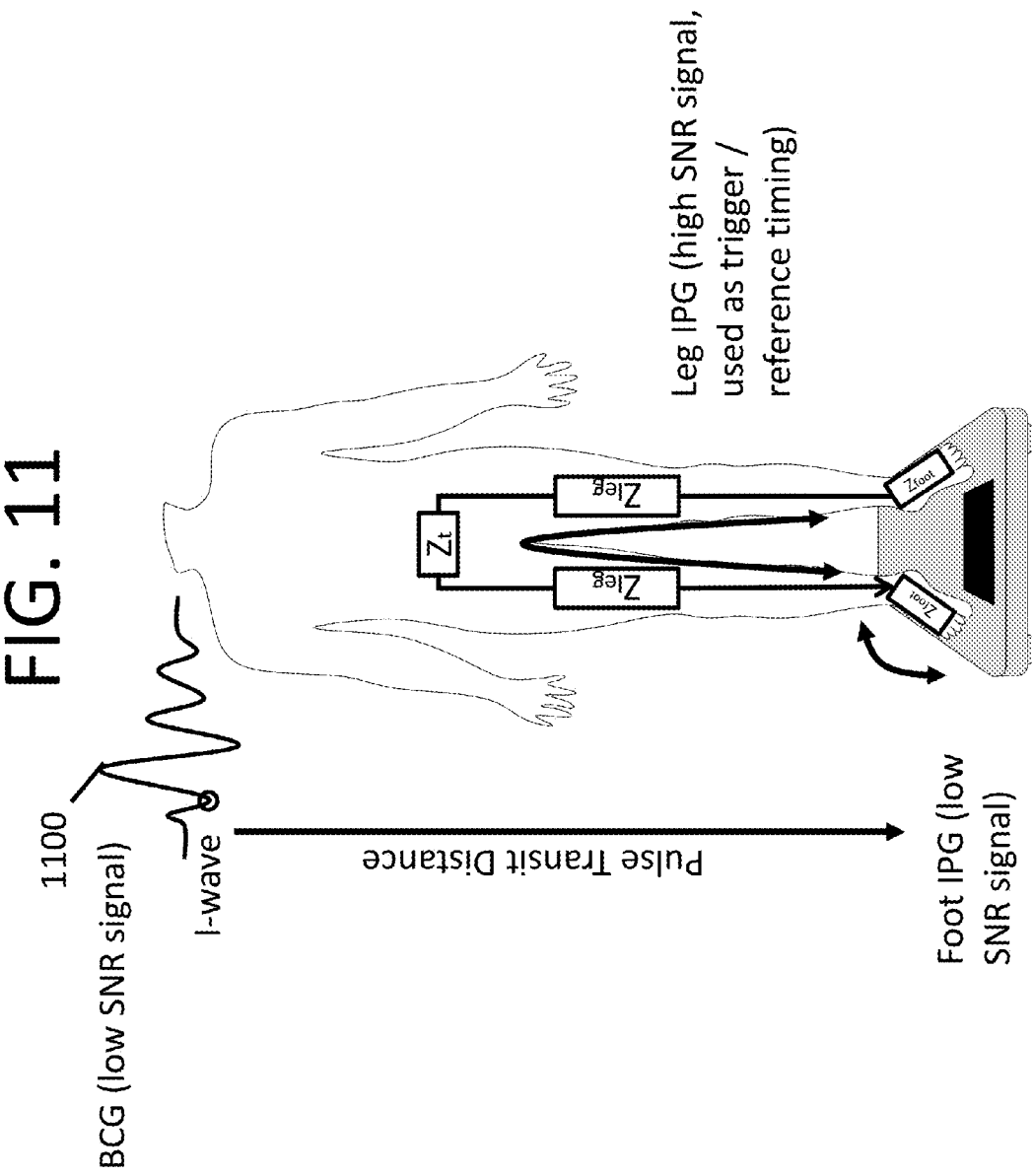
Figure 12:
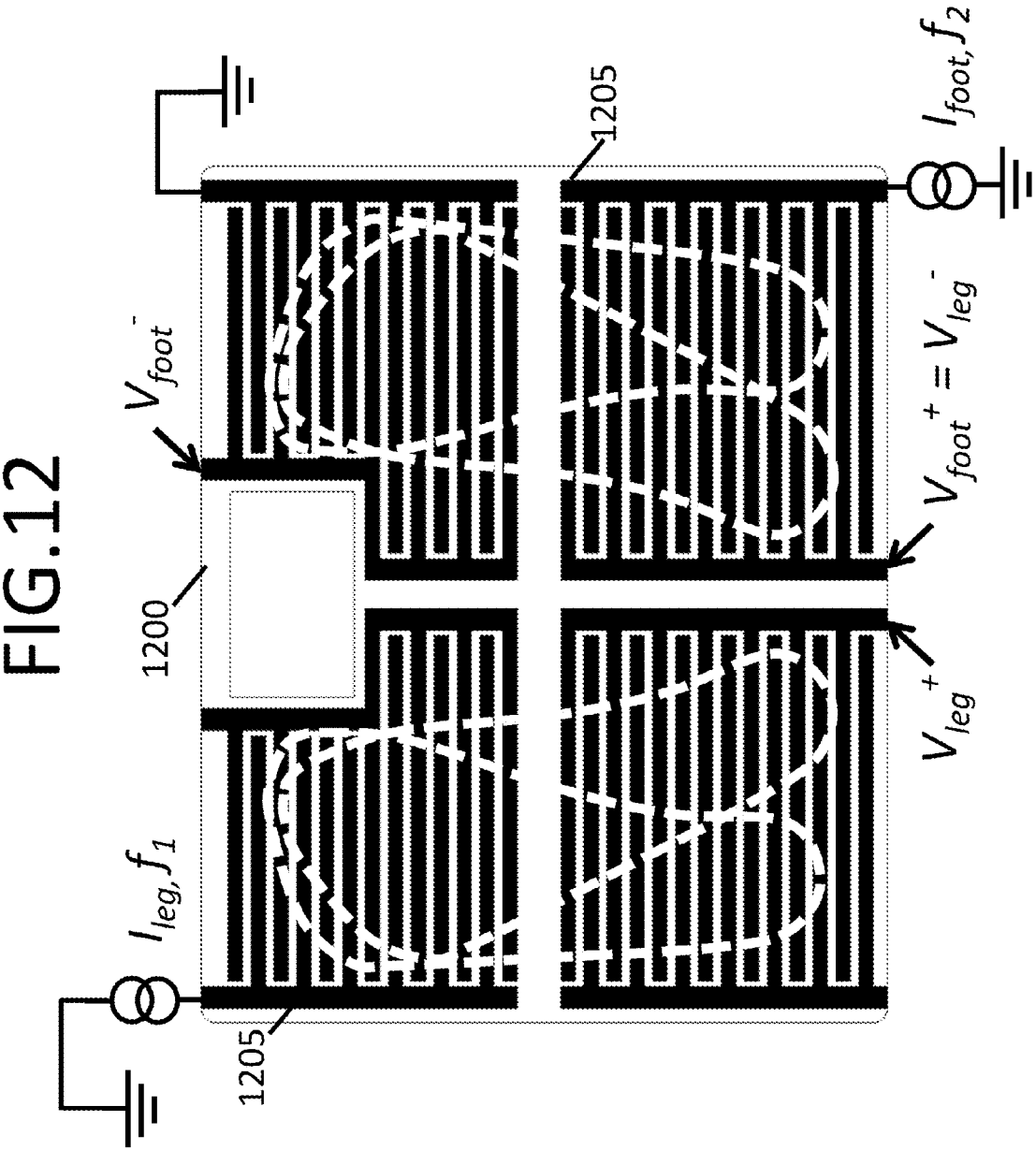
Figure 13A:
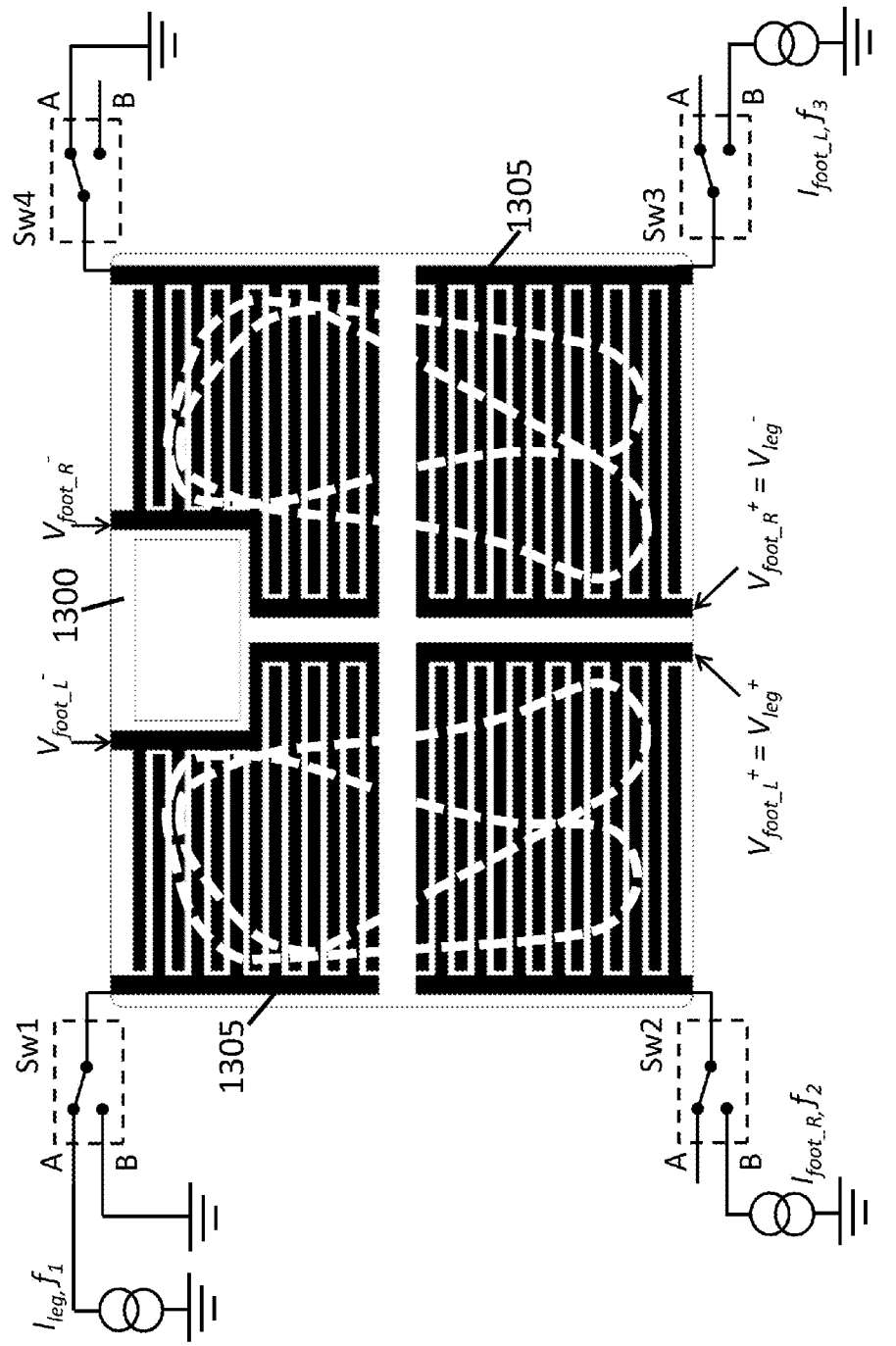
Figure 13B:
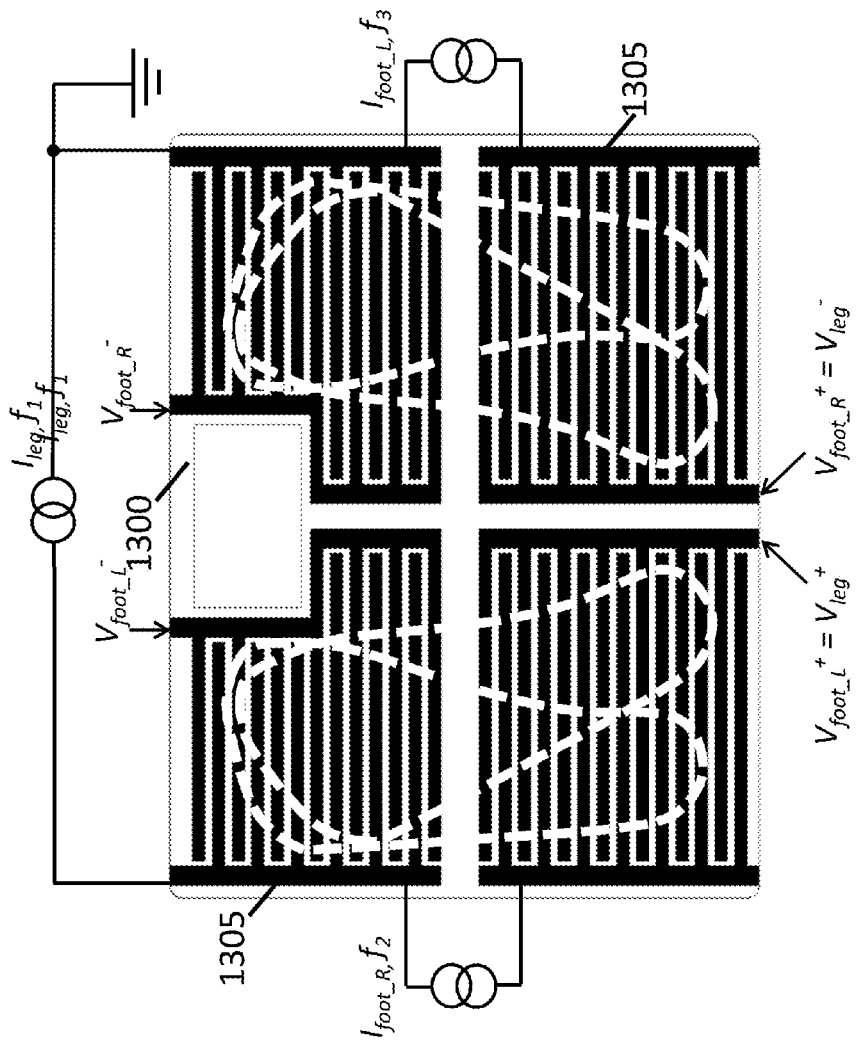
Figure 15:
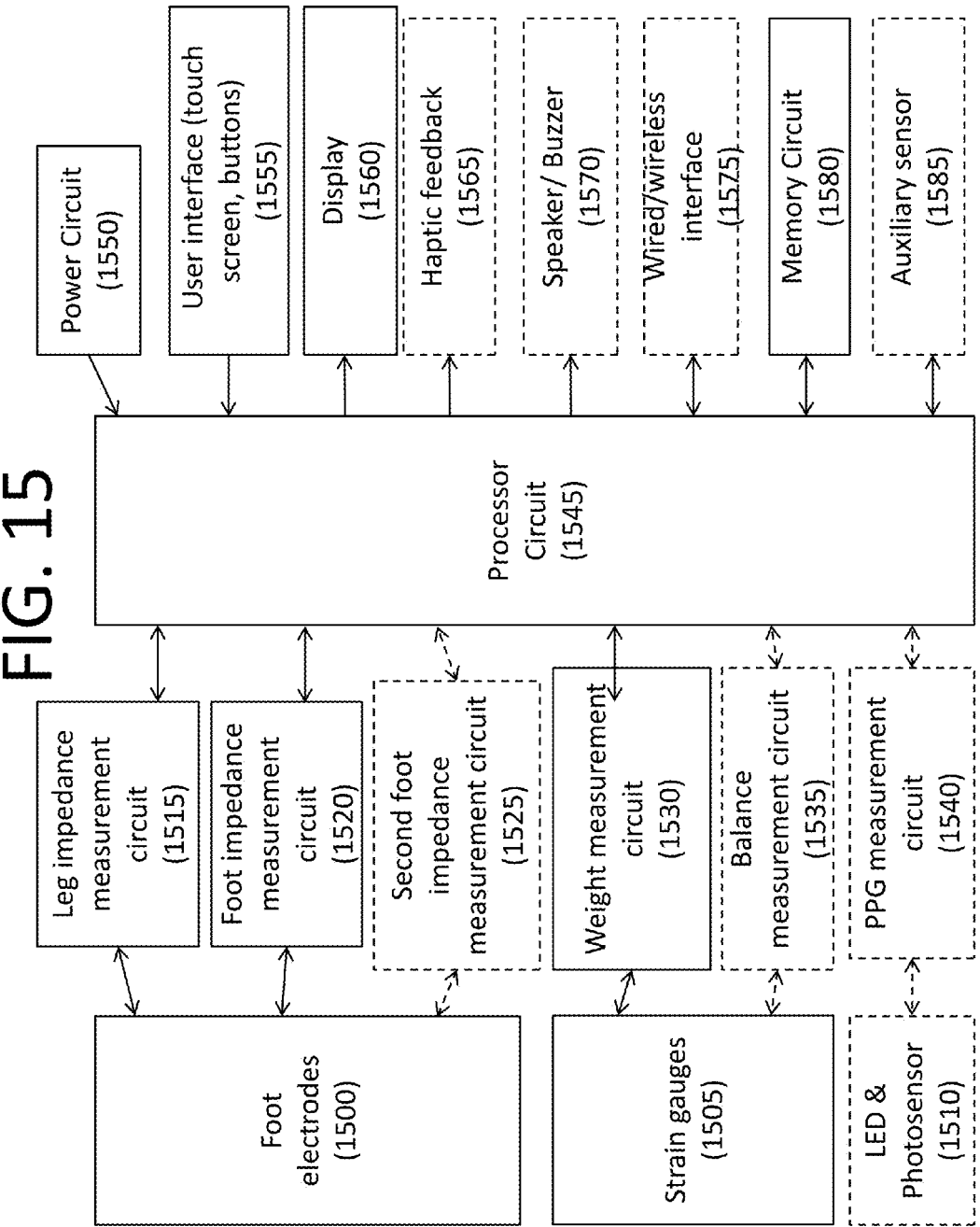
Figure 16:
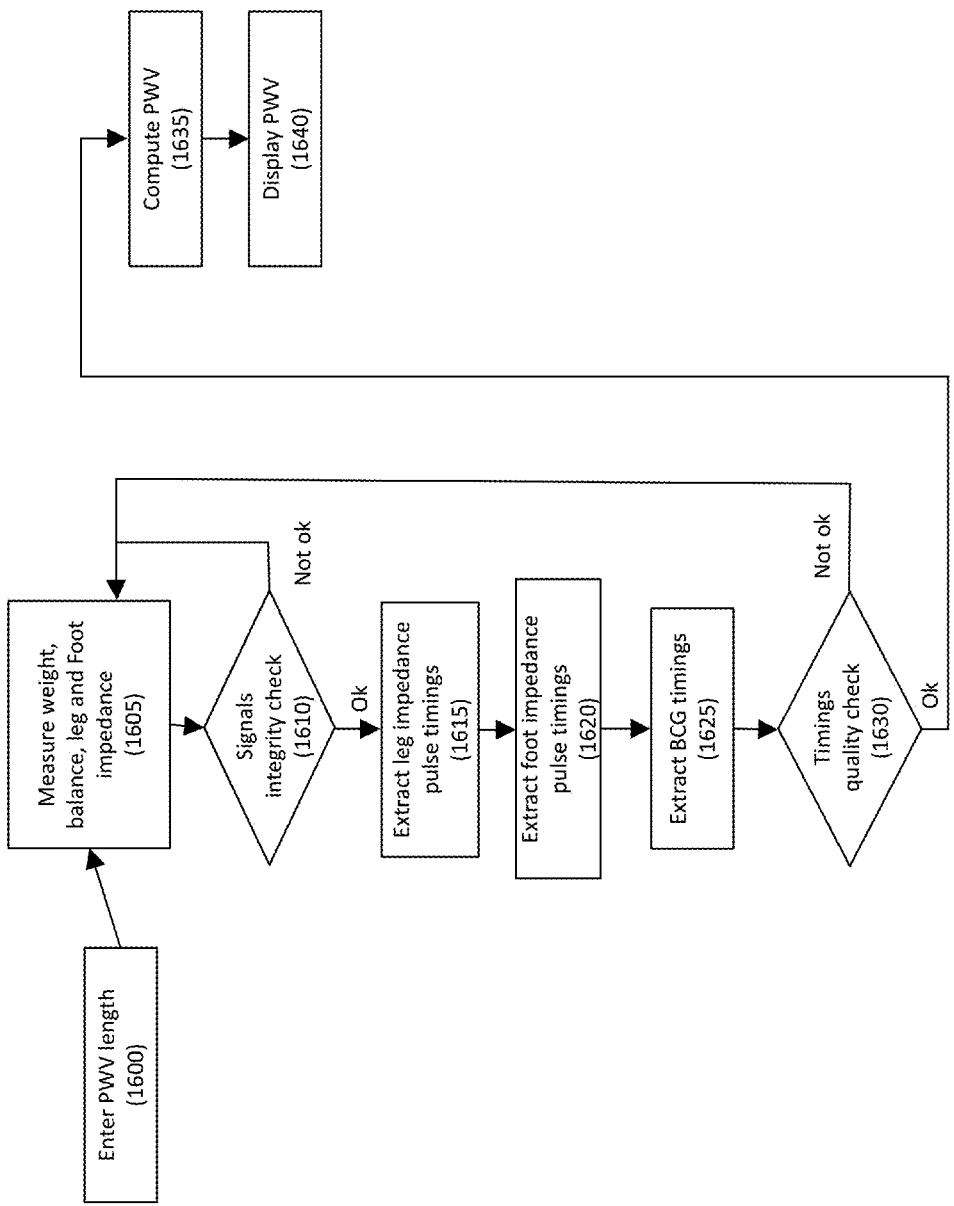
Figure 17:
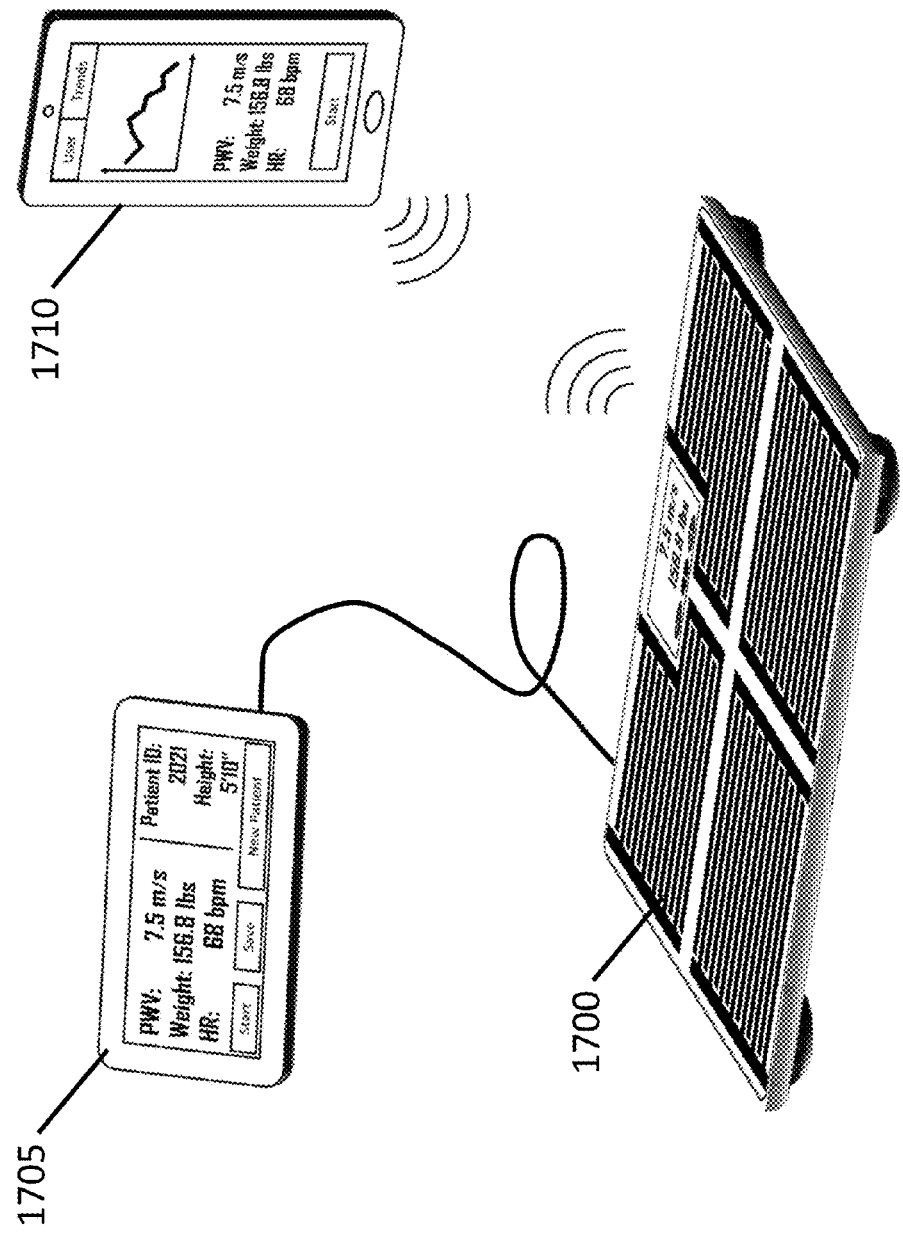

FIGS. 8A-8B show example block diagrams depicting the circuitry for sensing and measuring the cardiovascular time-varying IPG raw signals and steps to obtain a filtered IPG waveform, consistent with various aspects of the present disclosure;

FIG. 9 shows an example block diagram depicting signal processing steps to obtain fiducial references from the individual Leg IPG "beats," which are subsequently used to obtain fiducials in the Foot IPG, consistent with various aspects of the present disclosure;

FIG. 10 shows an example flowchart depicting signal processing to segment individual Foot IPG "beats" to produce an averaged IPG waveform of improved SNR, which is subsequently used to determine the fiducial of the averaged Foot IPG, consistent with various aspects of the present disclosure;

FIG. 11 shows an example configuration for obtaining the pulse transit time (PTT), using the first IPG as the triggering pulse for the Foot IPG and ballistocardiogram (BCG), consistent with various aspects of the present disclosure;

FIG. 12 shows another example of a scale with interleaved foot electrodes to inject and sense current from one foot to another foot, and within one foot, consistent with various aspects of the present disclosure;

FIG. 13A shows another example of a scale with interleaved foot electrodes to inject and sense current from one foot to another foot, and to measure Foot IPG signals in both feet, consistent with various aspects of the present disclosure;

FIG. 13B shows another example of a scale with interleaved foot electrodes to inject and sense current from one foot to another foot, and to measure Foot IPG signals in both feet, consistent with various aspects of the present disclosure;

FIG. 13C shows another example approach to floating current sources by using transformer-coupled current sources, consistent with various aspects of the present disclosure;

FIGS. 14A-D show an example breakdown of a scale with interleaved foot electrodes to inject and sense current from one foot to another foot, and within one foot, consistent with various aspects of the present disclosure;

FIG. 15 shows an example block diagram of circuit-based building blocks, consistent with various aspects of the present disclosure;

FIG. 16 shows an example flow diagram, consistent with various aspects of the present disclosure;

FIG. 17 shows an example scale communicatively coupled to a wireless device, consistent with various aspects of the present disclosure; and FIGS. 18A-C show example impedance as measured through different parts of the foot based on the foot position, consistent with various aspects of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

Various aspects of the present disclosure are directed toward a multi-function scale with a large-area display to present results of the scale's multiple sensing functionalities as related to user-physiological (e.g., fitness) characteristics, and may provide other information pertinent to the user. In many embodiments, the multi-function scale provides a number of biometric and physiological measurements. Based on the measurements, a condition or conditions of the user are displayed on the large-area display between or beneath the user's feet.

In some embodiments of the present disclosure, a weighing scale includes a support structure, a display, (user-targeted) circuitry, and a communication driver. The support structure has a platform region with sensor circuitry therein, and which engages a user via the sensor circuitry while the user stands on the platform region. The sensor circuitry collects physiological data from the user such as cardiovascular information pertaining to states of exertion, which is then forwarded on to the circuitry for analysis. Other physiological data may also be collected, such as measurements of body composition. The display displays data through the platform region, with the data relating to physiological parameters of the user as determined by the circuitry and pertaining to a physiological assessment of the user (e.g., arrhythmia cardiac dis-function, cardio-heath, fitness condition, and/or other information that might otherwise be suggested by ECG and/or holter monitor data collection effort).

In many embodiments, the user may compare his or her physiological parameters to a health metric. Some examples of health metrics include physiological parameters of an average individual of the same sex, age, height, weight, etc., or physiological parameters indicative of a level of cardiac-health, physical health, and/or physical fitness to which the user wishes to achieve (e.g., run a marathon, or summit Mount Everest). In one specific embodiment, circuitry accesses current physiological parameters of the user and the health metric associated with at least one of a number of the user-specific physiological parameters stored in the data-access circuit (sex, age, height, weight of the user). Current physiological parameters may, for example, be obtained by sensing physiological data of the user and assessing the physiological parameters of the user, as discussed in more detail below, or by accessing recent physiological parameters of the user stored in a data-access circuit. The circuitry then compares the current physiological parameters to the stored health metric to determine a physical fitness condition of the user.

In many embodiments, the scale (including circuitry) determines (and displays) action(s) to encourage improvement of the user's cardiac and/or physical fitness, after determining the user's physiological parameters and/or physical fitness characteristics. In many embodiments, the circuitry may transmit (via the data-access circuit) to external personal electronic devices associated with the user, the physiological parameters, physiological data, recommended physical regimens, and/or other data indicative of the physical health of the user.

In various embodiments of the present disclosure, a scale includes a display that receives touch signal data indicative of engagement of the user on a platform region above the display and the associated position and movement of the user on the platform region. The touch signal data is transmitted to a communication driver which processes the touch signals, and determines the associated position and movement with such touch signals. Accordingly, the user is able to use their feet to make selections on the display, such as selecting a physiological test to conduct, inputting information relevant to the user's health, among other activities such as browsing entertainment related data displayed while the scale is conducting a test. Although the present disclosure generally refers to the physiological test (e.g., physiological assessment) as a fitness test, the physiological test, in accordance with the present disclosure, is not so limited and can be a general assessment of cardio-related health, a physiological test, and/or a test for a specific physiological and/or cardiac parameter and/or condition, among other tests. In further embodiments, the touch signal data may be used by a communication driver of the display. In one such embodiment, the communication driver recognizes whether the user is standing on the platform region. When the communication driver determines the user is not standing on the platform region, the communication driver presents information via a large-area display mode of the display. When the communication driver determines the user is standing on the platform region and, the communication driver presents information via a reduced-area display mode in a reduced-area display region of the platform region which is adjacent to feet of the user, when the user is standing on the platform region.

In certain more specific embodiments of the touch-screen display discussed above, the user-targeted circuitry may store data indicative of a user's foot size, shape and/or other identifying characteristic in a data-access circuit. Accordingly, when an unidentified user engages a platform region of the scale, the circuitry may compare the unidentified user's foot to user-specific data stored in the data-access circuit to determine the identity of the user.

Certain embodiments of the present disclosure are directed to the aesthetic appearance of the scale when not in use. In one such embodiment, the scale further includes a camera to capture image data indicative of an area around the scale and presence of the user. Accompanying image processing circuitry receives the captured image data from the camera and determines color and pattern themes associated with the image data of the area around the scale, and the presence of the user; based on the determinations of the image processing circuitry, the display functions in either an active or idle mode. In the active mode, determined by presence of the user by the image processing circuitry, the display presents information that corresponds to the physiological parameters of the user. In the idle mode, determined by non-presence of the user by the image processing circuitry, the display presents an image indicative of the area around the scale, based on the image data processed by the image processing circuitry.

In certain specific embodiments of the present disclosure, after the scale analyzes physiological data of a user and determines the user's physiological parameters, such data can be logged and trended (over a period of time) with previously recorded physiological data (e.g., weight and body composition) and stored in a data-access circuit.

In a further embodiment of the present disclosure, in addition to measuring a user's baseline physiological/hemodynamic parameters, a specific physiological assessment mode (e.g., fitness-testing mode) is invoked. The scale, when put into physiological assessment mode, coaches the user to raise his or her heart rate and then measures physiological/hemodynamic parameters of the user (e.g. heart rate, (BCG), heart rate, pulse-wave velocity (PWV), oxygen saturation, etc.), either alone or in combination. In this mode, the user is instructed by the scale or another linked device (e.g. cell phone), via an audible or visual prompt to step off the scale and raise the user's heart rate (e.g. go for a run, run up and down stairs, jumping jacks, or do another form of exercise), and then return to the scale. When the user returns to the scale after exercise the user's heart rate is substantially elevated relative to the user's baseline (resting) values already recorded. The user is instructed to stand on the scale, while the scale repeatedly measures the user's physiological/hemodynamic parameters, including how quickly the user recovers from physical exertion. In certain embodiments, the user is instructed to rest and return to the scale after a given amount of time (e.g., the scale may provide an indication of such a time period expiring, prompting the user to return to the scale), after which the scale obtains additional physiological measurements. Recovery slopes, time constants or other derived recovery parameters are computed from the recorded data and stored. As these parameters are collected and measured over a period of time (e.g. days, months, years, etc.) the user's recovery to a baseline level (or at least slope or time-constant of recovery) can be estimated. By comparing these recover-to-baseline parameters against a population, other health metrics, the user's baseline parameters and other historical data, the user's changes in fitness levels can be quantified and displayed to the user as feedback. By comparing the user's baseline physiological parameters to the user's parameters after periods of exercise the scale can provide an analysis over time of the change in the user's physical condition, and thereby the change in the user's overall physiological, cardio, and/or physical fitness. The scale can also provide trending data (e.g. communicating to the user if they are getting more or less fit over time). Measurement results can be compared against appropriate population norms or health metrics (e.g. age, race or gender) and against the user's own short and long-term results.

In a further embodiment of the present disclosure, the scale can also be linked to external devices such as pedometers, mobile devices, other personal electronic devices, or GPS trackers to give the algorithms access to more information about the fitness state of the user or the exercise that the user has completed (including the exercise specifically done to raise the user's heart rate for the fitness testing mode). The scale can also log and trend weight and body composition, as these measurements relate to the degree of fitness and to the overall goals of the user (e.g. reducing overall weight or body fat percentage).

A further embodiment of the present disclosure is directed to a scale that works with algorithms that coach the user over time in terms of training regimens to achieve specific goals such as, for example training to run a marathon or play soccer. The algorithms may, for example be embodied in the scale, in the cloud, in a user's mobile electronic device or computer.

In various embodiments a multi-function scale including a display is disclosed, the display being effectively the entire top surface of the scale. Support glass above the display transmits the weight of a user to a bezel along the perimeter of the scale (away from the display), while also transmitting touch-capacitive signals indicative of a user's position and movement on the support glass through the display to scale circuitry. The bezel houses load cells equally spaced along the perimeter of the scale. Each load cell outputs an electrical signal indicative of a mass transmitted from the user through the load cell to the scale circuitry. A support frame is attached to the bezel and supports the display within the bezel. A plurality of translucent electrode leads are embedded into the support glass to provide electrical signals to the scale circuitry; the electrical signals are interpreted by the scale circuitry as being indicative of a condition of a user, such a condition being presented on the display for the user.

In some embodiments of the present disclosure, a display of a multi-function scale is touch-responsive or tilt-responsive. The display may portray simple menus that can be controlled by the user's feet/toes, hands or other body part. A user's feet (or hands) are sensed via touch sensors on the screen or display and the scale can identify the outline of a user's feet (or hands or other body part). The user's feet (or hands) may provide user input for functional or aesthetic feedback via the display such as producing animated graphics around the users feet or hands (e.g., simulated lapping surf videos that interact with the user's feet or hands; glowing around the user's feet or hands; fish nibbling at the toes, etc.). A user may also change posture, shifting the weight distribution over the scale's load cells to provide user input. The user provided feedback allows for the selection of menu options, test selection, browsing information or articles presented on the display, or the input of test relevant user data such as age, medical conditions, etc. In various embodiments, the touch-responsive screen indicates to scale circuitry the location of a user's feet relative to a plurality of electrodes located across a top surface of the multi-function scale. This permits the processor to select appropriate electrodes for a designated biometric measurement, based, at least in part, on the real-time location of the user's feet on the scale.

In further specific embodiments of the present disclosure, a multi-function scale is communicatively coupled with one or more of a user's portable electronic device, an internet router, or other home electronic device. The scale communicates and exchanges data with these devices for display and control by a user (e.g. using physiological parameters to improve a fitness or health condition). In various embodiments, while the multi-function scale is conducting biometric and physiological measurements of the user, the user (by way of the touch-responsive screen) may interact with one or more of the other devices. For instance, the user may browse news communicated to the multi-function scale by an internet router, change a station on a television or a song playing on a sound system, or review the user's schedule transmitted to the multi-function scale by the user's smartphone. Additionally, while the scale is conducting barometric and physiological measurements of the user prior to user identification, the display portrays interesting or entertaining information (e.g., surf lapping at the user's feet). In yet further implementations of the disclosure directed to smart-homes, a multi-function scale provides user control (via the touch-screen display) a plurality of other devices throughout the home, such as a climate control system, security system, or operation of a shower. The electronic communications between the multi-function scale and the various devices may take the form of either wireless or wired communications. Further, a multi-function large display scale can be used to communicate with other scale users either using the same scale unit or another scale in the home or other wireless or personal electronic devices. For instance, a message or note may be left, or a meeting or appointment may be confirmed. Further, digital communication and haptic feedback from a smart watch may be implemented to make selections related to scale functionality.

In some embodiments of the present disclosure, the scale is used in conjunction with workout activities. For example, the scale can be used as a force meter, for exercises involving the feet (e.g., conducting a leg press or military press while standing on the scale). Such metering would also be useful for maintaining consistent exerted forces during ballistic exercises and to chart fatigue over repetitions (and to also compare to previous workout sessions). In certain implementations, the scale is integrated within exercise equipment to facilitate such detection and, for example, to provide an accurate indication of an amount of force actually applied to move weight. In other related embodiments, the scale may be used intermittently during a workout regimen to verify that the regimen (or current exercise) is raising the users physiological parameters to the appropriate levels for the exercise (e.g., that a cardiovascular exercise, such as jogging, is raising the user's heart rate to 80% of its maximum).

Certain aspects of the present disclosure are directed toward a multi-function scale that obtains a plurality of impedance-measurement signals while a set of at least three electrodes are concurrently contacting a user. Additionally, various aspects of the present disclosure include determining a plurality of pulse characteristic signals based on the plurality of impedance-measurement signals. One of the pulse characteristic signals is extracted from one of the impedance-measurement signals and is used as a timing reference to extract and process another of the pulse characteristic signals. The signals obtained by the scale are indicative of a condition of the user, such as percentage: muscle mass percentage, body water percentage, among others. The condition of the user is displayed on a large-area display beneath the user's feet, along with other information that may be preprogrammed or requested by the user for display such as time of day, traffic conditions, stock portfolio, weather, as well as a plurality of other pieces of information that may be collected.

In another embodiment, an apparatus includes a platform area and a set of electrodes including a plurality of electrodes over the platform area for contacting one foot of a user and including at least one other electrode configured and arranged for contacting the user at a location along a lower limb (e.g., other foot) that does not include the one foot. Pulse-processing circuitry is communicatively coupled to, and configured with, the set of electrodes to obtain a plurality of impedance-measurement signals while each of the electrodes is concurrently contacting the user and to determine a plurality of pulse characteristic signals based on the plurality of impedance-measurement signals. At least one of the impedance-measurement signals is obtained within the one foot and another of the impedance-measurement signals is obtained between the one foot and the other location. One of the pulse characteristic signals is extracted from one of the impedance-measurement signals and is used as a timing reference to extract and process another of the pulse characteristic signals.

Various aspects of the disclosure are directed to a multi-function scale with a large-area display. The large-area display may be programmed to display aesthetically pleasing screen savers, both when in use, or idle. For example, images, animations, and videos, may be presented on the display with overlaid information (as may be selected by the user). In some specific embodiments of the present disclosure, where the multi-function scale, and based on its measurements, has determined a condition in the user indicative of increased stress levels (as indicated by high blood pressure, heart rate, etc.), for example; the multifunction scale may display images or video, such as waves lapping over sand and play accompanying sounds or music, among other sensory devices, intended to calm and sooth the user. In yet further embodiments, based on an assessed condition, as indicated by the multi-function scale measurements, the multi-function scale may suggest audibly or visually (through the scale's display) activities, dietary restrictions, or in the case where the indicated condition is life-threatening (e.g., measurements indicating an imminent heart attack or stroke, etc.), call an ambulance for the user. Information may also be portrayed on the display of the scale for a period of time when the user is off the device.

Another embodiment is directed to an apparatus having a platform area, a set of electrodes and pulse-processing circuitry. The electrodes include a plurality of electrodes over the platform area for contacting a user at a limb extremity (being the hand or foot) and one or more other electrodes for contacting the user at a different location. The pulse-processing circuitry is communicatively coupled to, and configured with, the set of electrodes to obtain a plurality of impedance-measurement signals while each of the electrodes is concurrently contacting the user and to determine a plurality of pulse characteristic signals based on the impedance-measurement signals. At least one of the impedance-measurement signals is obtained within the limb extremity and another of the impedance-measurement signals is obtained between the limb extremity and the other location. One of the pulse characteristic signals is extracted from one of the impedance-measurement signals and is used as a timing reference to extract and process another of the pulse characteristic signals.

In various embodiments of the present disclosure, a multi-function scale includes imaging circuitry such as a camera and image processing circuitry. Where a camera is implemented, the camera is directed either at the floor below the scale or the surrounding area. Based on the images processed (by the image circuitry) of the area surrounding the scale, the multi-function scale's large-area display depicts an image that mimics the surrounding area when idle. For example, in some embodiments, the scale depicts an image indicative of the surface, flooring or floor covering below the scale, enabling the scale to "blend in" to its surroundings, minimizing any detraction of aesthetics the scale would otherwise cause through its visually non-conforming presence, if desired by the user. In another embodiment of the present disclosure, the scale is mountable flush with or inset into a floor in which the scale is located. This approach can be used to further enhance the "blend in" effect of the scale and to facilitate powering via a hardwired voltage connection. The result is that, when the multi-function scale is idle, the scale is effectively camouflaged from view or at a glance. In other embodiments, the camera may be directed at an upward angle, providing a view of the room in which the multi-function scale is located. Based on image data collected by the camera and processed by image processing circuitry, the display will present the prominent colors and patterns found in the room, minimizing the aesthetic detraction of the multi-function scale.

In a further embodiment of the present disclosure, a multi-function scale includes circuitry such as a camera, microphone or image processing circuitry that interacts with an external environmental sensor. Such an environmental sensor may, for example, be connected to a personal electronic device to alert a user of motions and sounds in a house, or to communicate wirelessly with another individual either nearby or at a distant location. In some implementations, the scale communicates with and relies on an external environmental sensor that is wirelessly connected to the user's home or living environment. For example, in one embodiment the external environmental sensors facilitate power saving by alerting the scale that a user is moving toward the location of the scale, thereby prompting the scale to transition (turn on or power up) from idle or reduced-display mode to active or large-display mode, identify the user, and begin interacting with the user. Further, the external environmental sensor can also trigger the scale to turn off or to transition from active mode or large-display mode to a reduced-display or idle mode, in response to sensing that the user is leaving the area where the scale is located.

A further embodiment of the present disclosure is directed to a scale that facilitates power-saving by communicating with a bed or bedroom-based sensor that can trigger the scale to turn on and transition from idle or reduced-screen-mode to active or large-display mode when the sensor detects user activity. For instance, by detecting that user wakes-up and/or gets out of bed, the scale can be activated.

Various other embodiments of the present disclosure include a scale, that when placed near the user's sleeping environment (e.g. bedroom) and coupled with a sensor located on the user, or in or near the user's bed or bedroom, analyzes and stores the user's sleep patterns, sleep environment and climate, and other physiological measurements (e.g. average heart rate, respiratory and breathing rate, movement, etc.) of the user while the user is asleep. One benefit of such an embodiment is that use by the user promotes improved sleep and overall health and wellness. Data obtained while the user is sleeping can be displayed on the scale or communicated wirelessly to or from other personal electronic devices or programs for viewing, storage or future analysis by the user.

In a further embodiment of the present disclosure, the scale includes a power source such as a battery that can be charged or recharged wirelessly (e.g. using a variety of wireless charging modalities such as: magnetic inductive charging magnetic resonance charging, radio wave charging, and ultrasound charging). The scale unit may also serve as a charging portal for charging or powering other portable electronic devices wirelessly.

In one power-saving embodiment of the present disclosure, the scale display is operated in a large-area display mode, where the entirety of the surface of the scale platform consists of the display when the user is not standing on the scale; and a smaller or reduced-area display mode, when the user is standing on the scale (e.g., the portions of the display visible to the user). In some embodiments, only a small portion of the display between the user's feet will continue to display information to the user in the reduced-area display mode, and in other embodiments the reduced-area display mode turns-off the display area under the user's feet to save battery power.

In another power saving embodiment of the disclosure, the scale may operate in an active mode, determined by the presence of the user by a camera or microphone integrated onto the scale. When image processing circuitry associated with the camera senses motion (or the microphone circuitry detects a noise), the scale enters an active mode and presents information that corresponds to the physiological parameters of the user or other information as may be programmed by the user. In the alternative, idle mode, where the scale has been inactive for a programmed period of time, or the image processing circuitry and microphone circuitry determine the lack of user presence in the room, the scale may turn-off the display to save power, present an image indicative of the area around the base unit, or present and image or animation selected by the user (as may be desired by the user).

The above discussion/summary is not intended to describe each embodiment or every implementation of the present disclosure. The figures and detailed description that follow also exemplify various embodiments.

Figure 1:
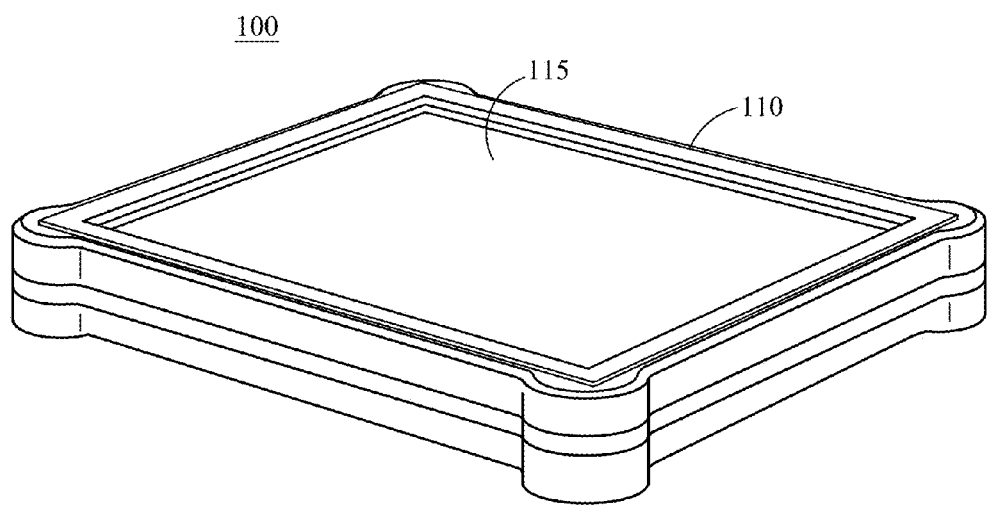
FIG. 1 shows an isometric view of a multi-function scale with large-area display, consistent with various aspects of the present disclosure.

Turning now to the figures, FIG. 1 shows an isometric view of a multifunction scale 100 with a large-area display (beneath platform region 115), consistent with various aspects of the present disclosure. In this particular embodiment, the scale 100 has a primarily rectangular shape with a support structure 110 around the perimeter of the scale that transfers the weight of a user on the platform region 115 through load cells in each corner of the support structure 110. The scale 100 may, for example, be implemented with circuitry that carries out one or more of the various physiological assessment (e.g., fitness) aspects described herein. It is to be understood that the aesthetic design of the multifunction scale 100 may take on a plurality of shapes and sizes (based on the needs of users, e.g., weight requirements or aesthetic preferences). A feature of the multifunction scale 110 is the large-area display that makes up the majority of the top surface of the scale. The display may present the user with a myriad of information, such as the results of physiological and biometric test results conducted by the scale, entertainment information (while the scale is conducting tests or a weight measurement), and aesthetic screen savers.

Figure 1A:
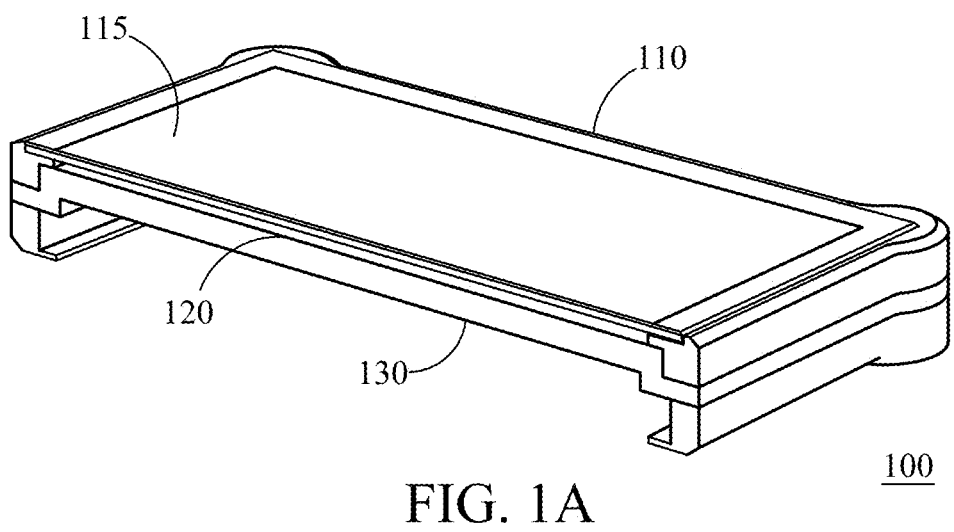
FIG. 1A shows an isometric, cross-sectional view of a multi-function scale with large-area display, consistent with various aspects of the present disclosure.

FIG. 1A shows an isometric, cross-sectional view of a multifunction scale 100 with a support structure 110 that integrates a large-area display 120, a platform region 115, and circuitry 130 (including at least circuitry, and a communication driver), consistent with various aspects of the present disclosure. The platform region 115 above the display 120 transmits the weight of a user to the support structure 110 and away from the display, while also transmitting touch-capacitive signals indicative of a user's position and/or movement on the platform region 115, through the display, to the scale circuitry 130. The support structure 110 is attached to a bezel which supports the display 120. The support structure 110 further houses load cells equally spaced along the perimeter of the scale 100. Each load cell outputs an electrical signal indicative of a mass transmitted from the user through the load cell to the scale circuitry (which interprets the electrical signals and presents the weight of the user on the display). In some implementations, a plurality of translucent electrode leads are embedded into the platform region 115 to provide electrical signals to the scale circuitry 130, and the electrical signals are interpreted by the scale circuitry 130 as being indicative of a condition of a user, with the condition being presented on the display 120 for the user. In other implementations, different types of sensors (e.g., organic semiconductors) are implemented with the sensor circuitry.

In an embodiment in accordance with FIG. 1A, a weighing scale 100 includes a support structure 110 having a platform region 115 with sensor circuitry therein (e.g., electrodes). The platform region 115 engages a user with the sensor circuitry while the user stands on the platform region 115 and use the sensor circuitry to collect physiological data from the user. While the user stands on the scale 100, the display 120 displays data through and throughout the entire platform region.

The scale 100 also includes circuitry 130 (e.g., user-targeted circuitry) including a communication driver. The circuitry 130 receives the physiological data from the sensor circuitry and determines physiological parameters of the user, including a user-weight metric, while the user stands on and engages the sensor circuitry of the platform region 115. The communication driver provides information from the circuitry to the display 120 for viewing by the user through the platform region 115. In various embodiments, the (user-targeted) circuitry operates to communicate with the user to instruct the user relative to states of physical exertion, to exercise or rest in order to obtain data from the user under the respective states. Such an approach may, for example, be carried out in a manner as discussed above.

In some embodiments the circuitry 130 also includes a data-access circuit that provides access to user-specific data including stored physiological parameters of the user in response to or developed by the circuitry 130 and to store physiological parameters of the user determined by the circuitry 130 (in other embodiments, the data-access circuit may be external to the scale 100, and may be accessed by the circuitry 130 over a communication network).

Load bearing characteristics of the multifunction scale 100 may provide both functionality and longevity. The platform region 115, in conjunction with the support structure 110 (and the bezel), minimizes the load transfer to the display 120 while still maintaining sufficient conductivity through the platform region 115 (e.g., a glass platform or other clear material) to the display 120 to allow for touch-screen functionality. If the platform region 115 is too compliant, under the user's weight, excessive force exerted on the display 120 may cause damage. If the platform region 115 is not conductively coupled to the display 120 (e.g., due to a gap there-between), touch-screen functionality of the scale 100 may be challenging. Accordingly, FIG. 1A discloses one embodiment that addresses such issues via a platform region 115 that transfer weight to the support structure 110 with minimal compliance, by which the display 120 remains conductively coupled to the platform region 115 while preventing excessive force from being exerted on the display 120 (that would otherwise cause damage).

In various embodiments, the circuitry 130 of the scale 100 operates in a physiological assessment mode. The circuitry 130 operates in a physiological assessment mode (e.g., fitness testing mode) by instructing a user to engage the sensor circuitry on the platform region 115 of the (weighing) scale 100, during respective states of exertion (e.g., in a reduced-exertion state and in an elevated-exertion state). The sensor circuitry collects physiological data from the user indicative of physiological (e.g., fitness) characteristics in each state. For instance, the circuitry 130 instructs the user to engage the sensor circuitry to obtain baseline physiological characteristics, and later instruct the user to raise or lower his or her heat rate, after which the user is again engaged by the sensor circuitry on the platform region 115. The sensor circuitry collects physiological data from the user for each physical exertion state, which the circuitry 130 uses to determine physiological parameters of the user. Methodologies for determining physiological parameters of the user are discussed in more detail below, in reference to FIGS. 5-18C. The communication driver receives the information (including the determined physiological parameters) from the circuitry 130 and provides the information to the display 120 for viewing by the user through the platform region. The physiological data thus can be used to provide the user or a medical professional with indications as to their level of cardiac-health and/or physical fitness.

In some embodiments, a (weighing) scale 100 as characterized above includes a data-access circuit that stores and provides access to user-specific data including physiological parameters of the user, which are responsive to or developed by the circuitry 130. The data-access circuit may be external to the scale 100 and may communicate and share user-specific data with the scale 100, as well as other electronic devices associated with the user (e.g., via a wired or wireless communication link). In some specific embodiments, the determined physiological parameters of the user are compared to physiological parameters of the user stored in the data-access circuit, in order to determine changes in cardiac-health, physical health, and/or physical fitness of the user over time. In one such embodiment, the circuitry 130 accesses the stored physiological parameters of the user in the data-access circuit, and compares current (sensed) physiological parameters of the user to the stored physiological parameters of the user to provide an indication of changes in cardiac-health, physical health, and/or physical fitness of the user over time.

In many embodiments, the scale 100 (including circuitry) determines (and displays) action(s) to encourage improvement of the user's cardiac and/or physical fitness, after determining the user's physiological parameters and/or physical fitness characteristics. For example, in some embodiments, where a user's determined physiological parameters are indicative of a lack of cardiovascular fitness, the scale 100 suggests that the user add a one mile jog into his or her daily fitness routine. In many embodiments, the circuitry transmits (via the data-access circuit) to external personal electronic devices associated with the user, the physiological parameters, physiological data, recommended physical regimens, and/or other data indicative of the physical health of the user. In such embodiments, the personal electronic devices optionally stores such data and/or further analyze the data in view of other stored data such as data indicative of diet and caloric intake of the user or the current physical regimen of the user. The personal electronic device may then instruct the user to adjust her or his diet and/or physical regimen accordingly. In further embodiments, the personal electronic devices transmits stored data indicative of the diet and caloric intake of the user, the current physical regimen of the user, or other health related data. The circuitry 130 may then also consider such data when determining the physiological parameters of the user to further improve the accuracy of such determined physiological parameters.

In one specific embodiment of the scale's physiological assessment mode (e.g., fitness testing mode), the circuitry 130 accesses a data-access circuit to determine previous recovery times of the user after physical exertion. The scale 100, via the circuitry 130, then instructs the user to engage sensor circuitry on a platform region 115 of the scale 100, after physical exertion, until the user has fully recovered to baseline values. The circuitry 130 receives the physiological data from the sensor circuitry indicative of the recovery time of the user, and compares the current recovery time of the user to previous recovery times of the user to determine the change in physical health of the user over time.

In another embodiment of the present disclosure, recovery-to-baseline parameters do not need to be measured from a maximum heart rate down to a baseline, alleviating difficulties in obtaining such a measurement which can be impractical in terms of the time needed to go from high exertion exercise to a baseline or resting heart rate. In such instances, algorithms performing the fitness testing look at changes in the user's various parameters relative to time, such as by determining that a user has recovered substantially enough toward baseline parameters to permit mathematical analysis to yield an estimate of recovery over time.

In a further embodiment of the present disclosure the results of the physiological testing can be displayed on the scale 100, on a mobile device, personal electronic device (e.g. smart watch or tablet), a computer, on a website, or in another way as desired by the user. The user can input related information such as the user's training regimen, specific exercise plan, diet or food plan, and fitness goals (e.g. run a marathon in a month, lose 10 pounds by a certain date, lower resting heart rate, or increase muscle mass). The scale 100 responds with an algorithmic estimation of desired fitness improvements per unit of time (e.g., day, week, or month).

The scale display 120 may present results of the physiological assessment and/or test in a number of ways, such as by displaying information in a mode for physiological assessment (e.g., fitness) that simply indicates "below average," "average," and "above average." In other embodiments directed to sophisticated fitness enthusiasts, the display 120 presents individual physiological parameters of the user, relative to the associated health metric, and also graphs the user's progress over time as compared to the particular health metric.

In certain specific embodiments of the present disclosure, as shown in FIGS. 2 and 2i, multifunction scale 200 includes a support structure 210 which integrates a large-area display 220 and a platform region 210 (where the user will stand when the scale 200 is in use). In such an embodiment, the display 220 is essentially the full length of the scale 20, but not full width. This display size is closer in dimensions to a tablet computing device (such as an iPad). The sensor circuitry in the platform region 210 includes electrodes for physiological and biometric sensing.

As discussed in more detail below in reference to FIGS. 3A-D, the display 220 is capable of presenting a myriad of information to the user, including specific data to encourage the user to use the scale to monitor exercise and perform certain specific types and/or forms of exercise (e.g., for a certain period of time, walk fast, run, jog in place, perform your favorite exercise as stored in the user profile) and/or patterns of exercise (as displayed, e.g., exercising the heart for intervals with periods of rest in between and one or more repetitions thereof). These user-specific aspects can be particularly advantageous especially with the circuitry in the scale being configured to wirelessly or in a wired mode, download data from wearable devices (e.g., chest strap, watch, phone) as worn during scale-instructed exercise (and/or even when standing on scale). As such these peripheral devices can capture details of the scale-noted exercise including heart rate ramp up/down, energy expenditure, etc., and append the scale's own measurements of the user when the user returns to stand on the scale, thereby forming a more complete data set of physiologic response to exercise.

Figure 3A:
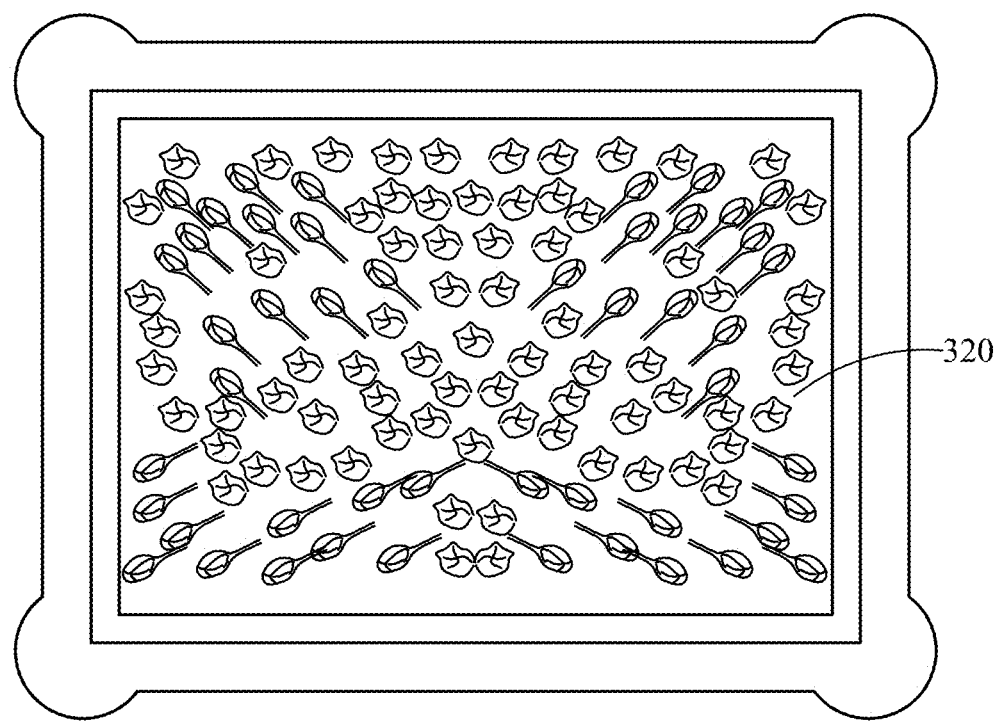

FIG. 3A-D shows top views of a number of multifunction scale displays, consistent with various aspects of the present disclosure. FIG. 3A presents an exemplary image that may be selected by a user as a "screen saver," and displayed by the scale, in a large-area display mode 320, when not in use. In further embodiments, the scale, when not in use may enter "sleep mode" and present or display pleasant still or video images, including a slide-show of images selected by the user, such as family-photos or other pleasant preferred images or animations. In more specific embodiments of the present disclosure, a camera is communicatively coupled to the multifunction scale and operates with facial recognition software for identifying the user and greeting the user ("Hello Bob"). The apparatus may also identify the user based on multiple measurement characteristics (e.g., weight, body composition, body mass index (BMW), body fat percentage, PWV, etc., alone or correlated with additional measurements), and greet the user accordingly. Based on the identified user, the scale may operate in accordance with user-specific aspects as may relate to physiology or preferences such as for a "screen saver." For instance, biometric and physiological tests can be conducted, with the test results saved to the identified user's file (and/or the results sent to a user's doctor for further review and analysis), as well as a number of other functionalities, such as playing the user's favorite musical artist and loading the display to present the user with pertinent information. Further, the scale may offer multiple modes that the user may choose between to ensure greater accuracy of physiological testing results, such as "athlete mode" for users that are very active.

Figure 3B:
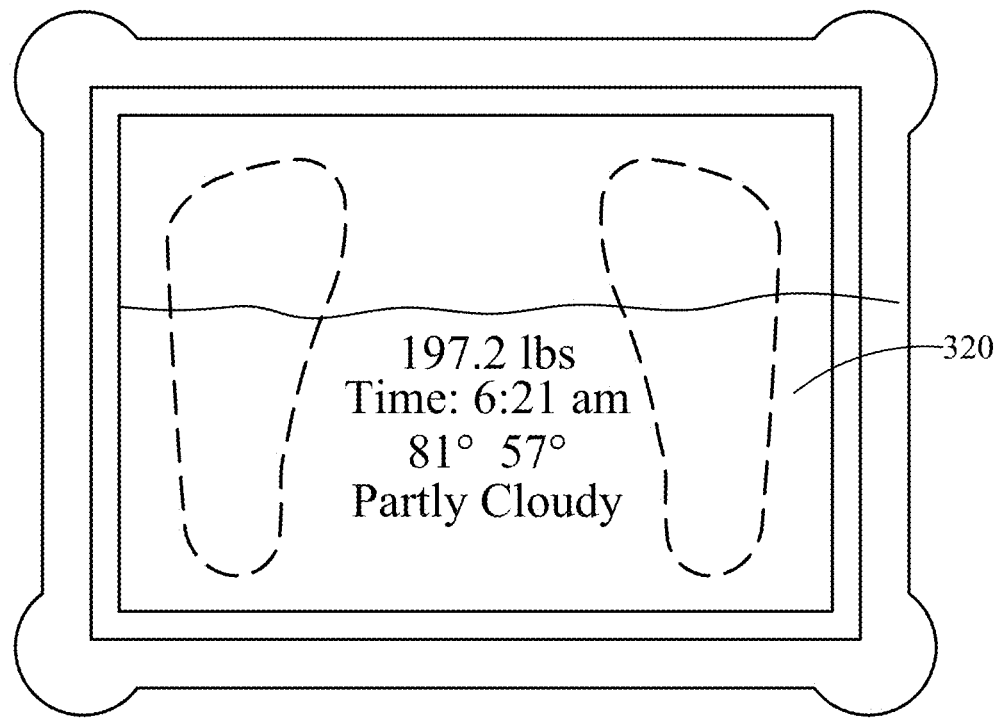
Figure 3C:
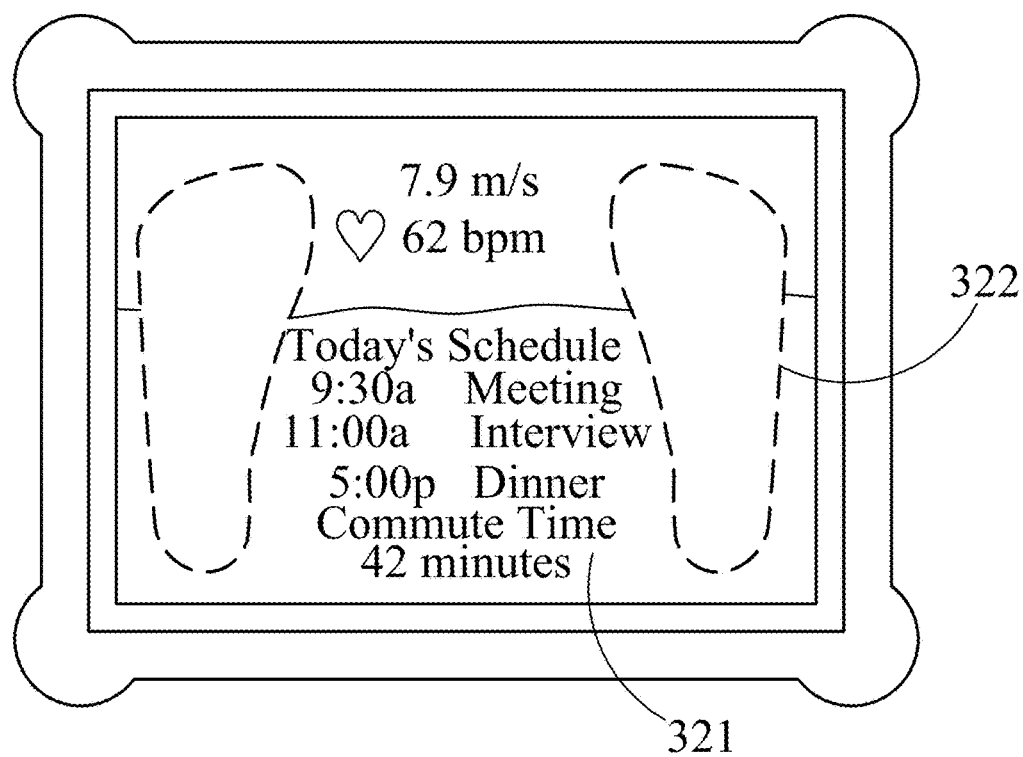
Figure 3D:
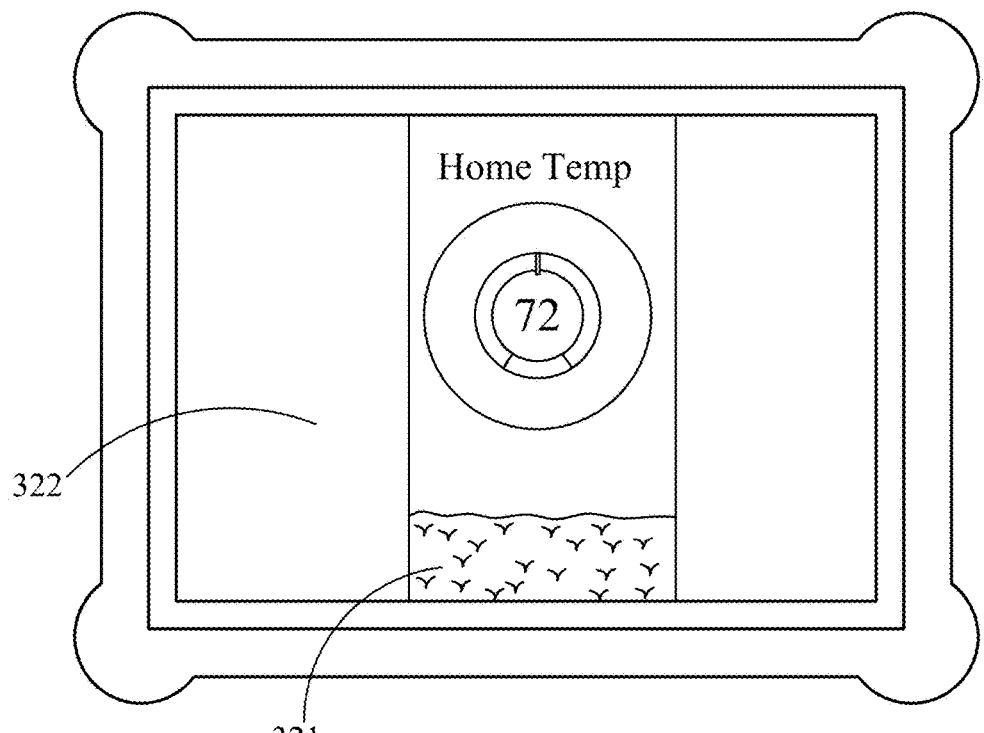

As shown in FIG. 3B, a relaxing ambience may be provided to the room where the multifunction scale is located, such as by displaying a video of waves lapping over sand, in a large-area display mode of the display 320 (when the user is not standing on the scale). In some embodiments, the scale plays an audio track associated with the video. In FIGS. 3C-D, a reduced-area display mode 321 is utilized when the user is standing on the scale. In such an embodiment, the display area where the user is standing, 322 is turned-off as the user's feet prevent the user from seeing this portion of the screen 322, and the disabling of the display area 322 reduces battery consumption of the display 320.

In FIGS. 3B-D, while the scale conducts tests on the user (e.g., weight measurements, body fat, biometric and physiological tests (e.g., ballistocardiogram (BCG) or pulse wave velocity (PWV), etc.) or whenever the user desires, the user is able to access other information from the scale such as the user's current weight, pulse rate, and time of day, among other user-configurable information. In further more specific embodiments (as shown in FIGS. 3B-D), the scale displays general or user-specific information, such as weather conditions, stocks, news, traffic conditions, home climate (e.g., screening air quality, oxygen level, temperature), commute times, user's daily schedule, personal reminders, or other information as may be collected by the scale via a wired or wireless connection to the internet, or to a smart device (e.g., a hand-held mobile or cellular phone, smart watch or other wearable electronic device, or tablet) or to fixed computing device (e.g., as a phone or watch). Information displayed on the scale is shown in an appropriately scaled font, composition and orientation to be readable from a standing position. As shown in FIG. 3D, in implementations of the disclosure directed to smart-homes, a multifunction scale user controls (via the touch-screen display) a plurality of other devices throughout the home such as a climate control system, security system, operation of the shower, etc. The electronic communications between the multifunction scale and the various devices may take the form of either wireless or wired communications.

FIG. 4 shows a multifunction scale 400 with large-area display (e.g., for a bathroom), consistent with various aspects of the present disclosure. The multifunction scale 400 includes circuitry, such as a camera and image processing circuitry, and user-targeted circuitry that operates to instruct the user for obtaining physiological characteristics of the user under different states of physical exertion, as characterized herein. The camera may be directed at the floor below the scale or the surrounding area. Based on the images processed (by the image processing circuitry) of the area surrounding the scale, the multifunction scale's large-area display depicts an image that mimics the surrounding area when idle. As shown in FIG. 4, the room is primarily furnished in black and white. The image processing circuitry identifies this black and white room theme based on the images captured by the camera and selects a color or combination of colors in a pattern or design that would mimic the décor of the room. As a result, the scale 400 is more likely to blend into the décor of the room and minimize the likelihood that the scale 400 will detract from the ambiance. In embodiments where the camera is directed at the floor, the scale 400 depicts an image indicative of the flooring below the scale 400, which would similarly minimize any detraction of aesthetics the scale would otherwise cast through its visually non-conforming presence. In either embodiment discussed above, when the multifunction scale 400 is idle, from a glance the scale 400 is effectively camouflaged. In other embodiments, the user and/or an interior designer may select a theme for the display based on the desired look for the room where the multifunction scale 400 is placed.

FIG. 5A is a flow chart depicting an example manner in which a user specific physiologic meter or scale may be programmed in accordance with the present disclosure. This flowchart uses a computer processor circuit (or CPU) along with a memory circuit shown herein as user profile memory 546A. The CPU operates in a low-power consumption mode, which may be in off mode or a low-power sleep mode, and at least one other higher power consumption mode of operation. As exemplary circuits for transitioning between such a low-power and higher power modes, the CPU can be integrated with presence and/or motion sense circuits, such as a passive infrared (PIR) circuit and/or pyro PIR circuit. In a typical application, the PIR circuit provides a constant flow of data indicative of amounts of radiation sensed in a field of view directed by the PIR circuit. For instance, the PIR circuit can be installed behind a transparent upper surface of the platform (such as through the display screen of the platform apparatus) and installed at an angle so that the motion of the user, as the user approaches the platform apparatus, can be sensed. Radiation from the user, upon reaching a certain detectable level, wakes up the CPU which then transitions from the low-power mode, as depicted in block 540, to a regular mode or active mode of operation. In alternative embodiments, the CPU transitions from the low-power mode of operation in response to another remote/wireless input used as an intrusion to awaken the CPU. In other embodiments, motion can be sensed with a single integrated microphone or microphone array, to detect the sounds of a user approaching, or user motion can be detected by an accelerometer integrated in the scale.

Accordingly, from block 540, flow proceeds to block 542 where the user or other presence is sensed as data is received at the platform apparatus. At block 544, the circuitry assesses whether the received data qualifies as requiring a wake up. If not, flow turns to block 540. If however, wake up is required, flow proceeds from block 544 to block 546 where the CPU assesses whether a possible previous user has approached the platform apparatus. This assessment is performed by the CPU accessing the user profile memory 546A and comparing data stored therein for one or more such previous users with criteria corresponding to the received data that caused the wake up. Such criteria might include, for example, the time of the day (early morning or late morning), the pace at which the user approached the platform apparatus as sensed by the motion detection circuitry, the height of the user as indicated by the motion sensing circuitry and/or a camera installed and integrated with the CPU, and/or more sophisticated bio-metric data provided by the user and/or automatically by the circuitry in the platform apparatus.

As discussed herein, such sophisticated circuitry can include one or more of the following user-specific attributes: foot length, type of foot arch, weight of user, manner and speed at which the user steps onto the platform apparatus, and/or sounds made by the user's motion or by speech. As is also conventional, facial or body-feature recognition may be used in connection with the camera and comparisons of images therefrom to images in the user profile memory.

From block 546, flow proceeds to block 548 where the CPU obtains and/or updates user corresponding data in the user profile memory. As a learning program is developed in the user profile memory, each access and use of the platform apparatus is used to expand on the data and profile for each such user. From block 548, flow proceeds to block 550 where a decision is made regarding whether the set of electrodes at the upper surface of the platform is ready for the user, which may be based on the data obtained from the user profile memory. For example, delays may ensue from the user moving his or her feet about the upper surface of the platform apparatus, as may occur while certain data is being retrieved by the CPU (whether internally or from an external source such as a program or configuration data updates from the Internet cloud) or when the user has stepped over a certain area configured for providing display information back to the user. If the electrodes are not ready for the user, flow proceeds from block 550 to block 552 to accommodate this delay.

Once the CPU determines that the electrodes are ready for use while the user is standing on the platform surface, flow proceeds to block 560. Stabilization of the user on the platform surface may be ascertained by injecting current through the electrodes via the interleaved arrangement thereof. Where such current is returned via other electrodes for a particular foot and/or foot size, and is consistent for a relatively brief period of time (e.g., a few seconds), the CPU can assume that the user is standing still and ready to use the electrodes and related circuitry.

At block 560, a decision is made that both the user and the platform apparatus are ready for measuring impedance and certain segments of the user's body, including at least one foot.

The remaining flow of FIG. 5A includes the application and sensing of current through the electrodes for finding the optimal electrodes (562) and for performing impedance measurements (block 564). These measurements are continued until completed at block 566 and all such useful measurements are recorded and are logged in the user profile memory for this specific user, at block 568. At block 572, the CPU generates output data to provide feedback as to the completion of the measurements and, as maybe indicated as a request via the user profile for this user, as an overall report on the progress for the user relative to previous measurements made for this user and that are stored in the user profile memory. Such feedback may be shown on the display, through a speaker with co-located apertures in the platform's housing for audible reception by the user, and/or by vibration circuitry which, upon vibration under control of the CPU, the user can sense through one or both feet while standing on the scale. From this output at block 572, flow returns to the low-power mode as indicated at block 574 with the return to the beginning of the flow at block 540.

FIG. 5B shows current paths 500 through the body of a user 505 standing on a scale 510 for the IPG trigger pulse and Foot IPG, consistent with various aspects of the present disclosure. Impedance measurements 515 are measured when the user 505 is standing and wearing clothing articles over the feet such as socks or shoes, within the practical limitations of capacitive-based impedance sensing, with energy limits considered safe for human use. The measurements 515 can also be made with non-clothing material placed between the user's bare feet and contact electrodes, such as thin films or sheets of plastic, glass, paper or wax paper, whereby the electrodes operate within energy limits considered safe for human use. The IPG measurements also can be sensed in the presence of callouses on the user's feet that normally diminish the quality of the signal.

As shown in FIG. 5B, the user 505 is standing on a scale 510, where the tissues of the user's body will be modeled as a series of impedance elements, and where the time-varying impedance elements change in response to cardiovascular and non-cardiovascular movements of the user. ECG and IPG measurements can be sensed through the feet and can be challenging to take due to small impedance signals with (1) low SNR, and because they are (2) frequently masked or distorted by other electrical activity in the body such as the muscle firings in the legs to maintain balance. The human body is unsteady while standing still, and constant changes in weight distribution occur to maintain balance. As such, cardiovascular signals that are measured with weighing scale-based sensors typically yield signals with poor SNR, such as the Foot IPG and standing BCG. Thus, such scale-based signals require a stable and high quality synchronous timing reference, to segment individual heartbeat-related signals for signal averaging to yield an averaged signal with higher SNR versus respective individual measurements.

The ECG can be used as the reference (or trigger) signal to segment a series of heartbeat-related signals measured by secondary sensors (optical, electrical, magnetic, pressure, microwave, piezo, etc.) for averaging a series of heartbeat-related signals together, to improve the SNR of the secondary measurement. The ECG has an intrinsically high SNR when measured with body-worn gel electrodes, or via dry electrodes on handgrip sensors. In contrast, the ECG has a low SNR when measured using foot electrodes while standing on said scale platforms; unless the user is standing perfectly still to eliminate electrical noises from the leg muscles firing due to body motion. As such, ECG measurements at the feet while standing are considered to be an unreliable trigger signal (low SNR). Therefore, it is often difficult to obtain a reliable cardiovascular trigger reference timing when using ECG sensors incorporated in base scale platform devices. Both Inan, et al. (IEEE Transactions on Information Technology in Biomedicine, 14:5, 1188-1196, 2010) and Shin, et al. (Physiological Measurement, 30, 679-693, 2009) have shown that the ECG component of the electrical signal measured between the two feet while standing was rapidly overpowered by the electromyogram (EMG) signal resulting from the leg muscle activity involved in maintaining balance.

The accuracy of cardiovascular information obtained from weighing scale platforms is also influenced by measurement time. The number of beats obtained from heartbeat-related signals for signal averaging is a function of measurement time and heart rate. The Mayo Clinic cites that typical resting heart rates range from 60 to 100 beats per minute. Therefore, short signal acquisition periods may yield a low number of beats to average, which may cause measurement uncertainty, also known as the standard error in the mean (SEM). SEM is the standard deviation of the sample mean estimate of a population mean. Where, SE is the standard error in the samples N, which is related to the standard error or the population S.

$$SE = \frac{S}{\sqrt{N}}$$

For example, a five second signal acquisition period may yield a maximum of five to eight beats for ensemble averaging, while a 10 second signal acquisition could yield 10-16 beats. However, the number of beats available for averaging and SNR determination is usually reduced for the following factors; (1) truncation of the first and last ensemble beat in the recording by the algorithm, (2) triggering beats falsely missed by triggering algorithm, (3) cardiorespiratory variability, (4) excessive body motion corrupting the trigger and Foot IPG signal, and (5) loss of foot contact with the measurement electrodes.

Sources of noise can require multiple solutions for overall SNR improvements for the signal being averaged. Longer measurement times increase the number of beats lost to truncation, false missed triggering, and excessive motion. Longer measurement times also reduce variability from cardiorespiratory effects. Therefore, if shorter measurement times (e.g., less than 30 seconds) are desired for scale-based sensor platforms, sensing improvements need to tolerate body motion and loss of foot contact with the measurement electrodes.

The human cardiovascular system includes a heart with four chambers, separated by valves that return blood to the heart from the venous system into the right side of the heart, through the pulmonary circulation to oxygenate the blood, which then returns to the left side of the heart, where the oxygenated blood is pressurized by the left ventricles and is pumped into the arterial circulation, where blood is distributed to the organs and tissues to supply oxygen. The cardiovascular or circulatory system is designed to ensure maintenance of oxygen availability and is often the limiting factor for cell survival. The heart normally pumps five to six liters of blood every minute during rest and maximum cardiac output during exercise can increase up to seven-fold, by modulating heart rate and stroke volume. The factors that affect heart rate include the degree of autonomic innervation, fitness level, age and hormones. Factors affecting stroke volume include heart size, fitness level, contractility or pre-ejection period, ejection duration, preload or end-diastolic volume, and afterload or systemic resistance. The cardiovascular system is constantly adapting to maintain a homeostasis (set point) that minimizes the work done by the heart to maintain cardiac output. As such, blood pressure is continually adjusting to minimize work demands during rest. Cardiovascular disease encompasses a variety of abnormalities in (or that affect) the cardiovascular system that degrade the efficiency of the system, which include but are not limited to chronically elevated blood pressure, elevated cholesterol levels, edema, endothelial dysfunction, arrhythmias, arterial stiffening, atherosclerosis, vascular wall thickening, stenosis, coronary artery disease, heart attack, stroke, renal dysfunction, enlarged heart, heart failure, diabetes, obesity and pulmonary disorders.

Each cardiac cycle results in a pulse of blood being delivered into the arterial tree. The heart completes cycles of atrial systole, delivering blood to the ventricles, followed by ventricular systole delivering blood into the lungs and the systemic arterial circulation, where the diastole cycle begins. In early diastole the ventricles relax and fill with blood, then in mid-diastole the atria and ventricles are relaxed and the ventricles continue to fill with blood. In late diastole, the sinoatrial node (the heart's pacemaker) depolarizes then contracts the atria, the ventricles are filled with more blood and the depolarization then reaches the atrioventricular node and enters the ventricular side, beginning the systole phase. The ventricles contract, and the blood is pumped from the ventricles to the arteries.

The ECG is the measurement of the heart's electrical activity and can be described in five phases. The P-wave represents atrial depolarization, the PR interval is the time between the P-wave and the start of the QRS complex. The QRS wave complex represents ventricular depolarization. The QRS complex is the strongest wave in the ECG and is frequently used as the de facto timing reference for the cardiovascular cycle. Atrial repolarization is masked by the QRS complex. The ST interval then follows which represents the period of zero potential between ventricular depolarization and repolarization. The cycle concludes with the T-wave representing ventricular repolarization.

The blood ejected into the arteries creates vascular movements due to the blood's momentum. The blood mass ejected by the heart first travels headward in the ascending aorta and travels around the aortic arch then travels down the descending aorta. The diameter of the aorta increases significantly during the systole phase due to the high compliance (low stiffness) of the aortic wall. Blood traveling in the descending aorta then bifurcates in the iliac branch, which then transitions into a stiffer arterial region due to the muscular artery composition of the leg arteries. The blood pulsation continues down the leg and foot. All along the way, the arteries branch into arteries of smaller diameter until reaching the capillary beds where the pulsatile blood flow turns into steady blood flow, delivering oxygen to the tissues. The blood then returns to the venous system terminating in the vena cava, where blood returns to the right atrium of the heart for the subsequent cardiac cycle.

Surprisingly, high quality simultaneous recordings of the Leg IPG and Foot IPG are attainable in a practical manner (e.g., a user operating the device correctly simply by standing on the impedance body scale foot electrodes), and can be used to obtain reliable trigger fiducial timings from the Leg IPG signal. This acquisition can be far less sensitive to motion-induced noise from the Leg EMG that often compromises Leg ECG measurements. Furthermore, it has been discovered that interleaving the two Kelvin electrode pairs for a single foot results in a design that is insensitive to foot placement within the boundaries of the overall electrode area. As such, the user is no longer constrained to comply with accurate foot placement on conventional single foot Kelvin arrangements, which are highly prone to introducing motion artifacts into the IPG signal, or result in a loss of contact if the foot is slightly misaligned. Interleaved designs begin when one or more electrode surfaces cross over a single imaginary boundary line separating an excitation and sensing electrode pair. The interleaving is configured to maintain uniform foot surface contact area on the excitation and sensing electrode pair, regardless of the positioning of the foot over the combined area of the electrode pair.

Various aspects of the present disclosure include a weighing scale platform (e.g., scale 110) of an area sufficient for an adult of average size to stand comfortably still and minimize postural swaying. The nominal scale length (same orientation as foot length) is 12 inches and the width is 12 inches. The width can be increased to be consistent with the feet at shoulder width or slightly broader (e.g., 14 to 18 inches, respectively).

FIG. 6 shows an example of the insensitivity to foot placement 600 on scale electrode pairs 605/610 with multiple excitation paths 620 and sensing current paths 615, consistent with various aspects of the present disclosure. An aspect of the platform is that it has a thickness and strength to support a human adult of at least 200 pounds without fracturing, and another aspect of the device platform is comprised of at least six electrodes, where the first electrode pair 605 is solid and the second electrode pair 610 is interleaved. Another aspect is that the first and second interleaved electrode pairs 605/610 are separated by a distance of at least 40+/−5 millimeters, where the nominal separation of less than 40 millimeters has been shown to degrade the single Foot IPG signal. Another key aspect is the electrode patterns are made from materials with low resistivity such as stainless steel, aluminum, hardened gold, ITO, index matched ITO (IMITO), carbon printed electrodes, conductive tapes, silver-impregnated carbon printed electrodes, conductive adhesives, and similar materials with resistivity lower than 300 ohms/sq. In the certain embodiments, the resistivity is below 150 ohms/sq. The electrodes are connected to the electronic circuitry in the scale by routing the electrodes around the edges of the scale to the surface below, or through at least one hole in the scale (e.g., a via hole).

Suitable electrode arrangements for dual Foot IPG measurements can be realized in other embodiments. In certain embodiments, the interleaved electrodes are patterned on the reverse side of a thin piece (e.g., less than 2 mm) of high-ion-exchange (HIE) glass, which is attached to a scale substrate and used in capacitive sensing mode. In certain embodiments, the interleaved electrodes are patterned onto a thin piece of paper or plastic which can be rolled up or folded for easy storage. In certain embodiments, the interleaved electrodes are integrated onto the surface of a tablet computer for portable IPG measurements. In certain embodiments, the interleaved electrodes are patterned onto a kapton substrate that is used as a flex circuit.

In certain embodiments, the scale area has a length of 10 inches with a width of eight inches for a miniature scale platform. Alternatively, the scale may be larger (up to 36 inches wide) for use in bariatric class scales. In certain embodiments, the scale platform with interleaved electrodes is incorporated into a floor tile that can be incorporated into a room such as a bathroom. In certain embodiments, the scale folds in half with a hinge for improved portability and storage. Alternatively, the scale platform is comprised of two separable halves, one half for the left foot and the other half for the right foot, for improved portability and storage. In certain embodiments for ambulatory measurements, the interleaved excitation and sensing electrode pairs are incorporated into a shoe insert for the detection of heart rate and a corresponding pulse arrival time (PAT). Alternatively, the interleaved excitation and sensing electrode pairs are incorporated into a pair of socks, to be worn for the detection of heart rate and a corresponding PAT.

In the present disclosure, the leg and foot impedance measurements can be simultaneously carried out using a multi-frequency approach, in which the leg and foot impedances are excited by currents modulated at two different frequencies, and the resulting voltages are selectively measured using a synchronous demodulator. This homodyning approach can be used to separate signals (in this case, the voltage drop due to the imposed current) with very high accuracy and selectivity.

This measurement configuration is based on a four-point configuration in order to minimize the impact of the contact resistance between the electrode and the foot, a practice well-known in the art of impedance measurement. In this configuration the current is injected from a set of two electrodes (the "injection" and "return" electrodes), and the voltage drop resulting from the passage of this current through the resistance is sensed by two separate electrodes (the "sense" electrodes), usually located in the path of the current. Since the sense electrodes are not carrying any current (by virtue of their connection to a high-impedance differential amplifier), the contact impedance does not significantly alter the sensed voltage.

In order to sense two distinct segments of the body (the legs and the foot), two separate current paths are defined by way of electrode positioning. Therefore two injection electrodes are used, each connected to a current source modulated at a different frequency. The injection electrode for leg impedance is located under the plantar region of the left foot, while the injection electrode for the Foot IPG is located under the heel of the right foot. Both current sources share the same return electrode located under the plantar region of the right foot. This is an illustrative example; other configurations may be used.

The sensing electrodes can be localized so as to sense the corresponding segments. Leg IPG sensing electrodes are located under the heels of each foot, while the two foot sensing electrodes are located under the heel and plantar areas of the right foot. The inter-digitated nature of the right foot electrodes ensures a four-point contact for proper impedance measurement, irrespective of the foot position, as already explained.

FIG. 7A depicts an example block diagram of circuitry for operating core circuits and modules of the multi-function scale, used in various specific embodiments of the present disclosure. Consistent with yet further embodiments of the present disclosure, FIG. 7A depicts an example block diagram of circuitry for operating core circuits and modules, including, for example, the operation of a CPU with the related and more specific circuit blocks/modules in FIGS. 8A-8B. As shown in the center of FIG. 7A, the main computer circuit 770 is shown with other previously-mentioned circuitry in a generalized manner without showing some of the detailed circuitry such as for amplification and current injection/sensing (772). The computer circuit 770 can be used as a control circuit with an internal memory circuit for causing, processing and/or receiving sensed input signals as at block 772. As discussed, these sensed signals can be responsive to injection current and/or these signals can be sensed at least for initially locating positions of the foot or feet on the platform area, by less complex grid-based sense circuitry surrounding the platform area as is conventional in capacitive touch-screen surfaces which, in certain embodiments, the platform area includes.

As noted, the memory circuit can be used not only for the user profile memory, but also to provide configuration and/or program code and/or other data such as user-specific data from another authorized source such as from a user monitoring his/her logged data and/or profile from a remote desk-top. The remote device or desktop can communicate with and access such data via a wireless communication circuit 776 via a wireless modem, router, ISDN channel, cellular systems, Bluetooth and/or other broadband pathway or private channel. For example, the wireless communication circuit 776 can provide an interface between an app on the user's cellular telephone/tablet (e.g., phablet, IPhone and/or IPad) and the platform apparatus, wherefrom the IPhone can be the output/input interface for the platform (scale) apparatus including, for example, an output display, speaker and/or microphone, and vibration circuitry; each of these I/O aspects and components being discussed herein in connection with other example embodiments.

A camera 778 and image encoder circuit 780 (with compression and related features) can also be incorporated as an option. As discussed above, the weighing scale components, as in block 782, are also optionally included in the housing which encloses and/or surrounds the platform apparatus.

For long-lasting battery life in the platform apparatus (batteries not shown), at least the CPU 770, the wireless communication circuit 776, and other current draining circuits are inactive unless and until activated in response to the intrusion/sense circuitry 788. As shown, one specific implementation employs a Conexant chip (e.g., CX93510) to assist in the low-power operation. This type of circuitry is specifically designed for motion sensors configured with a camera for visual verification and image and video monitoring applications (such as by supporting JPEG and MJPEG image compression and processing for both color and black and white images). When combined with an external CMOS sensor, the chip retrieves and stores compressed JPEG and audio data in an on-chip memory circuit (e.g., 256 KB/128 KB frame buffer) so as to alleviate the necessity of external memory. The chip uses a simple register set via the microprocessor interface and allows for wide flexibility in terms of compatible operation with another microprocessor.

In one specific embodiment, a method of using the platform with the plurality of electrodes concurrently contacting a limb of the user, includes operating such to automatically obtain measurement signals from the plurality of electrodes. As noted above, these measurement signals might initially be through less-complex (e.g., capacitive grid-type) sense circuitry. Before or while obtaining a plurality of measurement signals by operating the circuitry, the signal-sense circuitry 788 is used to sense wireless-signals indicative of the user approaching the platform and, in response, cause the CPU circuitry 770 to transition from a reduced power-consumption mode of operation and at least one higher power-consumption mode of operation. After the circuitry is operating in the higher power-consumption mode of operation, the CPU accesses the user-corresponding data stored in the memory circuit and thereafter causes a plurality of impedance-measurement signals to be obtained by using the plurality of electrodes while they are contacting the user via the platform; therefrom, the CPU generates signals corresponding to cardiovascular timings of the user, and such physiological measurements are communicated via the display.

This method can employ the signal-sense circuit as a passive infrared detector and with the CPU programmed (as a separate module) to evaluate whether radiation from the passive infrared detector is indicative of a human. For example, sensed levels of radiation that would correspond to a live being that has a size which is less than a person of a three-foot height, and/or not being sensed as moving for more than a couple seconds, can be assessed as being a non-human.

Accordingly, should the user be recognized as human, the CPU is activated and begins to attempt the discernment process of which user might be approaching. This is performed by the CPU accessing the user-corresponding data stored in the memory circuit (the user profile memory). If the user is recognized based on parameters such as discussed above (e.g., time of morning, speed of approach, etc.), the CPU can also select one of a plurality of different types of user-discernible visual/audible/tactile information and for presenting the discerned user with visual/audible/tactile information that was retrieved from the memory as being specific to the user. For example, user-selected visual/audible data can be outputted for the user. Also, responsive to the motion detection indication, the camera can be activated to capture at least one image of the user while the user is approaching the platform (and/or while the user is on the platform to log confirmation of the same user with the measured impedance information). As shown in block 774 of FIG. 7A, where a speaker is also integrated with the CPU, the user can simply command the platform apparatus to start the process and activation would accordingly proceed.

In another such method, the circuitry of FIG. 7A is used with the plurality of electrodes being interleaved and engaging the user, as a combination weighing scale (via block 782) and a physiologic user-specific impedance-measurement device. By using the impedance-measurement signals and obtaining at least two impedance-measurement signals between one foot of the user and another location of the user, the interleaved electrodes assist the CPU in providing measurement results that indicate one or more of the following user-specific attributes as being indicative or common to the user: foot impedance, foot length, and type of arch, and wherein one or more of the user-specific attributes are accessed, by being read or stored, in the memory circuit and identified as being specific to the user. This information can be later retrieved by the user, medical and/or security personnel, according to a data-access authorization protocol as might be established upon initial configuration for the user.

FIG. 7B shows an exemplary block diagram depicting the circuitry for interpreting signals received from electrodes. The input electrodes 705 transmit various electrical signals through the patient's body (depending on the desired biometric and physiological test to be conducted) and output electrodes 710 receive the modified signal as affected by a user's electrical impedance 715. Once received by the output electrodes 710, the modified signal is processed by processor circuitry 701 based on the selected test. Signal processing conducted by the processor circuitry 701 is discussed in more detail below (with regard to FIGS. 8A-B). In certain embodiments of the present disclosure, the circuitry within 701 is provided by Texas Instruments part # AFE4300.

FIGS. 8A-8B show example block diagrams depicting the circuitry for sensing and measuring the cardiovascular time-varying IPG raw signals and steps to obtain a filtered IPG waveform, consistent with various aspects of the present disclosure. The example block diagrams shown in FIGS. 8A-8B are separated into a leg impedance sub-circuit 800 and a foot impedance sub-circuit 805.

Excitation is provided by way of an excitation waveform circuit 810. The excitation waveform circuit 810 provides an excitation signal by way of various types of frequency signals (as is shown in FIG. 8A) or, more specifically, a square wave signal (as shown in FIG. 8B). As is shown in FIG. 8B, the square wave signal is a 5 V at a frequency between 15,625 Hz and 1 MHz is generated from a quartz oscillator (such as an ECS-100AC from ECS International, Inc.) divided down by a chain of toggle flip-flops (e.g. a CD4024 from Texas Instruments, Inc.), each dividing stage providing a frequency half of its input (i.e., 1 Mhz, 500 kHz, 250 kHz, 125 kHz, 62.5 kHz, 31.250 kHz and 15.625 kHz). This (square) wave is then AC-coupled, scaled down to the desired amplitude and fed to a voltage-controlled current source circuit 815. The generated current is passed through a decoupling capacitor (for safety) to the excitation electrode, and returned to ground through the return electrode (grounded-load configuration). Amplitudes of 1 and 4 mA peak-to-peak are typically used for Leg and Foot IPGs, respectively.

The voltage drop across the segment of interest (legs or foot) is sensed using an instrumentation differential amplifier (e.g., Analog Devices AD8421) 820. The sense electrodes on the scale are AC-coupled to the input of the differential amplifier 820 (configured for unity gain), and any residual DC offset is removed with a DC restoration circuit (as exemplified in Burr-Brown App Note Application Bulletin, SBOA003, 1991, or Burr-Brown/Texas Instruments INA118 datasheet).

The signal is then demodulated with a synchronous demodulator circuit 825. The demodulation is achieved in this example by multiplying the signal by 1 or −1 synchronously with the current excitation. Such alternating gain is provided by an operational amplifier and an analog switch (SPST), such as an ADG442 from Analog Devices). More specifically, the signal is connected to both positive and negative inputs through 10 kOhm resistors. The output is connected to the negative input with a 10 kOhm resistor as well, and the switch is connected between the ground and the positive input. When open, the gain of the stage is unity. When closed (positive input grounded), the stage acts as an inverting amplifier of the gain −1. Alternatively, other demodulators such as analog multipliers or mixers can be used.

Once demodulated, the signal is band-pass filtered (0.4-80 Hz) with a first-order band-pass filter circuit 830 before being amplified with a gain of 100 with a non-inverting amplifier circuit 835 (e.g., using an LT1058 operational amplifier from Linear Technologies). The amplified signal is further amplified by 10 and low-pass filtered (cut-off at 30 Hz) using a low-pass filter circuit 840 such as 2-pole Sallen-Key filter stage with gain. The signal is then ready for digitization and further processing. In certain embodiments, the amplified signal can be passed through an additional low-pass filter circuit 845 to determine body or foot impedance.

In certain embodiments, the generation of the excitation voltage signal, of appropriate frequency and amplitude, is carried out by a microcontroller, such as MSP430 (Texas Instruments, Inc.). The voltage waveform can be generated using the on-chip timers and digital input/outputs or pulse width modulation (PWM) peripherals, and scaled down to the appropriate voltage through fixed resistive dividers, active attenuators/amplifiers using on-chip or off-chip operational amplifiers, as well as programmable gain amplifiers or programmable resistors. Alternatively, the waveforms can be directly generated by on- or off-chip digital-to-analog converters (DACs).

In certain embodiments, the shape of the excitation is not square, but sinusoidal. Such configuration would reduce the requirements on bandwidth and slew rate for the current source and instrumentation amplifier. Harmonics, potentially leading to higher electromagnetic interference (EMI), would also be reduced. Such excitation may also reduce electronics noise on the circuit itself. Lastly, the lack of harmonics from sine wave excitation may provide a more flexible selection of frequencies in a multi-frequency impedance system, as excitation waveforms have fewer opportunities to interfere between each other. Due to the concentration of energy in the fundamental frequency, sine wave excitation could also be more power-efficient.

In certain embodiments, the shape of the excitation is not square, but trapezoidal. While not as optimal as a sinusoidal wave, trapezoidal waves (or square waves whose edges have been smoothed out by a limited bandwidth or slew rate) still provide an advantage in term of EMI and electronic noise due to the reduced harmonics.

To further reduce potential EMI, other strategies may be used, such as by dithering the square wave signal (i.e., introducing jitter in the edges following a fixed or random pattern) which leads to so-called spread spectrum signals, in which the energy is not localized at one specific frequency (or a set of harmonics), but rather distributed around a frequency (or a set of harmonics). An example of a spread-spectrum circuit suitable for Dual-IPG measurement is shown in FIG. 8B. Because of the synchronous demodulation scheme, phase-to-phase variability introduced by spread-spectrum techniques will not affect the impedance measurement. Such a spread-spectrum signal can be generated by, but not limited to, specialized circuits (e.g., Maxim MAX31C80, SiTime SiT9001), or generic microcontrollers (see Application Report SLAA291, Texas Instruments, Inc.). These spread-spectrum techniques can be combined with clock dividers to generate lower frequencies as well.

As may be clear to one skilled in the art, these methods of simultaneous measurement of impedance in the leg and foot can be used for standard Body Impedance Analysis (BIA), with the aim of extracting relative content of total water, free-water, fat mass and others. Impedance measurements for BIA are typically done at frequencies ranging from kilohertz up to several megahertz. The multi-frequency measurement methods described above can readily be used for such BIA, provided the circuit can be modified so that the DC component of the impedance is not canceled by the instrumentation amplifier (no DC restoration circuit used). The high-pass filter can be implemented after the instrumentation amplifier, enabling the measurement of the DC component used for BIA. This multi-frequency technique can also be combined with traditional sequential measurements often used for BIA, in which the impedance is measured at several frequencies sequentially. These measurements can be repeated in several body segments for segmental BIAs, using a switch matrix to drive the current into the desired body segments.

While FIG. 6 shows a circuit and electrode configuration suitable to measure two different segments (legs and one foot), this approach is not readily extendable to more segments due to the shared current return electrode (ground). To overcome this limitation, and in particular to provide simultaneous measurements in both feet, the system can be augmented with analog switches to provide time-multiplexing of the impedance measurements in the different segments. This multiplexing can either be a one-time sequencing (each segment is measured once), or interleaved at a high-enough frequency so that the signal can be simultaneously measured on each segment. The minimum multiplexing rate for proper reconstruction is twice the bandwidth of the measured signal, based on signal processing theory, which equals to about 100 Hz for the impedance signal considered here. The rate must also allow for the signal path to settle in between switching, usually limiting the maximum multiplexing rate. Referring to FIG. 13A, one cycle might start the measurement of the leg impedance and left foot impedances (similarly to previously described, sharing a common return electrode), but then follow with a measurement of the right foot after reconfiguring the switches. Typical switch configurations for the various measurements are shown in the table below.

|  | Switch #1 (Sw1) | Switch #2 (Sw2) | Switch #3 (Sw3) | Switch #4 (Sw4) |
|---|---|---|---|---|
| Legs | A | A or B | A or B | A |
| Right Foot | A | A or B | B | A |
| Left Foot | B | B | A or B | B |

Since right and left feet are measured sequentially, one should note that a unique current source (at the same frequency) may be used to measure both, providing that the current source is not connected to the two feet simultaneously through the switches, in which case the current would be divided between two paths. One should also note that a fully-sequential measurement, using a single current source (at a single frequency) successively connected to the three different injection electrodes, could be used as well, with the proper switch configuration sequence (no split current path).

In certain embodiments, the measurement of various body segments, and in particular the legs, right foot and left foot, is achieved simultaneously due to as many floating current sources as segments to be measured, running at separate frequency so they can individually be demodulated. Such configuration is exemplified in FIG. 13B for three segments (legs, right and left feet). Such configuration has the advantage to provide true simultaneous measurements without the added complexity of time-multiplexing/demultiplexing, and associated switching circuitry. An example of such floating current source can be found in Plickett, et al., Physiological Measurement, 32 (2011). Another approach to floating current sources is the use of transformer-coupled current sources (as depicted in FIG. 13C). Using transformers to inject current into the electrodes enables the use of simpler, grounded-load current sources on the primary, while the electrodes are connected to the secondary. Turn ratio would typically be 1:1, and since frequencies of interest for impedance measurement are typically in the 10-1000 kHz (occasionally 1 kHz for BIA), relatively small transformers can be used. In order to limit the common mode voltage of the body, one of the electrodes in contact with the foot can be grounded.

While certain embodiments presented in the above specification have used current sources for excitation, it should be clear to a person skilled in the art that the excitation can also be performed by a voltage source, where the resulting injection current is monitored by a current sense circuit so that impedance can still be derived by the ratio of the sensed voltage (on the sense electrodes) over the sensed current (injected in the excitation electrodes).

It should be noted that broadband spectroscopy methods could also be used for measuring impedances at several frequencies. Such technique has the advantage of lower EMI and simultaneous measurement of impedances at numerous frequencies. These methods typically use a chirp signal, a noise signal or an impulse signal to excite the load (impedance) at many frequencies simultaneously, while sampling the resulting response at high frequency so as to allow the computation (usually in the frequency domain) of the impedance over the desired frequency range. Combined with time-multiplexing and current switching described above, multi-segment broadband spectroscopy can be readily achieved.

Various aspects of the present disclosure are directed toward robust timing extraction of the blood pressure pulse in the foot which is achieved by means of a two-step processing. In a first step, the usually high-SNR Leg IPG is used to derive a reference (trigger) timing for each heart pulse. In a second step, a specific timing in the lower-SNR Foot IPG is extracted by detecting its associated feature within a restricted window of time around the timing of the Leg IPG. Such guided detection leads to a naturally more robust detection of foot timings.

FIG. 9 shows an example block diagram depicting signal processing steps to obtain fiducial references from the individual Leg IPG "beats," which are subsequently used to obtain fiducials in the Foot IPG, consistent with various aspects of the present disclosure. In the first step, as shown in block 900, the Leg IP and the Foot IPG are simultaneously measured. As shown at 905, the Leg IPG is low-pass filtered at 20 Hz with an 8-pole Butterworth filter, and inverted so that pulses have an upward peak. The location of the pulses is then determined by taking the derivative of this signal, integrating over a 100 ms moving window, zeroing the negative values, removing the large artifacts by zeroing values beyond 15× the median of the signal, zeroing the values below a threshold defined by the mean of the signal, and then searching for local maxima. Local maxima closer than a defined refractory period of 300 ms to the preceding ones are dismissed. The result is a time series of pulse reference timings.

As is shown in 910, the foot IPG is low-pass filtered at 25 Hz with an 8-pole Butterworth filter and inverted (so that pulses have an upward peak). Segments starting from the timings extracted (915) from the Leg IPG (reference timings) and extending to 80% of the previous pulse interval, but no longer than one second, are defined in the Foot IPG. This defines the time windows where the Foot IPG is expected to occur, avoiding misdetection outside of these windows. In each segment, the derivative of the signal is computed, and the point of maximum positive derivative (maximum acceleration) is extracted. The foot of the IPG signal is then computed using an intersecting tangent method, where the fiducial (920) is defined by the intersection between a first tangent to the IPG at the point of maximum positive derivative and a second tangent to the minimum of the IPG on the left of the maximum positive derivative within the segment.

The time series resulting from this two-step extraction is then used in conjunction with another signal to facilitate additional processing. In the present disclosure, these timings are used as reference timings to improve the SNR of BCG signals to subsequently extract intervals between a timing of the BCG (typically the I-wave) and the Foot IPG for the purpose of computing the PWV, as previously disclosed in U.S. 2013/0310700 (Wiard). In certain embodiments, the timings of the Leg IPG are used as reference timings to improve the SNR of BCG signals, and the foot IPG timings are used to extract intervals between timing fiducials of the improved BCG (typically the I-wave) and the Foot IPG for the purpose of computing the PTT and the (PWV).

In certain embodiments, the processing steps include an individual pulse SNR computation after individual timings have been extracted, either in Leg IPG or Foot IPG. Following the computation of the SNRs, pulses with a SNR below a threshold value are eliminated from the time series, in order to prevent propagating noise in subsequent processing steps. The individual SNRs may be computed in a variety of methods known to a person skilled in the art. For instance, an estimated pulse can be computed by ensemble averaging segments of signal around the pulse reference timing. The noise associated with each pulse is defined as the difference between the pulse and the estimated pulse. The SNR is then the ratio of the root-mean-square (RMS) value of the estimated pulse over the RMS value of the noise for that pulse.

In certain embodiments, the time interval between the Leg IPG pulses, (as detected by the above-mentioned methods), and the Foot IPG pulses, also detected by the above-mentioned methods, is extracted. The Leg IPG measuring a pulse occurring earlier in the legs is compared to the pulse from the Foot IPG, the interval between these two being related to the propagation speed in the lower body, i.e., the peripheral vasculature. This provides complementary information to the interval extracted between the BCG and the Foot IPG, for instance, and can be used to decouple central versus peripheral vascular properties. It is also complementary to information derived from timings between the BCG and the Leg ICG.

In FIG. 10, the Leg IP and the Foot IPG are simultaneously measured (1000), the Leg IPG is low-pass filtered (1005), the foot IPG is low-pass filtered (1010), and segments starting from the timings are extracted (1015) from the Leg IPG (reference timings). The segments of the Foot IPG extracted based on the Leg IPG timings are ensemble-averaged (1020) to produce a higher SNR Foot IPG pulse. From this ensemble-averaged signal, the start of the pulse is extracted using the same intersecting tangent approach as described earlier. This approach enables the extraction of accurate timings in the Foot IPG even if the impedance signal is dominated by noise. These timings can then be used together with timings extracted from the BCG for the purpose of computing the PTT and (PWV). Timings derived from ensemble-averaged waveforms and individual waveforms can also be both extracted, for the purpose of comparison, averaging and error-detection.

Specific timings that can be extracted from the IPG pulses (from either leg or foot) are related (but not limited) to the peak of the pulse, to the minimum preceding the peak, or to the maximum second derivative (maximum rate of acceleration) preceding the point of maximum derivative. An IPG pulse and the extraction of a fiducial (1025) in the IPG can also be performed by several other signal processing methods, including (but not limited to) template matching, cross-correlation, wavelet-decomposition, or short window Fourier transform.

In certain embodiments, a dual-Foot IPG is measured, allowing the detection of blood pressure pulses in both feet. Such information can be used for diagnostic of peripheral arterial diseases (PAD) by comparing the relative PATs in both feet to look for asymmetries. It can also be used to increase the robustness of the measurement by allowing one foot to have poor contact with electrodes (or no contact at all). SNR measurements can be used to assess the quality of the signal in each foot, and to select the best signal for downstream analysis. Timings extracted from each foot can be compared and set to flag potentially inaccurate PWV measurements due to arterial peripheral disease, in the event these timings are different by more than a defined threshold. Alternatively, timings from both feet can be pooled to increase the overall SNR if their difference is below a defined threshold.

In certain embodiments, the disclosure is used to measure a PWV, where the IPG is augmented by the addition of BCG sensing into the weighing scale to determine characteristic fiducials between the BCG and Leg IPG trigger, or the BCG and Foot IPG. The BCG sensors are comprised typically of the same strain gage set used to determine the bodyweight of the user. The load cells are typically wired into a bridge configuration to create a sensitive resistance change with small displacements due to the ejection of the blood into the aorta, where the circulatory or cardiovascular force produce movements within the body on the nominal order of 1-3 Newtons. BCG forces can be greater than or less than the nominal range in cases such as high or low cardiac output.

FIG. 11 shows an example configuration to obtain the PTT, using the first IPG as the triggering pulse for the Foot IPG and BCG, consistent with various aspects of the present disclosure. The I-wave of the BCG 1100 as illustrated normally depicts the headward force due to cardiac ejection of blood into the ascending aorta which can be used as a timing fiducial indicative of the pressure pulse initiation of the user's proximal aorta relative to the user's heart. The J-wave is also indicative of timings in the systole phase and also incorporates information related to the strength of cardiac ejection and the ejection duration. The K-Wave also provides systolic and vascular information of the user's aorta. The characteristic timings of these and other BCG waves can be used as fiducials that can be related to fiducials of the IPG signals of the present disclosure.

FIG. 12 shows another example of a scale 1200 with interleaved foot electrodes 1205 to inject and sense current from one foot to another foot, and within one foot, consistent with various aspects of the present disclosure. FIG. 13A-C3 shows various examples of a scale 1300 with interleaved foot electrodes 1305 to inject and sense current from one foot to another foot, and measure Foot IPG signals in both feet, consistent with various aspects of the present disclosure. FIGS. 14A-D shows an example breakdown of a scale 1400 with interleaved foot electrodes 1405 to inject and sense current from one foot to another foot, and within one foot, consistent with various aspects of the present disclosure.

FIG. 15 shows an example block diagram of circuit-based building blocks, consistent with various aspects of the present disclosure. The various circuit-based building blocks shown in FIG. 15 can be implemented in connection with the various aspects discussed herein. In the example shown, the block diagram includes foot electrodes 1500 that can collect the IPG signals. Further, the block diagram includes strain gauges 1505, and an LED/photosensor 1510. The foot electrodes 1500 is configured with a leg impedance measurement circuit 1515, a foot impedance measurement circuit 1520, and an optional second foot impedance measurement circuit 1525. The leg impedance measurement circuit 1515, the foot impedance measurement circuit 1520, and the optional second foot impedance measurement circuit 1525 report the measurements collected to a processor circuit 1545.

The processor circuit 1545 also collects data from a weight measurement circuit 1530 and an optional balance measurement circuit 1535 that are configured with the strain gauges 1505. Further, an optional photoplethysmogram (PPG) measurement circuit 1540, which collects data from the LED/photosensor 1510, can also provide data to the processor circuit 1545.

The processor circuit 1545 is powered via a power circuit 1550. Further, the processor circuit 1545 also collects user input data from a user interface 1555 that can include a touch screen and/or buttons. The data collected/measured by the processor circuit 1545 is shown to the user via a display 1560. Additionally, the data collected/measured by the processor circuit 1545 can be stored in a memory circuit 1580. Further, the processor circuit 1545 can optionally control a haptic feedback circuit 1565, a speaker or buzzer 1570, a wired/wireless interface 1575, and an auxiliary sensor 1585.

FIG. 16 shows an example flow diagram, consistent with various aspects of the present disclosure. As shown in block 1600, a PWV length is entered. As is shown in block 1605, a user's weight, balance, leg, and foot impedance are measured (as is consistent with various aspects of the present disclosure). As is shown at block 1610, the integrity of signals is checked (e.g., signal to noise ratio). If the signal integrity check is not met, the user's weight, balance, leg, and foot impedance are measured again (block 1605), if the signals integrity check is met, the leg impedance pulse timings are extracted (as is shown at block 1615). As is shown at block 1620, foot impedance and pulse timings are then extracted, and as is shown at block 1625, BCG timings are extracted. As is shown at block 1630, a timings quality check is performed. If the timings quality check is not validated, the user's weight, balance, leg and foot impedance are again measured (block 1605). If the timings quality check is validated, the PWV is calculated (as is shown at block 1635). Finally, as is shown at block 1640, the PWV is then displayed to the user.

FIG. 17 shows an example scale 1700 communicatively coupled to a wireless device, consistent with various aspects of the present disclosure. As described herein, a display 1705 displays the various aspects measured by the scale 1700. The scale can also wirelessly broadcast the measurements to a wireless device 1710.

FIGS. 18A-C show example impedance as measured through different parts of the foot based on the foot position, consistent with various aspects of the present disclosure. For instance, example impedance measurement configurations may be implemented using a dynamic electrode configuration for measurement of foot impedance and related timings, consistent with various aspects of the present disclosure. Dynamic electrode configuration may be implemented using independently-configurable electrodes to optimize the impedance measurement. As shown in FIG. 18A, interleaved electrodes 1800 are connected to an impedance processor circuit 1805 to determine foot length, foot position, and/or foot impedance. As is shown in FIG. 18B, an impedance measurement is determined regardless of foot position 1810 based on measurement of the placement of the foot across the electrodes 1800. This is based in part in the electrodes 1800 that are engaged (blackened) and in contact with the foot (based on the foot position 1810), which is shown in FIG. 18C.

More specifically regarding FIG. 18A, configuration can include connection/de-connection of the individual electrodes 1800 to the impedance processor circuit 1805, their configuration as current-carrying electrodes (injection or return), sense electrodes (positive or negative), or both. The configuration can either be preset based on user information, or updated at each measurement (dynamic reconfiguration) to optimize a given parameter (impedance SNR, measurement location). The system may for instance algorithmically determine which electrodes under the foot to use in order to obtain the highest SNR in the pulse impedance signal. Such optimization algorithm may include iteratively switching configurations and measuring the resulting impedance, then selecting the best-suited configuration. Alternatively, the system may first, through a sequential impedance measurement between each individual electrode 1800 and another electrode in contact with the body (such as an electrode in electrode pair 205 on the other foot), determine which electrodes are in contact with the foot. By determining the two most apart electrodes, the foot size is determined. Heel location can also be determined in this manner, as can other characteristics such as foot arch type. These parameters can then be used to determine programmatically (in an automated manner by CPU/logic circuitry) which electrodes should be selected for current injection and return (as well as sensing if a Kelvin connection issued) in order to obtain the best foot IPG.

In various embodiments involving the dynamically reconfigurable electrode array 1800/1805, an electrode array set is selected to measure the same portion (or segment) of the foot, irrespective of the foot location on the array. FIG. 18B illustrates the case of several foot positions on a static array (a fixed set of electrodes are used for measurement at the heel and plantar/toe areas, with a fixed gap of an inactive electrode or insulating material between them). Depending on the position of the foot, the active electrodes are contacting the foot at different locations, thereby sensing a different volume (or segment) of the foot. If the IPG is used by itself (e.g., for heart measurement), such discrepancies may be non-consequential. However, if timings derived from the IPG are referred to other timings (e.g., R-wave from the ECG, or specific timing in the BCG), such as for the calculation of a PTT or PWV, the small shifts in IPG timings due to the sensing of slightly different volumes in the foot (e.g., if the foot is not always placed at the same position on the electrodes) can introduce an error in the calculation of the interval. Such location variations can readily occur in the day-to-day use of the scale. With respect to FIG. 18B for instance, the timing of the peak of the IPG from the foot placement on the right (sensing the toe/plantar region) would be later than from the foot placement on the left, which senses more of the heel volume (the pulse reaches first the heel, then the plantar region). Factors influencing the magnitude of these discrepancies include foot shape (flat or not) and foot length.

Various embodiments address challenges relating to foot placement. FIG. 18C shows an example embodiment involving dynamic reconfiguration of the electrodes to reduce such foot placement-induced variations. As an example, by sensing the location of the heel first (as described above), it is possible to activate only a subset of electrodes under the heel, and another subset of electrodes separated by a fixed distance (1800). The other electrodes (e.g., unused electrodes) are left disconnected. The sensed volume will therefore always be the same, producing consistent timings. The electrode configuration leading to the most consistent results may also be informed by the foot impedance, foot length, the type of arch (all of which can be measured by the electrode array as shown above), but also by the user ID (foot information can be stored for each user, then looked up based on automatic user recognition or manual selection (e.g., in a look-up-table stored for each user in a memory circuit accessible by the CPU circuit in the scale)).

Accordingly, in certain embodiments, the impedance-measurement apparatus measures impedance using a plurality of electrodes contacting one foot and with at least one other electrode (typically many) at a location distal from the foot. The plurality of electrodes (contacting the one foot) is arranged on the platform and in a pattern configured to inject current signals and sense signals in response thereto, for the same segment of the foot so that the timing of the pulse-based measurements does not vary simply because the user placed the one foot at a slightly different position on the platform or scale. Thus, in FIG. 18A, the foot-to-electrode locations for the heel are different locations than that shown in FIGS. 18B and 18C. As this different foot placement might occur from day to day for the user, the timing and related impedance measurements should be for the same (internal) segment of the foot. By having the computer processor circuit inject current and sense responsive signals to first locate the foot on the electrodes (e.g., sensing where positions of the foot's heel plantar regions and/or toes), the pattern of foot-to-electrode locations permits the foot to move laterally, horizontally and both laterally and horizontally via the different electrode locations, while collecting impedance measurements relative to the same segment of the foot.

The BCG/IPG system can be used to determine the PTT of the user, by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. In certain embodiments, the BCG/IPG system is used to determine the PWV of the user, by identification of the characteristic length representing the length of the user's arteries, and by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. The system of the present disclosure and alternate embodiments may be suitable for determining the arterial stiffness (or arterial compliance) and/or cardiovascular risk of the user regardless of the position of the user's feet within the bounds of the interleaved electrodes. In certain embodiments, the weighing scale system incorporates the use of strain gage load cells and six or eight electrodes to measure a plurality of signals including: bodyweight, BCG, body mass index, fat percentage, muscle mass percentage, and body water percentage, heart rate, heart rate variability, PTT, and PWV measured simultaneously or synchronously when the user stands on the scale to provide a comprehensive analysis of the health and wellness of the user.

In other certain embodiments, the PTT and PWV are computed using timings from the Leg IPG or Foot IPG for arrival times, and using timings from a sensor located on the upper body (as opposed to the scale measuring the BCG) to detect the start of the pulse. Such sensor may include an impedance sensor for impedance cardiography, a hand-to-hand impedance sensor, a photoplethysmogram on the chest, neck, head, arms or hands, or an accelerometer on the chest (seismocardiograph) or head.

Communication of the biometric information is another aspect of the present disclosure. The biometric results from the user are then stored in the memory on the scale and displayed to the user via a display on the scale, audible communication from the scale, and/or the data is communicated to a peripheral device such as a computer, smart phone, or tablet computing device. The communication occurs directly to the peripheral device with a wired connection, or can be sent to the peripheral device through wireless communication protocols such as Bluetooth or WiFi. Computations such as signal analyses described therein may be carried out locally on the scale, in a smartphone or computer, or in a remote processor (cloud computing).

Various embodiments of the present invention include a scale configured and arranged to extract physiological data and to operate in a physiological assessment mode being directed to general assessment of cardio-related health. The physiological data extracted via the sale, in accordance with specific embodiments, is useful for correlating to symptoms and/or ultimate diagnosis of disorders and/or diseases. For example, physiological data that is directed to general assessment of cardio related health can include data indicative of arterial stiffness, flutter tachycardia, (exercise induced) sinus tachycardia, and other cardiac conditions, disorders, and/or dis-functions that might otherwise be suggested by ECG and/or holter monitor data collection effort.

Other aspects of the present disclosure are directed toward apparatuses or methods that include the use of at least two electrodes that contact feet of a user. Further, circuitry is provided to determine a pulse arrival time at the foot based on the recording of two or more impedance signals from the set of electrodes. Additionally, a second set of circuitry is provided to extract a first pulse arrival time from a first impedance signal and use the first pulse arrival time as a timing reference to extract and process a second pulse arrival time in a second impedance signal.

Reference may also be made to the following published patent documents, U.S. Patent Publication 2010/0094147 and U.S. Patent Publication 2013/0310700, which are, together with the references cited therein, herein fully incorporated by reference for the purposes of sensors and sensing technology. The aspects discussed therein may be implemented in connection with one or more of embodiments and implementations of the present disclosure (as well as with those shown in the figures). In view of the description herein, those skilled in the art will recognize that many changes may be made thereto without departing from the spirit and scope of the present disclosure.

As illustrated herein, various circuit-based building blocks and/or modules may be implemented to carry out one or more of the operations and activities described herein shown in the block-diagram-type figures. In such contexts, these building blocks and/or modules represent circuits that carry out one or more of these or related operations/activities. For example, in certain of the embodiments discussed above (such as the pulse circuitry modularized as shown in FIGS. 8A-B), one or more blocks/modules are discrete logic circuits or programmable logic circuits configured and arranged for implementing these operations/activities, as in the circuit blocks/modules shown. In certain embodiments, the programmable circuit is one or more computer circuits programmed to execute a set (or sets) of instructions (and/or configuration data). The instructions (and/or configuration data) can be in the form of firmware or software stored in and accessible form, a memory (circuit). As an example, first and second modules/blocks include a combination of a CPU hardware-based circuit and a set of instructions in the form of firmware, where the first module/block includes a first CPU hardware circuit with one set of instructions and the second module/block includes a second CPU hardware circuit with another set of instructions.

Based upon the above discussion and illustrations, those skilled in the art will readily recognize that various modifications and changes may be made to the present disclosure without strictly following the exemplary embodiments and applications illustrated and described herein. For example, the input terminals as shown and discussed may be replaced with terminals of different arrangements, and different types and numbers of input configurations (e.g., involving different types of input circuits and related connectivity). Such modifications do not depart from the true spirit and scope of the present disclosure, including that set forth in the following claims.

What is claimed is:

1. A weighing scale comprising:
   a platform region configured and arranged to support a user while the user stands on the platform region; and circuitry configured and arranged to be integrated with a support structure including the platform region and sensor circuitry therein, the platform region configured and arranged to engage the user with the sensor circuitry while the user stands on the platform region, and to collect physiological data from the user via the sensor circuitry, and the circuitry being configured and arranged to:
measure physiological parameters of the user that are indicative of baseline user measurements while the user stands on the platform region;
operate in a physiological assessment mode that is different from a mode of operation of the circuitry associated with the baseline user measurements, the physiological assessment mode including the circuitry configured to:
instruct the user to change physiological states relative to a first physiological state associated with the baseline user measurements;
instruct the user to return to the weighing scale after changing physiological states;
thereafter, upon recognizing that the user has returned to the support structure, to engage the sensor circuitry via the platform region and measure or collect the physiological parameters which are obtained while the user is in the changed physiological state and while the user is returning toward the first physiological state; and
provide information indicative of fitness or health of the user by comparing the physiological parameters that are indicative of the baseline user measurements and the physiological parameters obtained while the user is in the changed physiological state and while the user is returning toward the first physiological state.

2. The weighing scale of claim 1, wherein the changed physiological state is a transient state indicative of a cardiovascular state and the physiological parameters are cardiovascular parameters, and wherein the circuitry is in communication with a display, and the circuitry and the display are configured and arranged to instruct the user to return to the support structure after instructing the user to cause a change to the user's physiological state and in sufficient time to measure or collect physiological data from the user.

3. The weighing scale of claim 1, wherein the circuitry is configured to recommend a specific exercise mode, type or pattern to change physiological states.

4. The scale of claim 3, wherein the circuitry is configured and arranged to instruct the user to return to the weighing scale after a threshold amount of time of performing the recommended specific exercise mode, type or pattern.

5. The weighing scale of claim 1, wherein the circuitry is configured to recommend a specific type of exercise that is directly related to the baseline user measurements for performing a physiological fitness test and to physiological data obtained or collected on behalf of the user.

6. A weighing scale comprising:
a platform region configured and arranged to support a user while the user stands on the platform region;
a support structure including the platform region and sensor circuitry therein, the platform region configured and arranged to engage the user with the sensor circuitry while the user stands on the platform region, and to collect physiological data from the user via the sensor circuitry;

circuitry configured and arranged to:
operate in a first mode by instructing a user to engage the sensor circuitry via the platform region, during a first physiological state of the user, the sensor circuitry being responsive to the engaging by collecting physiological data from the user, the physiological data being indicative of baseline values,
operate in a physiological assessment mode indicative of cardiovascular health of the user, the physiological assessment mode being different from the first mode, by instructing the user:
to change physiological states relative to the first physiological state, and
to engage the sensor circuitry via the platform region, after instructing the user to change physiological states, the sensor circuitry being responsive to the engaging by collecting physiological data from the user indicative of the changed physiological state of the user relative to the baseline values and while the user is returning toward the first physiological state; and
receive the physiological data from the sensor circuitry;
determine physiological parameters of the user based on respective sets of the physiological data and a physiological state associated with each set; and
provide information indicative of fitness or health of the user by comparing the physiological parameters determined using physiological data indicative of baseline values with the physiological parameters determined using physiological data obtained while the user being in the changed physiological state and while the user is returning toward the first physiological state; and
a communication driver configured and arranged to provide information, based on the determined physiological parameters, from the circuitry to a display for viewing by the user.

7. The weighing scale of claim 6, wherein the circuitry is configured and arranged to:
instruct the user to change physiological states by increasing physical exertion, immediately prior to the user engaging the sensor circuitry and collecting the physiological data indicative of the physical exertion state of the user,
after collecting the physiological data indicative of baseline values, instruct the user to change the user's physiological state by reducing exertion and thereafter to re-engage the sensor circuitry via the platform region, therein collecting physiological data indicative of a reduced-exertion state, and
determine the physiological parameters of the user based on the physiological data collected after the user has reduced exertion, relative to the physiological data indicative of the physical exertion state of the user.

8. The weighing scale of claim 6, wherein the circuitry is further configured and arranged to correlate the physiological parameters in each of a plurality of physiological states to determine a physical health of the user, the physiological parameters and physiological states being cardiovascular parameters and states.

9. The weighing scale of claim 6, wherein the circuitry is further configured and arranged to:
provide the information indicative of fitness or health by determining recovery parameters using the physiological data; and
determine, in response to determining the information indicative of physical fitness or health of the user, actions to encourage improvement of the user's fitness and to display information pertaining to the actions via the display.

10. The weighing scale of claim 6, wherein the circuitry is configured and arranged with the support structure to receive touch signal data indicative of engagement of the user on the platform region and an associated position and movement of the user, and the communication driver is further configured and arranged to receive the touch signal data from the circuitry, process the touch signal data, and determine the associated position and movement with such touch signals.

11. The weighing scale of claim 6, wherein the display is configured and arranged with the support structure and wherein the communication driver is further configured and arranged to recognize whether the user is standing on the platform region and, in response thereto, presenting information via a large-area display mode when the user is not standing on the platform region and, via a reduced-area display mode in a reduced-area display region of the platform region which is adjacent to feet of the user, when the user is standing on the platform region, presenting information that corresponds to the physiological parameters of the user.

12. The weighing scale of claim 6, further including
a camera configured and arranged to capture image data indicative of an area around the weighing scale and presence of the user;
image processing circuitry configured and arranged to receive the captured image data from the camera and determine:
color and pattern themes associated with the image data of the area around the weighing scale, and
the presence of the user; and
the display is further configured and arranged
in an active mode, determined by presence of the user by the image processing circuitry, to present information that corresponds to the physiological parameters of the user, and
in an idle mode, determined by non-presence of the user by the image processing circuitry, to present an image indicative of the area around the weighing scale, based on the image data processed by the image processing circuitry.

13. The weighing scale of claim 6, wherein the circuitry is further configured and arranged to receive externally acquired physiological data from external personal electronic devices, and use the externally acquired physiological data, in conjunction with the physiological data acquired from the sensor circuitry, to determine the physiological parameters of the user.

14. A user-supporting scale comprising:
a platform region configured and arranged to support a user while the user stands on the platform region;
sensor circuitry;
a data-access circuit configured and arranged to provide access to user-specific data including stored physiological parameters of the user in response to or developed by the sensor circuitry and to store physiological parameters of the user determined by the sensor circuitry;
a support structure including the platform region and the sensor circuitry therein, the platform region configured and arranged to engage the user with the sensor circuitry while the user stands on the platform region, and to collect physiological data from the user via the sensor circuitry; and
circuitry being configured and arranged to:
operate in a first mode by
instructing a user to engage the sensor circuitry via the platform region, during a first physiological state of the user, the sensor circuitry being responsive to the engaging by collecting physiological data from the user, the physiological data being indicative of baseline values,
operate in a mode that is different from the first mode by:
instructing the user to change the user's physiological state, and
instructing the user to engage the sensor circuitry via the platform region, after instructing the user to change the user's physiological state, the sensor circuitry being responsive to the engaging by collecting physiological data from the user indicative of the changed physiological state of the user relative to the baseline values and while the user is returning toward the first physiological state;
receive the physiological data from the sensor circuitry; and
determine physiological parameters of the user based on respective sets of the physiological data and a physiological state associated with each set including physiological data obtained while the user is in the changed physiological state and while the user is returning toward the first physiological state; and
a communication driver configured and arranged to provide information, based on the determined physiological parameters, from the circuitry to a display for viewing by the user.

15. The user-supporting scale of claim 14, wherein the circuitry further configured and arranged to determine the change in physical health of the user over time by:
accessing the stored physiological parameters of the user in the data-access circuit, and
comparing current physiological parameters of the user to the stored physiological parameters of the user to determine the change in physical health of the user over time.

16. The user-supporting scale of claim 14, wherein the circuitry is further configured and arranged to compare a physical health of the user to a health metric by:
accessing current physiological parameters and the health metric associated with at least one of a number of the user-specific physiological parameters stored in the data-access circuit including age and an indication of the user's physical condition for exercise, and
comparing the current physiological parameters of the user to the-health metric to determine physical fitness of the user compared to the health metric.

17. The user-supporting scale of claim 14, wherein the circuitry is further configured and arranged to transmit data indicative of a physical health of the user, the physiological parameters of the user, or the physiological data of the user to external personal electronic devices, via the data-access circuit.

18. The user-supporting scale of claim 14, wherein the physiological assessment mode further includes a fitness testing mode and the circuitry is further configured and arranged to transmit data indicative of fitness feedback including changes to fitness regimens to external personal electronic devices, via the data-access circuit.

19. The user-supporting scale of claim 14, further including the display configured and arranged with the support structure to display data through the platform region and to display data throughout the platform region and including an area on which the user stands, with the data being displayed between the user's feet while the user stands on the area and being displayed throughout the platform region while the user is not standing on the area, wherein:

the display is further configured and arranged to receive touch signal data indicative of engagement of the user on the platform region and an associated shape of the user's foot, and the communication driver is communicatively coupled with the data-access circuit and configured and arranged to receive the touch signal data from the display, process the touch signal data, and determine an associated position and movement of the user's foot with such touch signal data.

20. The user-supporting scale of claim 14, wherein the data-access circuit is further configured and arranged to log and trend physiological data including weight and body composition over a period of time.

21. The user-supporting scale of claim 14, wherein the circuitry is further configured and arranged to:

access the data-access circuit to determine previous recovery times of the user after physical exertion;

instruct the user to engage the sensor circuitry on the platform region of the scale, after physical exertion, until the user has fully recovered to the baseline values;

receive the physiological data from the sensor circuitry; and compare current recovery time of the user to the previous recovery times of the user to determine the change in physical health of the user over time.

* * * * *